United States Patent
Chen et al.

(10) Patent No.: US 8,957,024 B2
(45) Date of Patent: Feb. 17, 2015

(54) COMPOSITION AND METHODS FOR REDUCING OPIOID-INDUCED PRURITUS

(75) Inventors: Zhou-Feng Chen, St. Louis, MO (US); Xianyu Liu, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 13/560,620

(22) Filed: Jul. 27, 2012

(65) Prior Publication Data
US 2013/0065832 A1 Mar. 14, 2013

Related U.S. Application Data

(60) Provisional application No. 61/512,274, filed on Jul. 27, 2011.

(51) Int. Cl.
A61K 38/00 (2006.01)
A61P 17/04 (2006.01)
C07K 7/04 (2006.01)
C07K 14/705 (2006.01)
A61K 45/06 (2006.01)
A61K 38/17 (2006.01)

(52) U.S. Cl.
CPC .......... *A61K 38/177* (2013.01); *C07K 2319/00* (2013.01); *C07K 14/705* (2013.01); *A61K 45/06* (2013.01)
USPC .......................................... 514/18.4; 530/300

(58) Field of Classification Search
CPC ..... A61K 38/177; A61K 31/00; A61K 45/06; C07K 2319/00; C07K 14/705
See application file for complete search history.

(56) References Cited

U.S. PATENT DOCUMENTS

| | | | |
|---|---|---|---|
| 5,521,183 A | 5/1996 | Woodward | |
| 6,136,839 A | 10/2000 | Isakson | |
| 6,375,957 B1 | 4/2002 | Kaiko | |
| 6,475,494 B2 | 11/2002 | Kaiko | |
| 6,696,066 B2 | 2/2004 | Kaiko | |
| 6,982,283 B2 | 1/2006 | Ueno | |
| 2003/0054030 A1 | 3/2003 | Gordon | |
| 2003/0100057 A1 | 5/2003 | Feder | |
| 2004/0116440 A1 | 6/2004 | Higginbottom | |
| 2007/0225209 A1* | 9/2007 | Roch et al. | 514/2 |

OTHER PUBLICATIONS

Rudinger, Peptide Hormones, JA Parsons, Ed., 1976, pp. 1-7.*
Sigma, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Sun et al, A gastrin-releasing peptide receptor mediates the itch sensation in the spinal cord, Nature, 2007, 448, pp. 700-704.*
Fischer, Cellular Uptake Mechanisms and Potential Therapeutic Utility of Peptidic Cell Delivery W!ctors: Progress 2001-2006, Medicinal Research Reviews, 2007, 27, pp. 755-795.*
Matthes, "Loss of morphine-induced analgesia, reward effect and withdrawal symptoms in mice lacking the mu-opioid-receptor gene." Nature, 1996, pp. 819-823, vol. 383.
McMahon, "Itching for an explanation." Trends Neurosci, 1992, pp. 497-501, vol.
Metze, "Efficacy and safety of naltrexone, an oral opiate receptor antagonist, in the treatment of pruritus in internal and dermatological diseases." J Am Acad Dermatol,1999, pp. 533-539, vol. 41.
Milligan, "G protein-coupled receptor hetero-dimerization: contribution to pharmacology and function." Br J Pharmacol, 2009, pp. 5-14, vol. 158.
Nichols, "Transmission of chronic nociception by spinal neurons expressing the substance P receptor." Science, 1999, pp. 1558-15561, vol. 286.
Pan, "Diversity and complexity of the mu opioid receptor gene: alternative pre-mRNA splicing and promoters." DNA Cell Biol, 2005, pp. 736-750, vol. 24.
Pasternak, "Molecular insights into mu opioid pharmacology: From the clinic to the bench." Clin J Pain, 2010, pp. S3-S9, vol. 26 Suppl 10.
Pasternak, "Multiple opiate receptors: deja vu all over again." Neuropharmacology, 2004, pp. 312-323, vol. 47, Suppl 1.
Patel, "An itch to be scratched." Neuron, 2010, pp. 334-339, vol. 68.
Paus, "Frontiers in pruritus research: scratching the brain for more effective itch therapy." J Clin Invest, 2006, pp. 1174-1186, vol. 116.
Pfeiffer, "Heterodimerization of somatostatin and opioid receptors cross-modulates phosphorylation, internalization, and desensitization." J Biol Chem, 2002, pp. 19762-19772, vol. 277.
Ravindranathan, "Functional characterization of human variants of the mu-opioid receptor gene." Proc Natl Acad Sci, 2009, pp. 10811-10816, vol. 106.
Ross, "Loss of Inhibitory Interneurons in the Dorsal Spinal Cord and Elevated Itch in Bhlhb5 Mutant Mice." Neuron, 2010, pp. 886-898, vol. 65.
Samways, "Opioid elevation of intracellular free calcium: possible mechanisms and physiological relevance." Cell Signal, 2006, pp. 151-161, vol. 18.

(Continued)

*Primary Examiner* — Julie Ha
*Assistant Examiner* — Li Ni Komatsu
(74) *Attorney, Agent, or Firm* — Polsinelli PC

(57) ABSTRACT

The present invention encompasses methods and combinations for substantially inhibiting the opioid-induced internalization of gastrin-releasing peptide receptor (GRPR) in a pruritus specific neuron. Such methods and combinations provide a direct means of treating opioid-induce pruritus without compromising opioid analgesia.

4 Claims, 35 Drawing Sheets
(9 of 35 Drawing Sheet(s) Filed in Color)

(56) References Cited

OTHER PUBLICATIONS

Schwarze, "In vivo protein transduction: delivery of a biologically active protein into the mouse." Science, 1999, pp. 1569-1572, vol. 285.
Sora, "Opiate receptor knockout mice define mu receptor roles in endogenous nociceptive responses and morphine-induced induced analgesia." Proc Natl Acad Sci, 1997, pp. 1544-1549, vol. 94.
Sun, "A gastrin-releasing peptide receptor mediates the itch sensation in the spinal cord." Nature, 2007, pp. 700-703, vol. 448.
Sun, "Cellular basis of itch sensation." Science, 2009, pp. 1531-1534, vol. 325.
Szarvas, "Neuraxial opioid-induced pruritus: a review." J Clin Anesth, 2003, pp. 234-239, vol. 15.
Tan, "Therapeutic potential of RNA interference in pain medicine." Open Pain J, 2009, pp. 57-53, vol. 2.
Trafton, "Postsynaptic signaling via the [mu]-opioid receptor: responses of dorsal horn neurons to exogenous opioids and noxious stimulation." J Neurosci, 2000, pp. 8578-8584, vol. 20.
Van Baarlen, "Differential NF-kappaB pathways induction by *Lactobacillus plantarum* in the duodenum of healthy humans correlating with immune tolerance." Proc Natl Acad Sci, 2009, pp. 2371-2376, vol. 106.
Waldhoer, "A heterodimer-selective agonist shows in vivo relevance of G protein-coupled receptor dimers." Proc Natl Acad Sci, 2005, pp. 9050-9055, vol. 102.
Whistler, "Functional dissociation of mu opioid receptor signaling and endocytosis: implications for the biology of opiate tolerance and addiction." Neuron, 1999, pp. 737-746, vol. 23.
Xie, "Genetic alteration of phospholipase C beta3 expression modulates behavioral and cellular responses to mu opioids." Proc Natl Acad Sci, 1999, pp. 10385-10390, vol. 96.
Zhao, "Central serotonergic neurons are differentially required for opioid analgesia but not for morphine tolerance or morphine reward." Proc Natl Acad Sci, 2007, pp. 14519-14524, vol. 104.
Final U.S. Office action from related U.S. Appl. No. 12/740,819 dated Aug. 10, 2012.
U.S. Office action from related U.S. Appl. No. 12/740,819 dated Mar. 2, 2012.
International Search Report and Written Opinion mailed Jan. 28, 2009 from related International Application No. PCT/US08/082267, 8 pgs.
Abbadie, "Comparative immunohistochemical distributions of carboxy terminus epitopes from the mu-opioid receptor splice variants MOR-1D, MOR-1 and MOR-1C in the mouse and rat CNS." Neuroscience, 2000, pp. 141-153, vol. 100, No. 1.
Agnati, "Molecular mechanisms and therapeutical implications of intramembrane receptor/receptor interactions among heptahelical receptors with examples from the striatopallidal GABA neurons." Pharmacol Rev, 2003, pp. 509-550, vol. 55, No. 3.
Alvarez, "mu-Opioid receptors: Ligand-dependent activation of potassium conductance, desensitization, and internalization." J Neurosci, 2002, pp. 5769-5776, vol. 22, No. 13.
Andoh, "Evidence for separate involvement of different mu-opioid receptor subtypes in itch and analgesia induced by supraspinal action of opioids." J Pharmacol Sci, 2008, pp. 667-670, vol. 106, No. 4.
Ballantyne, "Itching after epidural and spinal opiates". Pain, 1988, pp. 149-160, vol. 33, No. 2.
Bergasa, "The pruritus of cholestasis." J Hepatol, 2005, pp. 1078-1088, vol. 43, No. 6.
Bouvier, "Oligomerization of G-protein-coupled transmitter receptors." Nat Rev Neurosci, 2001, pp. 274-286, vol. 2, No. 4.
Carstens, "Dorsal horn neurons expressing NK-1 receptors mediate scratching in rats." Neuroreport, 2010, pp. 303-308, vol. 21.
Carstens, "Responses of rat spinal dorsal horn neurons to intracutaneous microinjection of histamine, capsaicin, and other irritants." J Neurophysiol, 1997, pp. 2499-2514, vol. 77, No. 5.
Chaney, "Side effects of intrathecal and epidural opioids." Can J Anaesth, 1995, pp. 891-903, vol. 42, No. 10.

Chen, "The paired homeodomain protein DRG11 is required for the projection of cutaneous sensory afferent fibers to the dorsal spinal cord." Neuron, 2001, pp. 59-73, vol. 31, No. 1.
Chothiai, "Canonical Structures for the Hypervariable regions of Immunoglobulins." J. Mol. Bio., 1987, pp. 901-917, vol. 196, No. 4.
Chothia, "Conformations of immunoglobulin Hypervariable Regions." Nature, 1989, pp. 877-883, vol. 342, No. 6252.
Co, "Humanized Antibodies for Antiviral Therapy." PNAS, 1991, pp. 2869-2873, vol. 88, No. 7.
Cvejic, "Dimerization of the delta opioid receptor: implication for a role in receptor internalization." J Biol Chem, 1997, pp. 26959-26964, vol. 272, No. 43.
Davidson, "The multiple pathways for itch and their interactions with pain." Trends Neurosci, 2010, pp. 550-558, vol. 33.
Davidson, The itch-producing agents histamine and cowhage activate separate populations of primate spinothalamic tract neurons. J Neurosci, 2007, pp. 10007-10014, vol. 27, No. 37.
Fairbanks, "Spinal antinociceptive synergism between morphine and clonidine persists in mice made acutely or chronically tolerant to morphine." J Pharmacol Exp Ther, 1999, pp. 1107-1116, vol. 288, No. 3.
Gallup, "New quick method for isolating RNA from laser captured cells stained by immunofluorescent immunohistochemistry; RNA suitable for direct use in fluorogenic TaqMan one-step real-time RT-PCR." Biol Proced Online, 2005, pp. 70-92, vol. 7.
George, "Oligomerization of mu- and delta-opioid receptors. Generation of novel functional properties." J Biol Chem, 2000, pp. 26128-26135, vol. 275.
Hales, "Pruritus after epidural morphine". Lancet, 1980, p. 204, vol. 2.
Hampton, "Loss of bombesin-induced feeding suppression in gastrin-releasing peptide receptor-deficient mice." Proc Natl Acad Sci U S A, 1998, pp. 3188-3192, vol. 95, No. 6.
Han, "Phospholipase Cbeta 3 mediates the scratching response activated by the histamine H1 receptor on C-fiber nociceptive neurons." Neuron, 2006, pp. 691-703, vol. 52.
Hipser, "Role of antibodies in developing drugs that target G-protein-coupled receptor dimers." Mt Sinai J Med, 2010, pp. 374-380, vol. 77, No. 4.
Hylden, "Intrathecal morphine in mice: a new technique." Eur J Pharmacol, 1980, pp. 313-316, vol. 67. Ikoma et al., "The neurobiology of itch." Nat Rev Neurosci, 2006, pp. 535-547, vol. 7.
Ikoma, "The neurobiology of itch." Nat Rev Neurosci, 2006, pp. 535-547, vol. 7.
Jensen, "International Union of Pharmacology. LXVIII. Mammalian bombesin receptors: nomenclature, distribution, pharmacology, signaling, and functions in normal and disease states." Pharmacol Rev, 2008, pp. 1-42, vol. 60, No. 1.
Jones, "The pruritus of cholestasis: from bile acids to opiate agonists." Hepatology, 1990, pp. 884-887, vol. 11.
Jordan, "G-protein-coupled receptor heterodimerization modulates receptor function." Nature, 1999, pp. 697-700, vol. 399.
Keith, "Morphine activates opioid receptors without causing their rapid internalization." J Biol Chem, 1996, pp. 19021-19024; vol. 271.
Kieffer, "Opioids: first lessons from knockout mice." Trends Pharmacol Sci, 1999, pp. 19-26, vol. 20.
Ko, "An experimental itch model in monkeys: characterization of intrathecal morphine-induced scratching and antinociception." Anesthesiology, 2000, pp. 795-805, vol. 92.
Ko, "The role of central mu opioid receptors in opioid-induced itch in primates." J Pharmacol Exp Ther, 2004, pp. 169-176, vol. 310, No. 1.
Koch, "C-terminal splice variants of the mouse mu-opioid receptor differ in morphine-induced internalization and receptor resensitization." J Biol Chem, 2001, pp. 31408-31414, vol. 276.
Kroog, "Mammalian bombesin receptors." Med Res Rev, 1995, pp. 389-417, vol. 15.
Kuraishi, "Itch-scratch responses induced by opioids through central mu opioid receptors in mice." J Biomed Sci, 2000, pp. 248-252, vol. 7.

(56) References Cited

OTHER PUBLICATIONS

Lagerstrom, "VGLUT2-dependent sensory neurons in the TRPV1 population regulate pain and itch." Neuron, 2010, pp. 529-542, vol. 68.

Law, "Molecular mechanisms and regulation of opioid receptor signaling." Annu Rev Pharmacol Toxicol, 2000, pp. 389-430, vol. 40.

Ling, "Differential development of acute tolerance to analgesia, respiratory depression, gastrointestinal transit and hormone release in a morphine infusion model." Life Sci, 1989, pp. 1627-1636, vol. 45.

Liu, "Activity-dependent modulation of limbic dopamine D3 receptors by CaMKII." Neuron, 2009, pp. 425-438; vol. 61.

Liu, "VGLUT2-dependent glutamate release from nociceptors is required to sense pain and suppress itch." Neuron, 2010, pp. 543-556, vol. 68.

Loh, "mu Opioid receptor knockout in mice: effects on ligand-induced analgesia and morphine lethality." Brain Res Mol Brain Res, 1998, pp. 321-326, vol. 54.

Lopez, "Membrane functional organisation and dynamic of mu-opioid receptors." Cell Mol Life Sci, 2009, pp. 2093-2108, vol. 66, No. 13.

Luo, "An efficient intrathecal delivery of small interfering RNA to the spinal cord and peripheral neurons." Mol Pain, 2005, pp. 29, vol. 1.

Luo, "The majority of N-methyl-D-aspartate receptor complexes in adult rat cerebral cortex contain at least three different subunits (NR1/NR2A/NR2B)." Mol Pharmacol, 1997, pp. 79-86, vol. 51, No. 1.

Mao, "The scaffold protein Homer1b/c links metabotropic glutamate receptor 5 to extracellular signal-regulated protein kinase cascades in neurons." J Neurosci, 2005, pp. 2741-2752, vol. 25.

\* cited by examiner

G

H

D

E

A

| | |
|---|---|
| Tat | YGRKKRRQRRR (SEQ. ID NO. 550) |
| MOR1D$_{CT}$ | SCLNPVLYAFLDENFKRCFREFCIPTSST IEQQNSARIRQNTREHPSTANTVDRTNHQ RNEEPSS (SEQ. ID NO. 590) |
| MOR1$_{CT}$ | SCLNPVLYAFLDENFKRCFREFCIPTSST IEQQNSARIRQNTREHPSTANTVDRTNHQ LENLEAETAPLP (SEQ. ID NO. 591) |
| Tat-MOR1D$_{CT}$ | YGRKKRRQRRR RNEEPSS (SEQ. ID NO. 568) |
| Control | YGRKKRRQRRR SEPNSER. (SEQ. ID NO. 569) |

MOR1-2B SEQUENCE (SEQ. ID NO. 589)

MDSSAAPTNA SNCTDALAYS SCSPAPSPGS WVNLSHLDGN LSDPCGPNRT DLGGRDSLCP 70          80          90         100        110        120
PTGSPSMITA ITIMALYSIV CVVGLFGNFL VMYVIVRYTK MKTATNIYIF NLALADALAT 130        140        150        160        170        180
STLPFQSVNY LMGTWPFGTI LCKIVISIDY YNMFTSIFTL CTMSVDRYIA VCHPVKALDF 190        200        210        220        230        240
RTPRNAKIIN VCNWILSSAI GLPVMFMATT KYRQGSIDCT LTFSHPTWYW ENLLKICVFI 250        260        270        280        290        300
FAFIMPVLII TVCYGLMILR LKSVRMLSGS KEKDRNLRRI TRMVLVVVAV FIVCWTPIHI 310        320        330        340        350        360
YVIIKALVTI PETTFQTVSW HFCIALGYTN SCLNPVLYAF LDENFKRCFR EFCIPTSSNI 370        380        390
EQQNSTRIRQ NTRDHPSTAN TVDRTNHQRE RRQKSDW

FIG. 13

COMPOSITION AND METHODS FOR REDUCING OPIOID-INDUCED PRURITUS

CROSS REFERENCE TO RELATED APPLICATIONS

This application claims the priority of U.S. provisional application No. 61/512,274, filed Jul. 27, 2011, which is hereby incorporated by reference in its entirety.

GOVERNMENTAL RIGHTS

This invention was made with government support under RO1 AR056318 awarded by The National Institute of Arthritis and Musculoskeletal and Skin Diseases. The government has certain rights in the invention.

FIELD OF THE INVENTION

The invention encompasses methods and combinations for substantially inhibiting the opioid-induced internalization of GRPR in a pruritus specific neuron. Such methods and combinations provide a direct means of treating opioid-induce pruritus without compromising opioid analgesia.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

Itch and pain are two fundamental sensory perceptions evoked by distinct external inputs. They are encoded and transmitted by primary nociceptive fibers and varying subpopulations of dorsal horn neurons. The ability to discriminate between itch and pain allows animals to employ the proper motor response (scratching vs. withdrawal) so that potentially damaging stimuli from the environment can be avoided. Intriguingly, it has been well documented that itch and pain may counteract each other under some conditions. Indeed, a wide range of noxious stimuli including thermal, mechanical, chemical and electrical stimuli are able to inhibit itch. Conversely, it is widely assumed that itch may be unmasked by pain reduction, and one of the most cited examples of this antagonistic relationship is opioid-induced itch, or pruritus. In fact, pruritus is one of the most prevalent acute side effects of the spinal or epidural use of opioids in patients who undergo pain treatment or in those who receive cesarean section, which has hampered the use of opioids as an analgesic to their full extent. Current treatment is to use antagonists against the μ opioid receptor, which also affects opioid analgesia. There is a need in the art, therefore, to separate opioid analgesia and opioid itch to treat opioid itch without compromising opioid analgesia.

SUMMARY OF THE INVENTION

One aspect of the invention encompasses a method for substantially inhibiting the opioid-induced internalization of GRPR in a pruritus specific neuron. The method comprises substantially inhibiting the interaction of GRPR with MOR1D.

Another aspect of the invention encompasses a method for reducing opioid-induced pruritus in a subject. The method comprises administering a compound that substantially inhibits the opioid-mediated interaction of MOR1D and GRPR in a pruritus specific neuron, such that the GRPR receptor is not internalized in response to opioid administration.

Yet another aspect of the invention encompasses a combination comprising an agent that substantially inhibits the interaction of GRPR with MOR1D in a pruritus specific neuron of the subject, and at least one analgesic agent.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

*p<0.05. (H) Spinal MOR1D mRNA level was significantly reduced by siRNA specific to MOR exon 1 and exon 9 as detected by qRT-PCR. *p<0.05. In all experiments, n=5~8 per group. Error bars represent standard error.

Figure 3:
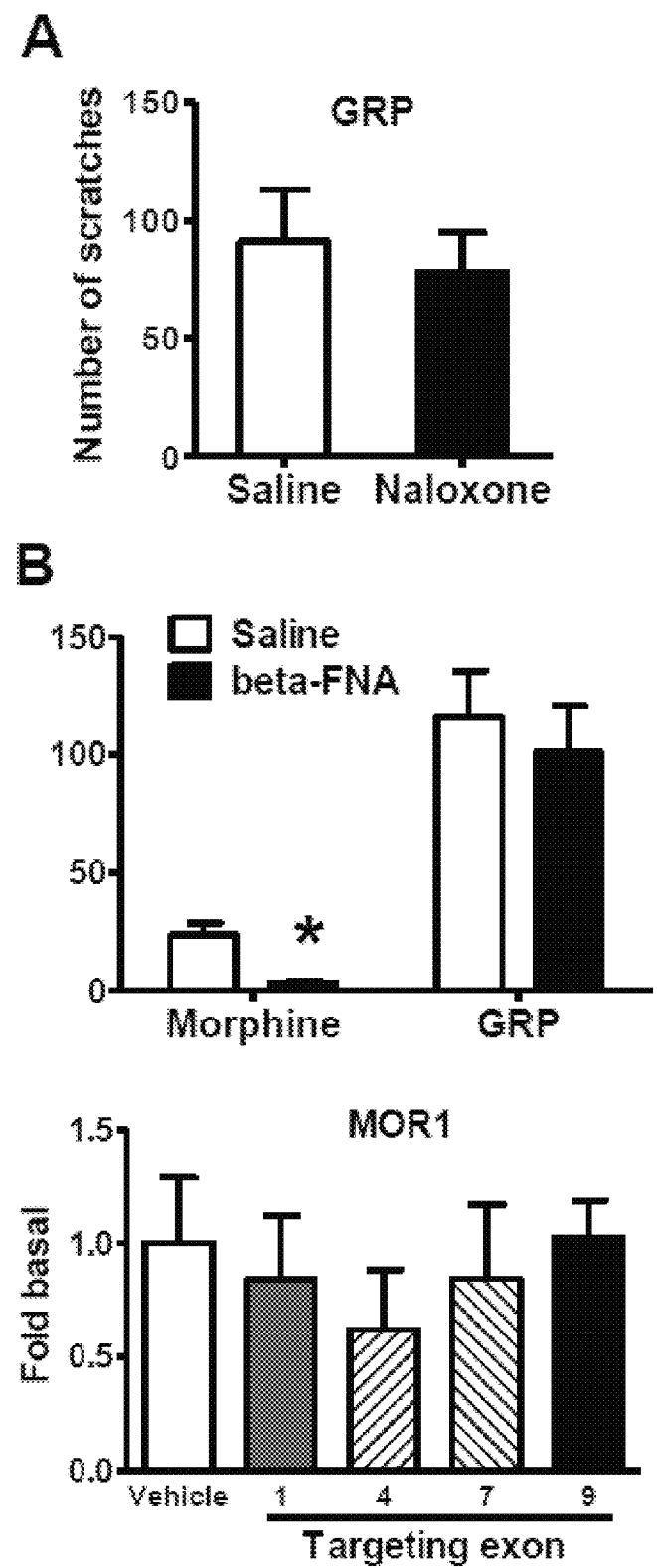
Figure 3:
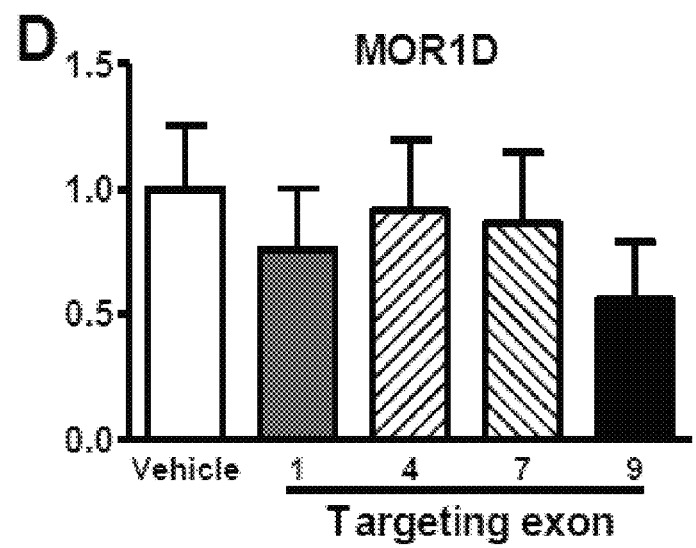
Figure 3:
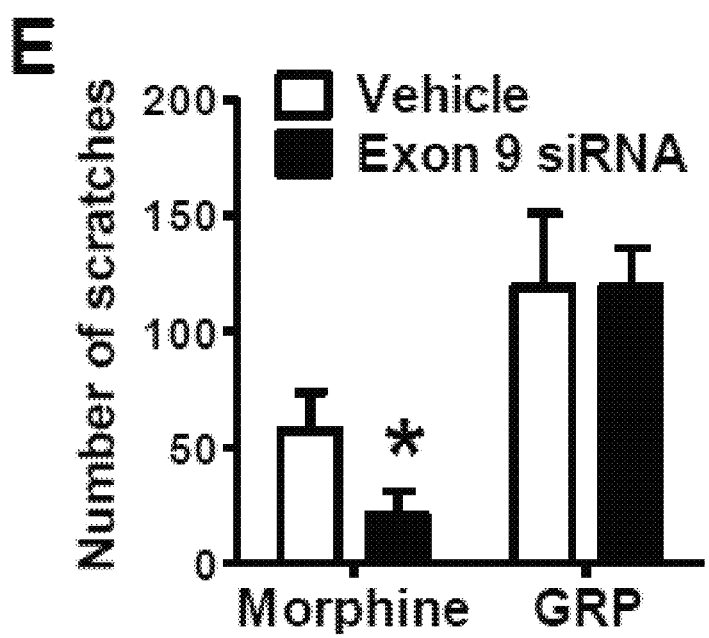

FIG. 3 MOR siRNA were Specific for Spinal MOR mRNA. (A) GIS was not significantly affected by naloxone (3 mg/kg, s.c.). n=6. (B) MIS, but not GIS, was significantly blocked by beta-FNA. n=6. *p<0.05. (C and D) Expression of MOR1D (C) or MOR1 (D) in DRG was not significantly affected by i.t. siRNA injection. n=5. (E) MOR exon 9 siRNA knockdown blocked MIS. GIS behavior was not affected by exon 9 siRNA. n=6. *p<0.05. Error bars represent standard error.

Figure 4:
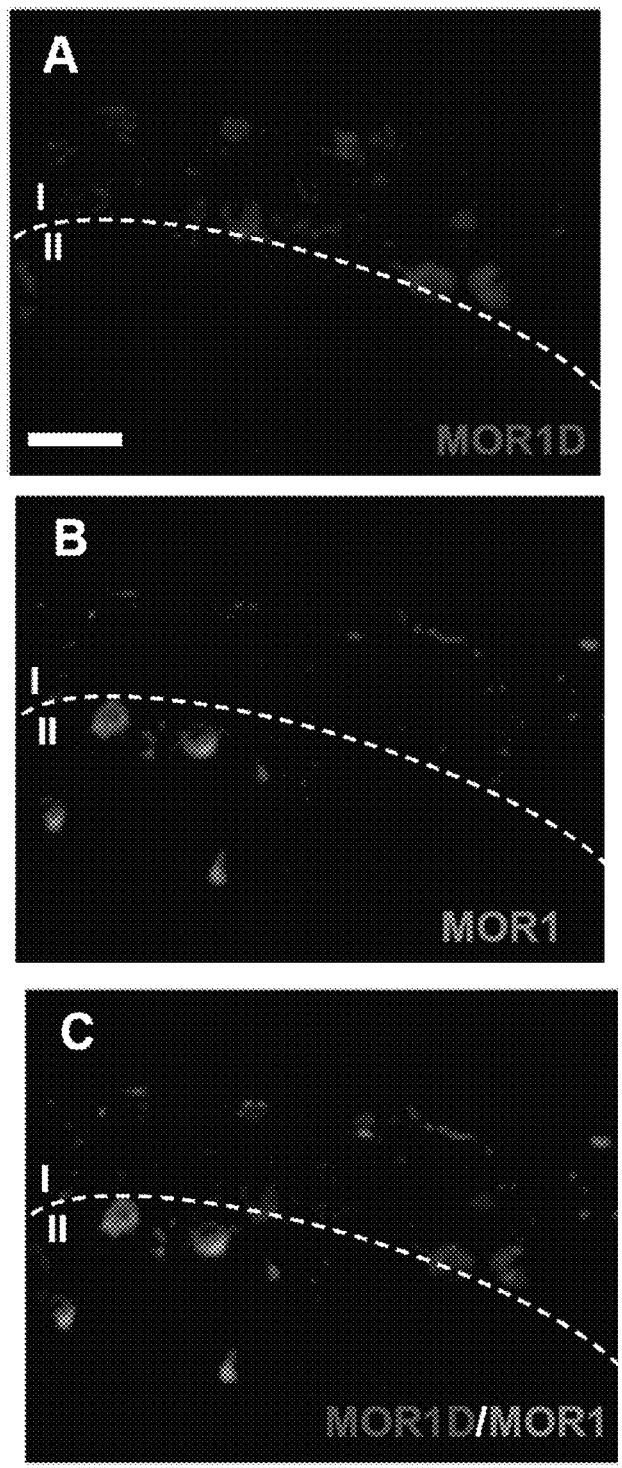
Figure 4:
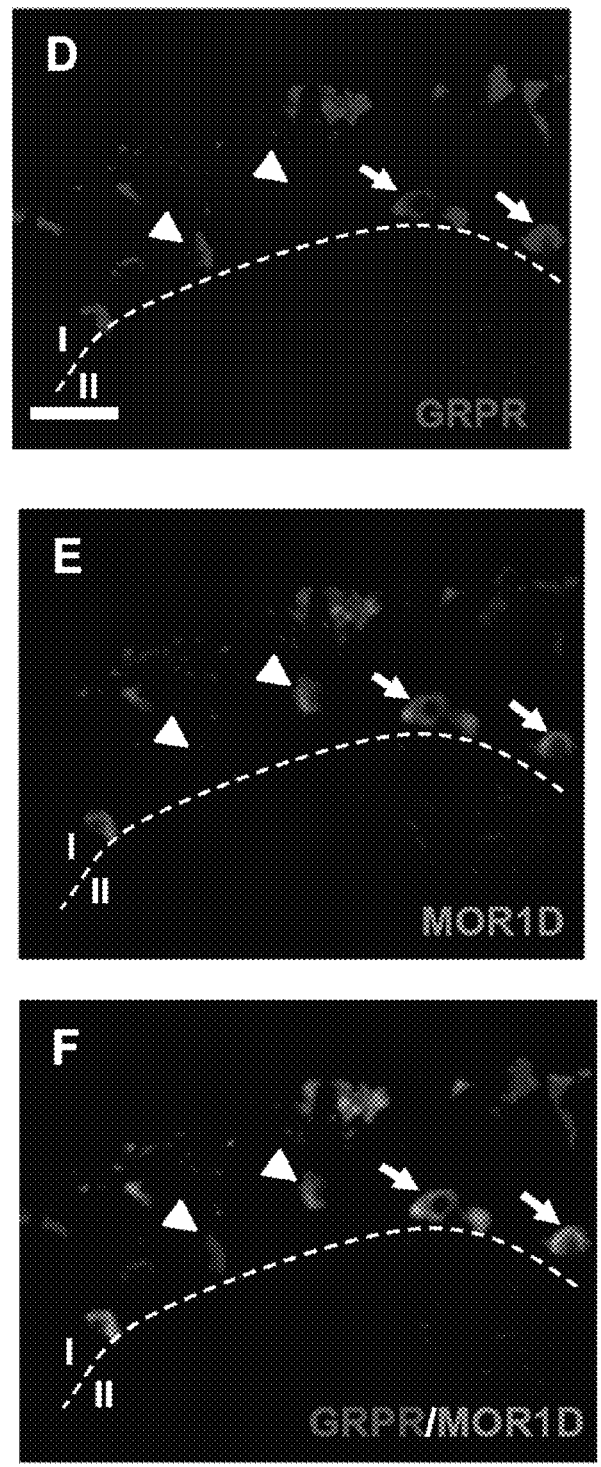
Figure 4:
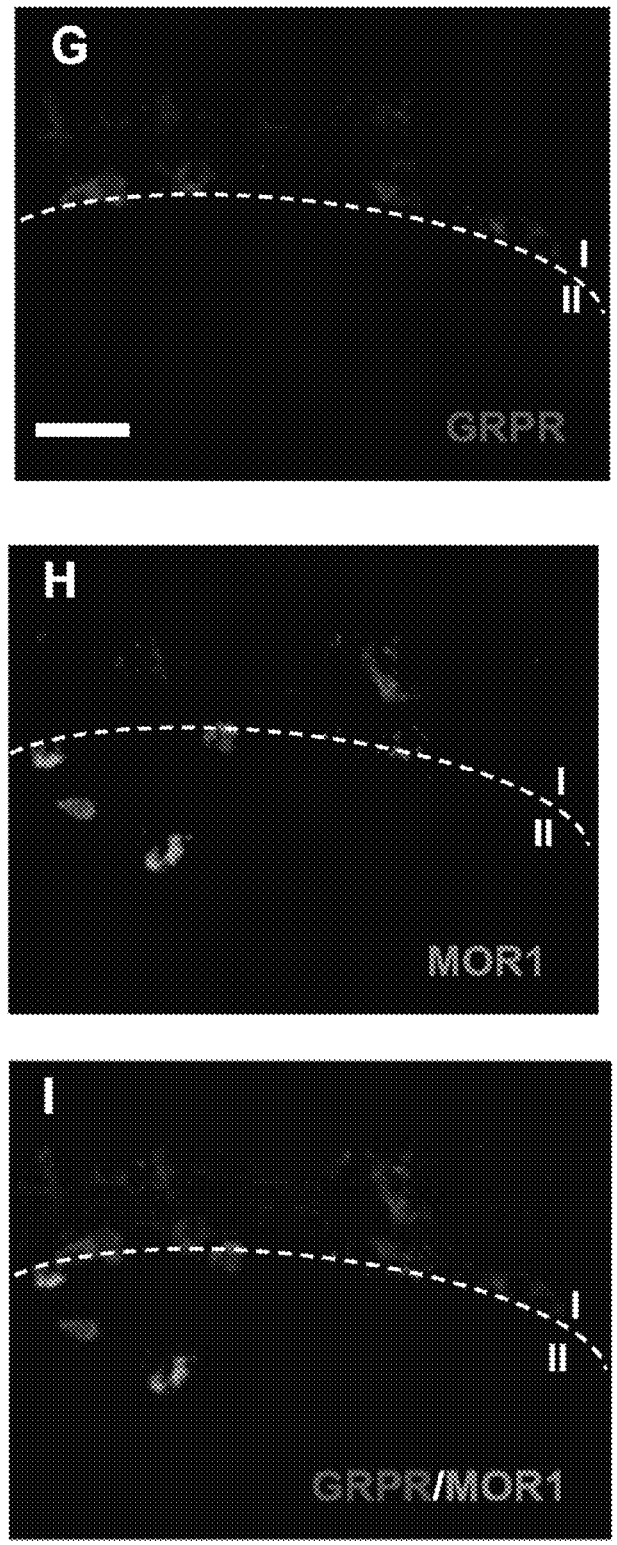

FIG. 4 Co-Expression of GRPR and MOR1D in Lamina I of the Spinal Cord. (A-C) Double immunostaining revealed no co-localization of MOR1D (red, lamina I) and MOR1 (green, lamina II) in the spinal cord. (D-F) Double immunostaining of GRPR (red) and MOR1D (green) in lamina I of the spinal cord. Arrows indicate co-expression (yellow) and arrowheads indicate singular expression. Cells co-expressing GRPR (11/33) and MOR1D (11/17), which represent ~31% of GRPR-positive cells and ~65% of MOR1D-positive cells respectively, were found in 25 lumbar spinal cord sections. (G-I) Double immunostaining revealed no co-localization of GRPR (red, lamina I) and MOR1 (green, lamina II) in the dorsal spinal cord. Scale bar, 50 μm.

Figure 5:
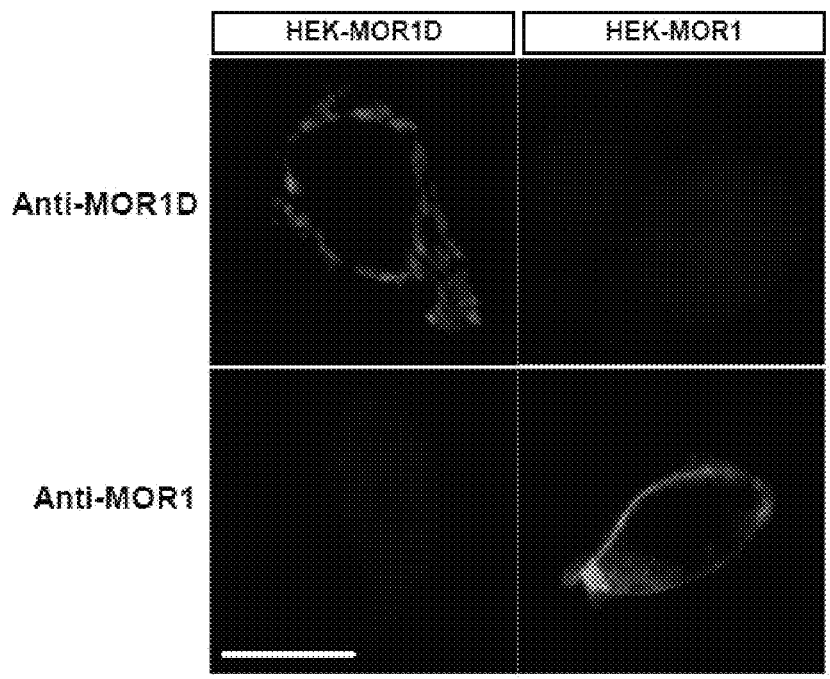
Figure 5:
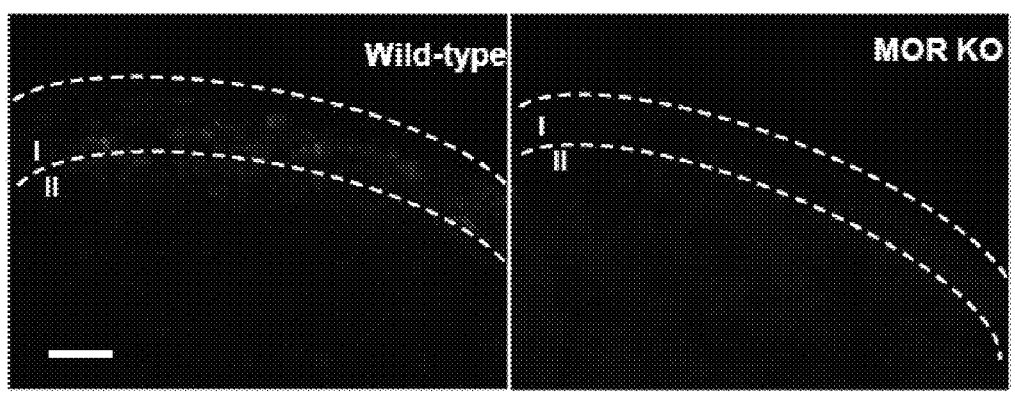

FIG. 5 Rabbit anti-MOR1D is Specific. (A) Rabbit anti-MOR1D antibody specifically labeled membrane MOR1D in HEK 293 cells expressing MOR1D. No cross activity with HEK 293 cells expressing MOR1 is present. Similarly, guinea pig anti-MOR1 antibody is specific to MOR1 and no cross activity to MOR1D is present. Scale bar is 20 μm. (B) Rabbit anti-MOR1D showed specific signals in the superficial dorsal horn of a wild-type mouse but not of a MOR KO mouse. The Lamina I and Lamina II of the superficial dorsal horn is indicated by the dashed lines and the "I" and "II", respectively. Scale bar is 100 μm.

Figure 6:
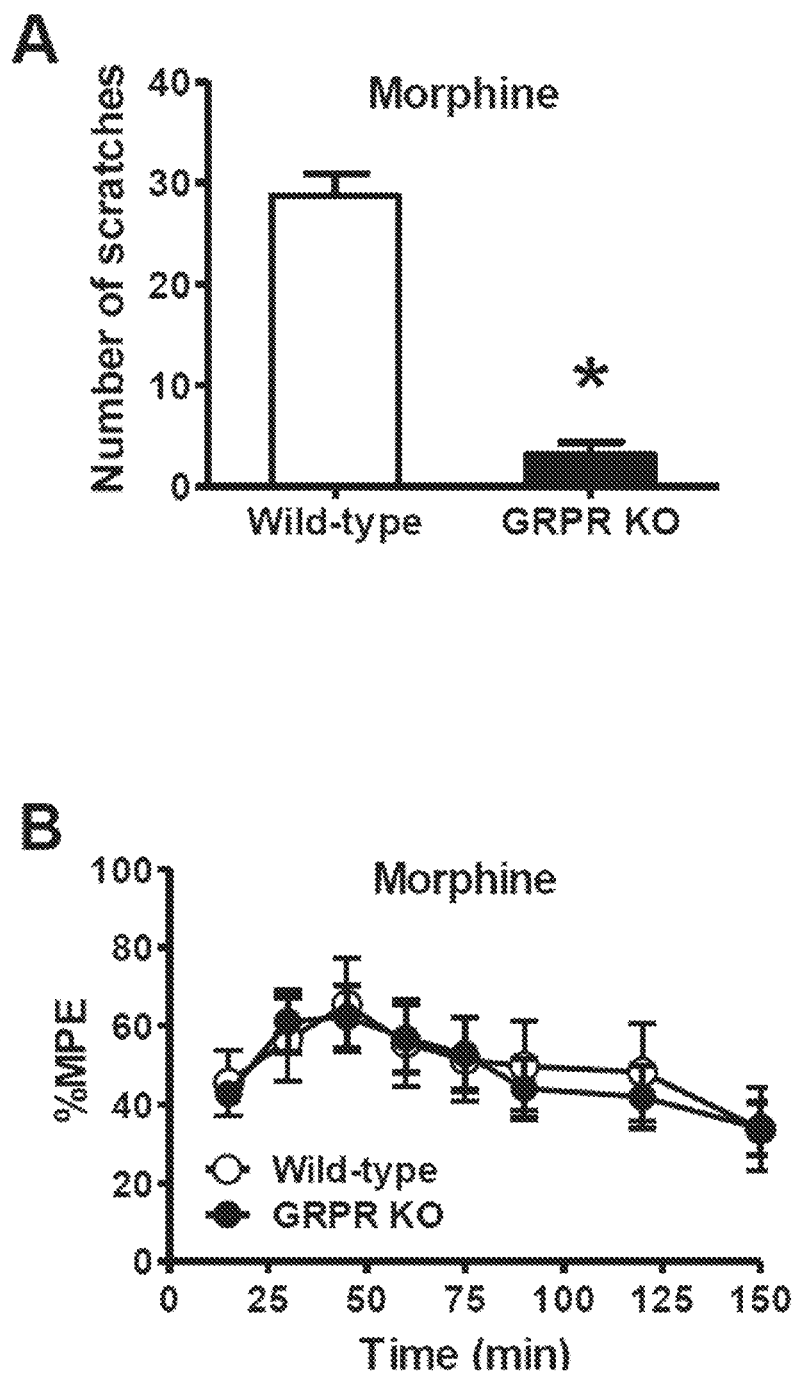
Figure 6:
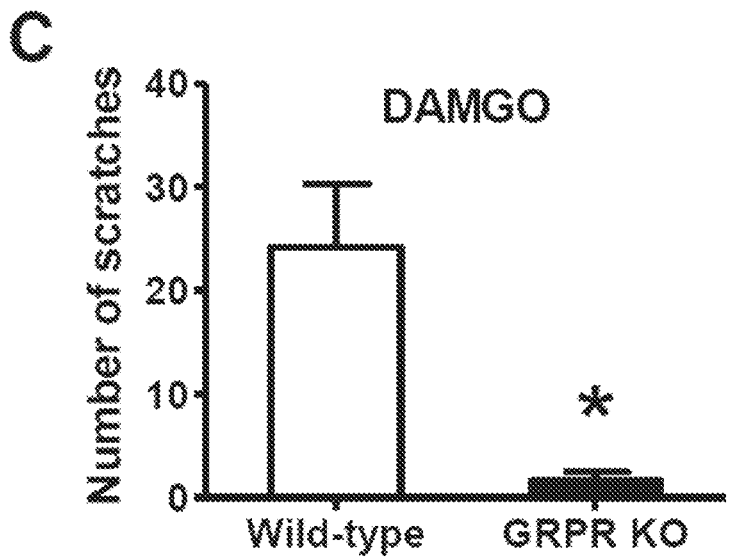
Figure 6:
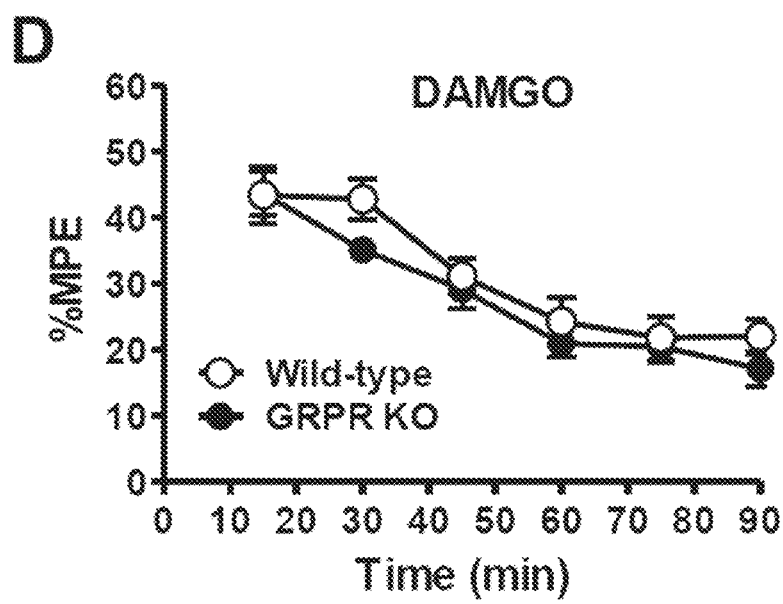
Figure 6:
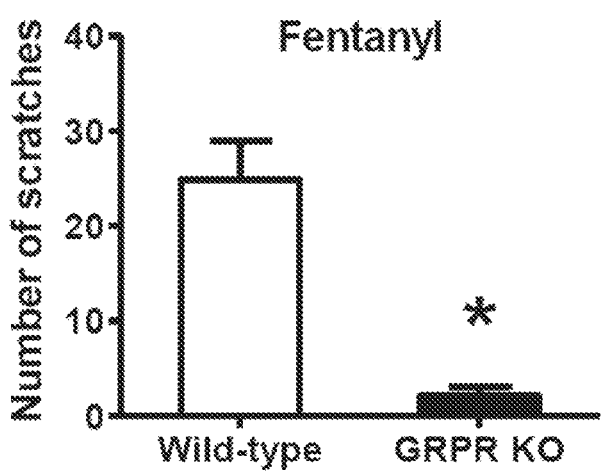
Figure 6:
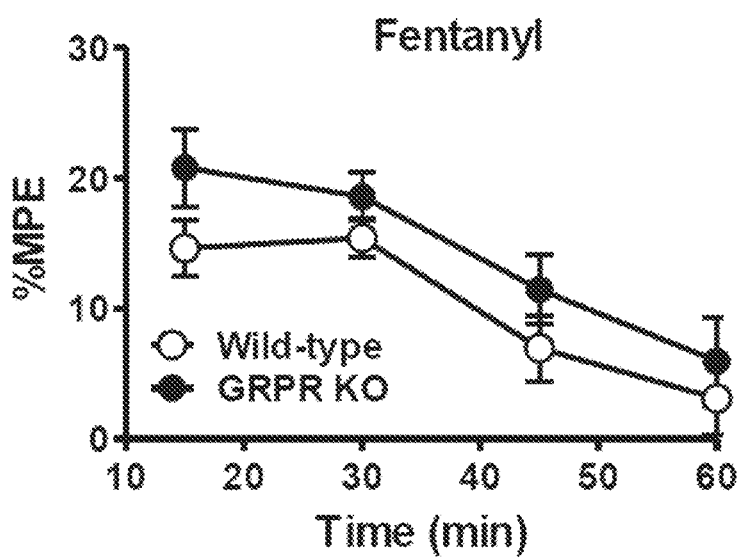
Figure 6:
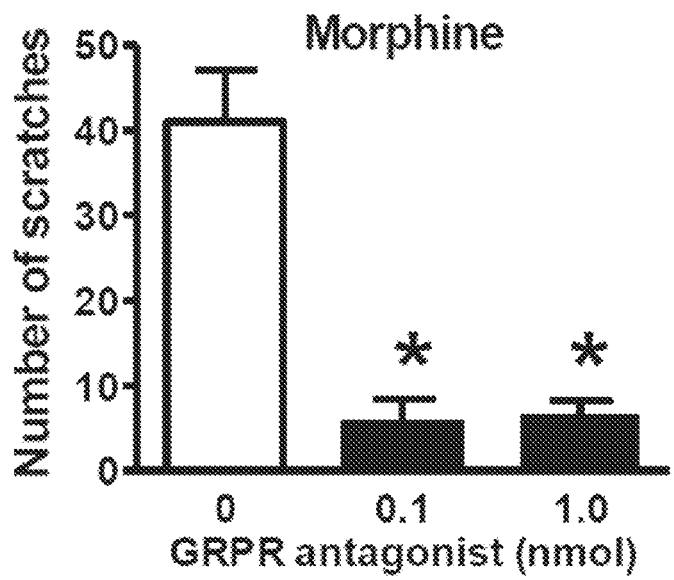
Figure 6:
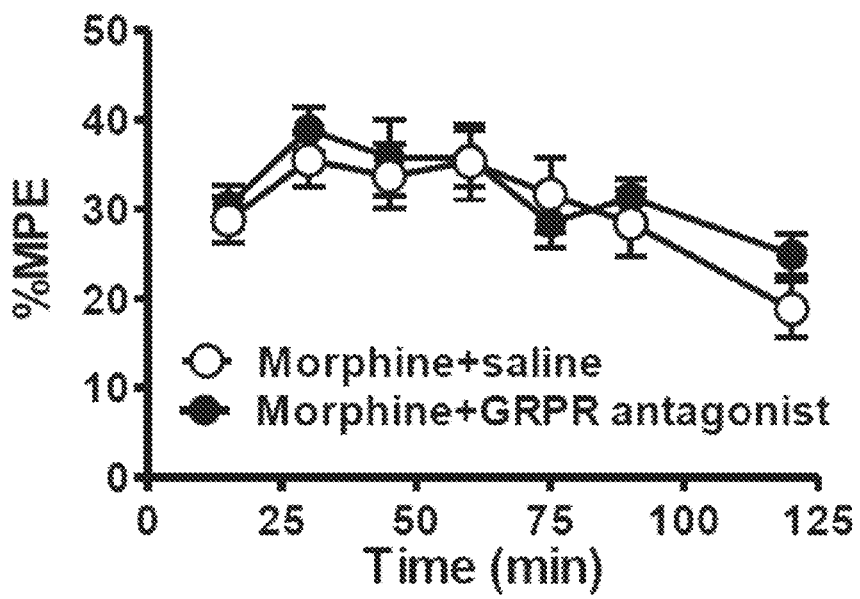

FIG. 6 GRPR is Important for Opioid-Induced Scratching Behavior. (A) MIS was nearly abolished in GRPR KO mice compared with wild-type littermate mice. *p<0.05. (B) MIA is comparable between GRPR KO and wild-type littermates. (C) Scratching behavior induced by i.t. DAMGO (0.02 nmol) was significantly reduced in GRPR KO mice. *p<0.05. (D) Analgesic effect of i.t. DAMGO (0.02 nmol) is comparable between GRPR KO and wild-type littermates. (E and F) Scratching behavior induced by i.t. fentanyl was significantly reduced in GRPR KO mice (E), while the analgesic effect of fentanyl was not affected (F). *p<0.05. (G) MIS was significantly inhibited by co-injection with the GRPR antagonist (0.1, 1 nmol). *p<0.05. (H) MIA was not significantly affected by co-injection of the GRPR antagonist (1.0 nmol). In all experiments, the dose of i.t. morphine is 0.3 nmol. n=6~9 per group. Error bars represent standard error of the mean. See also FIG. 7.

Figure 7:
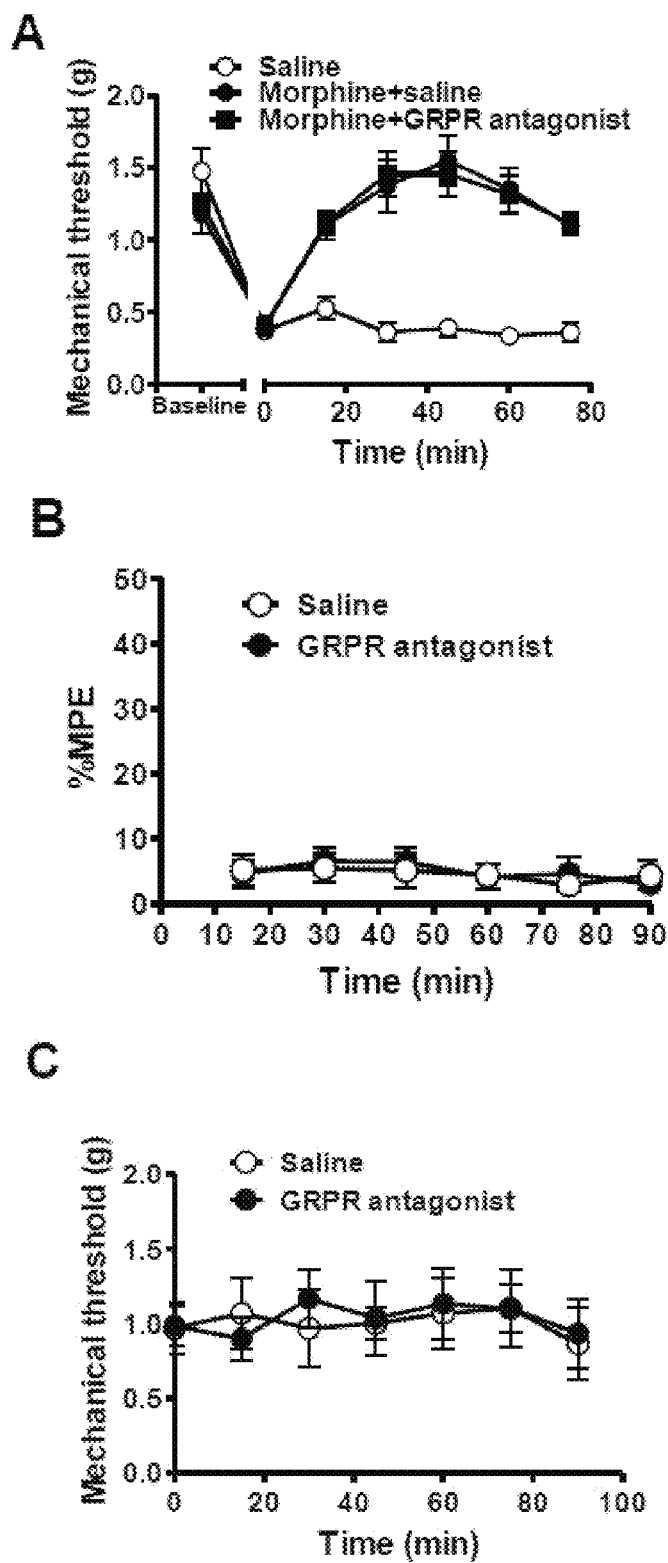

FIG. 7 GRPR is not Required for MIA and MOR is not Involved in GPR-Induced Scratching. (A) Mechanical threshold was tested before and 24 hr after intraplantar injection of CFA (20 μl). Saline, morphine or morphine together with the GRPR antagonist was injected intrathecally and mechanical threshold was measured 24 hr after CFA, then the mechanical threshold was assessed every 15 min for 75 min. i.t. morphine significantly increased mechanical threshold in CFA-treated mice (p<0.01). Analgesic effect of intrathecal morphine (0.3 nmol) in CFA model was not significantly affected by co-injection of the GRPR antagonist (1.0 nmol). n=7~8. CFA, Complete Freund's adjuvant. (B and C) i.t. injection of the GRPR antagonist did not significantly affect the acute pain tested by tail immersion assay (B) and von Frey (C). n=6. Error bars represent standard error of mean.

Figure 8:
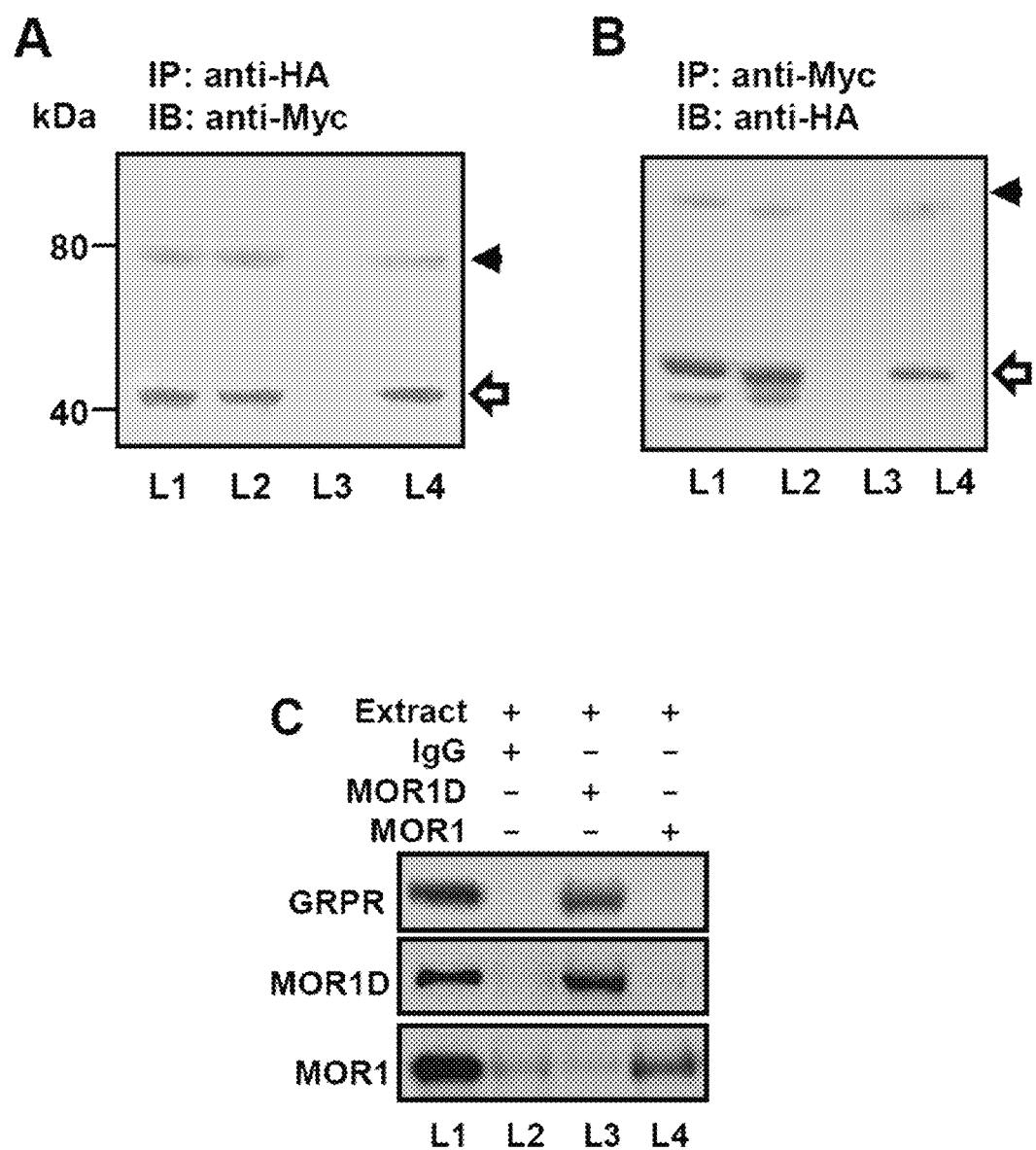
Figure 8:
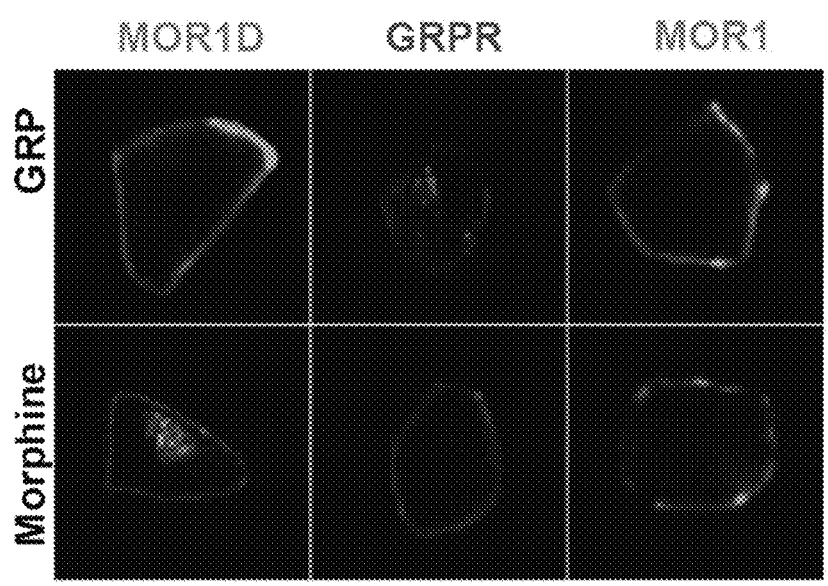
Figure 8:
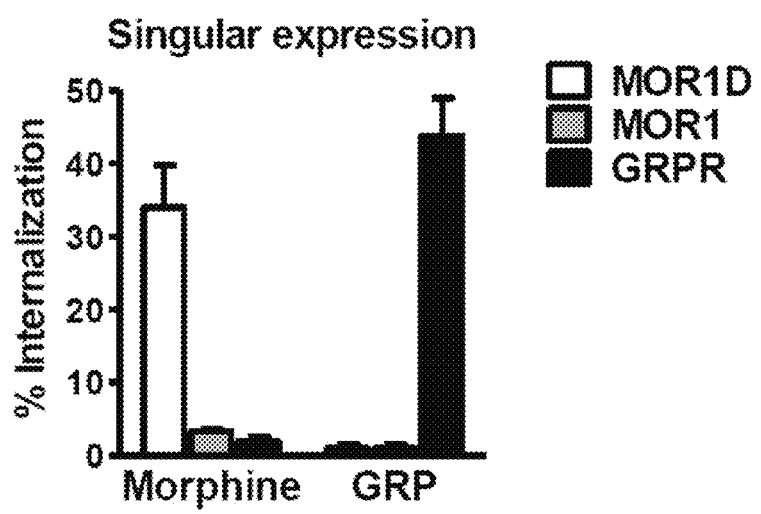
Figure 8:
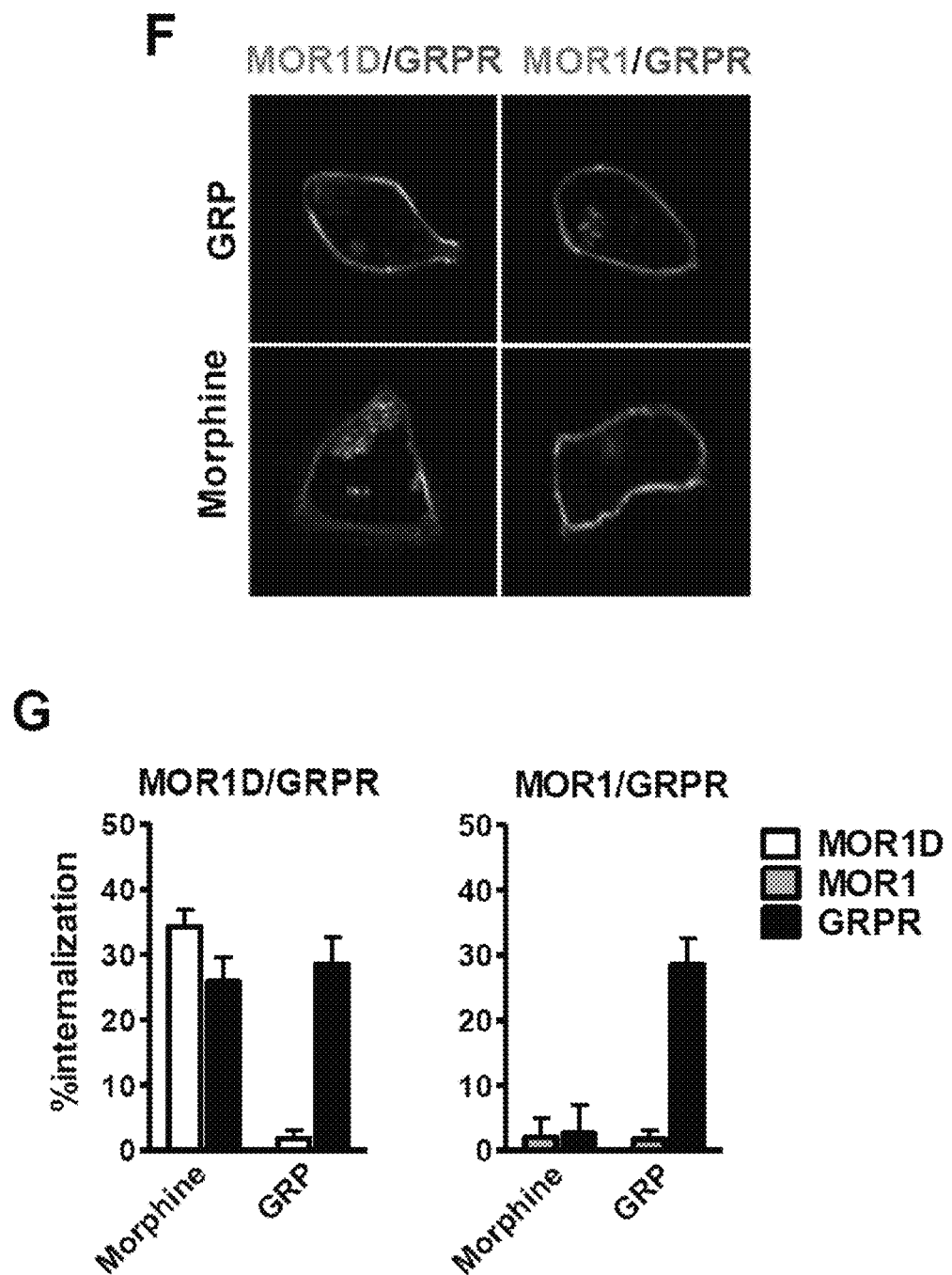
Figure 8:
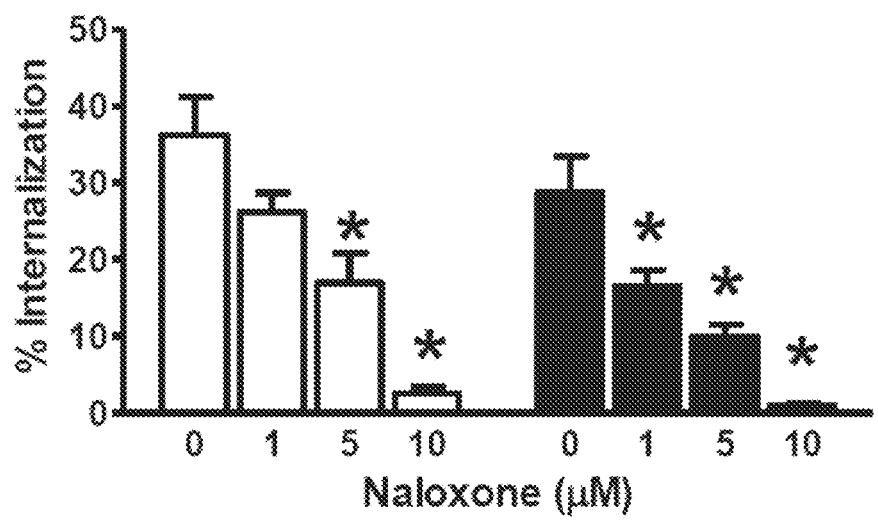
Figure 8:
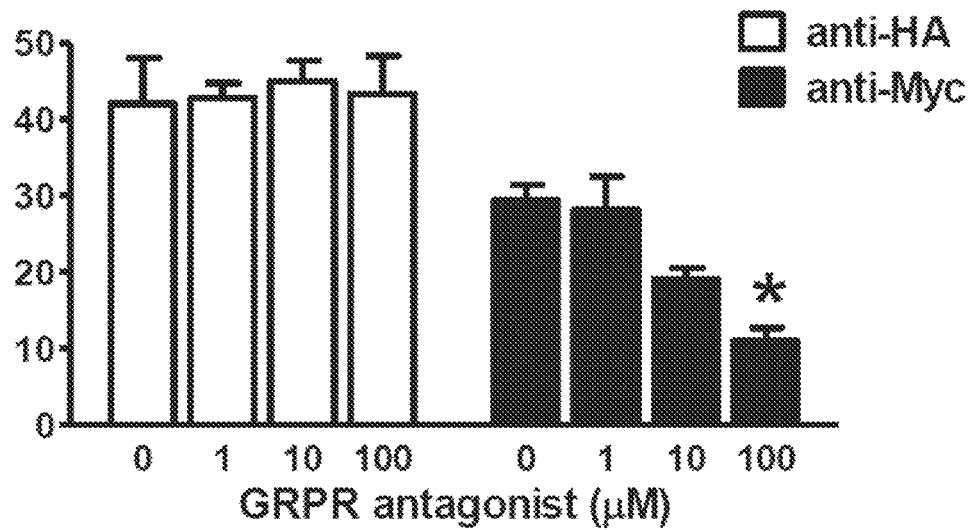

FIG. 8 Co-Immunoprecipitation and Co-Internalization of GRPR and MOR1D. (A) Myc-GRPR (43 kDa) was detected in membrane fraction of MOR1/GRPR cells (L1) and MOR1D/GRPR cells (L2). Anti-HA antibody co-precipitated Myc-GRPR from MOR1D/GRPR cells (L4), but not from MOR1/GRPR cells (L3). (B) Expression of HA-MOR1 (44 kDa) in HA-MOR1/Myc-GRPR cells (L1) and expression of HA-MOR1D (44 kDa) in HA-MOR1D/Myc-GRPR cells (L2) were revealed by anti-HA immunoblotting. An HA-MOR1D band (44 kDa) was precipitated by anti-Myc antibody from HA-MOR1D/Myc-GRPR cells (L4). Anti-Myc antibody failed to precipitate HA-MOR1 from cells expressing both Myc-GRPR and HA-MOR1 (L3). IP: immunoprecipitaion, IB: immunoblotting, kDa: kilodalton. (C) GRPR, MOR1D and MOR1 were detected in the membrane extract of dorsal horn (L1). GRPR was co-precipitated by anti-MOR1D (L3) but not by anti-MOR1 (L4) or irrelevant IgG (L2). (D and E) Immunostaining (D) and ELISA (E) revealed endocytosis of HA-MOR1D but not HA-MOR1 or Myc-GRPR upon morphine treatment, while GRP induced endocytosis of GRPR but not MOR1D or MOR1. (F and G) Immunostaining (F) and ELISA (G) revealed that Myc-GRPR, when co-expressed with HA-MOR1D but not HA-MOR1, internalized upon morphine stimulation. (H) Naloxone dose-dependently blocked morphine-induced internalization of Myc-GRPR and HA-MOR1D. (I) The GRPR antagonist blocked morphine-induced internalization of Myc-GRPR, but not HA-MOR1D. Data are expressed as mean and standard error of three independent experiments. Error bars represent standard error of the mean. *p<0.05. See also FIG. 9.

Figure 9:
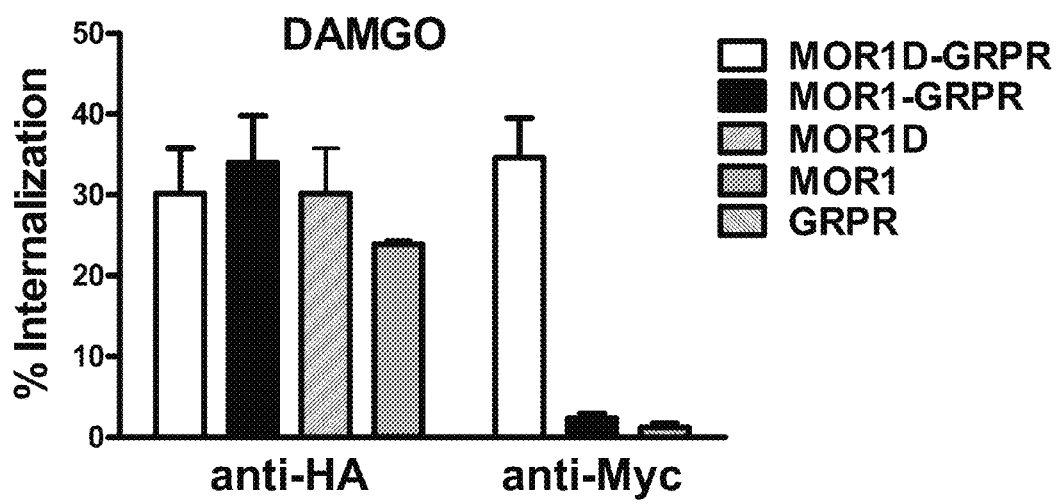

FIG. 9 DAMGO Induced GRPR Internalization through MOR1D. Both MOR1D and MOR1 can be internalized by DAMGO (1 μM), whether co-expressed with GRPR in HEK 293 cells or not. GRPR can be internalized by DAMGO when co-expressed with MOR1D, but not with MOR1. DAMGO cannot internalize GRPR in GRPR singular expressing HEK 293 cells.

Figure 10A:
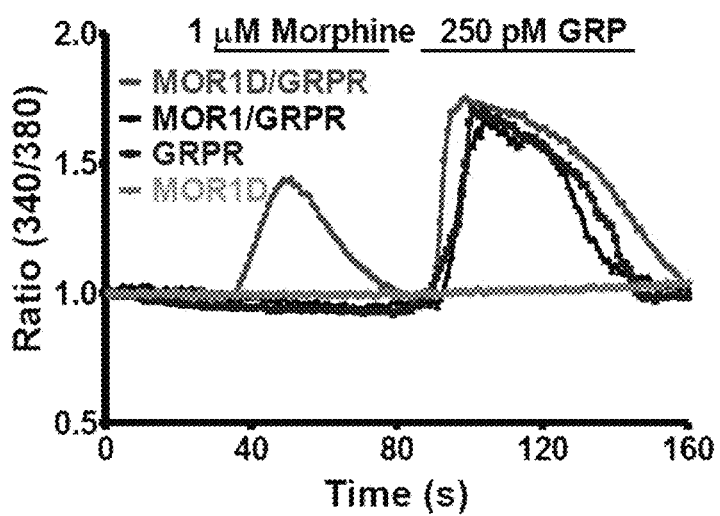
Figure 10:
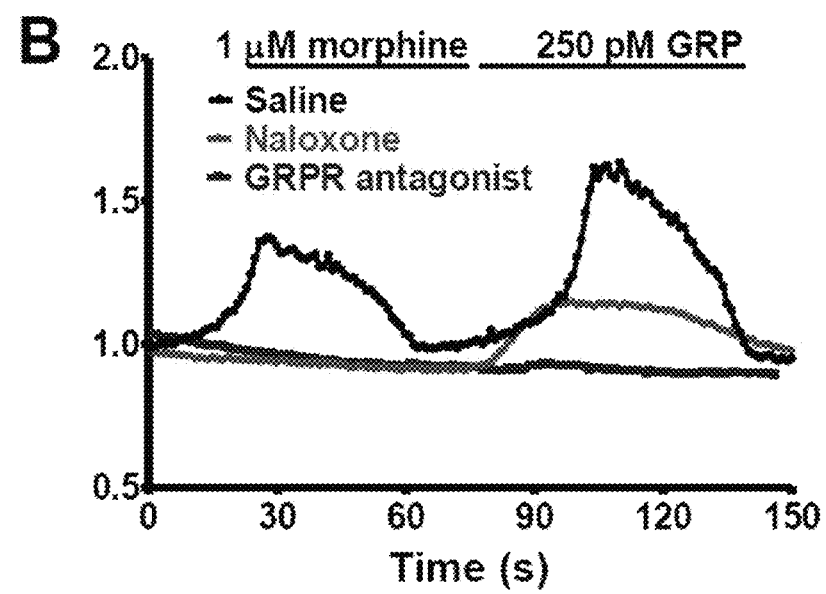
Figure 10:
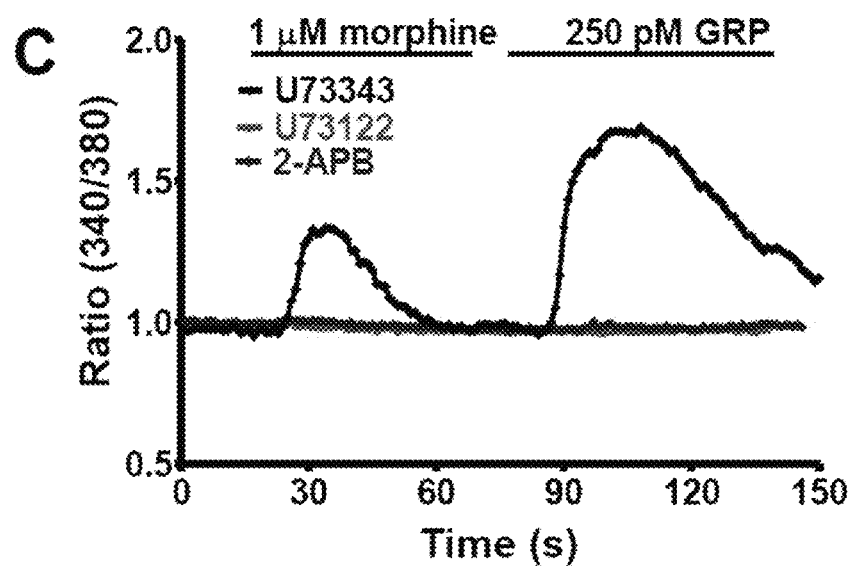
Figure 10:
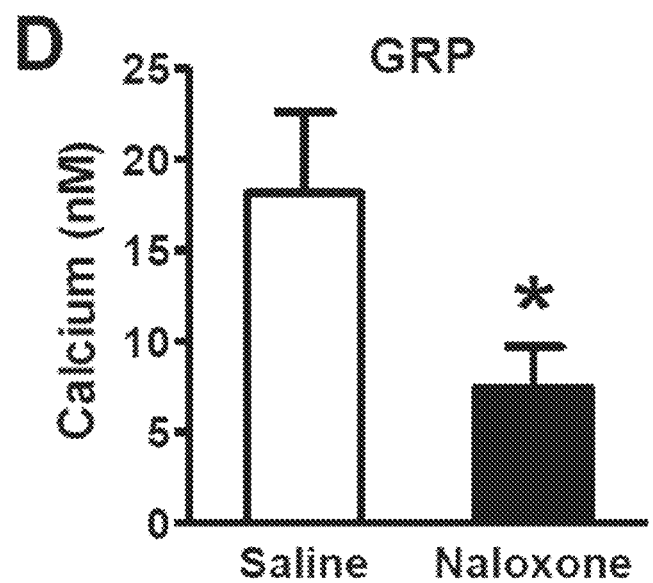
Figure 10:
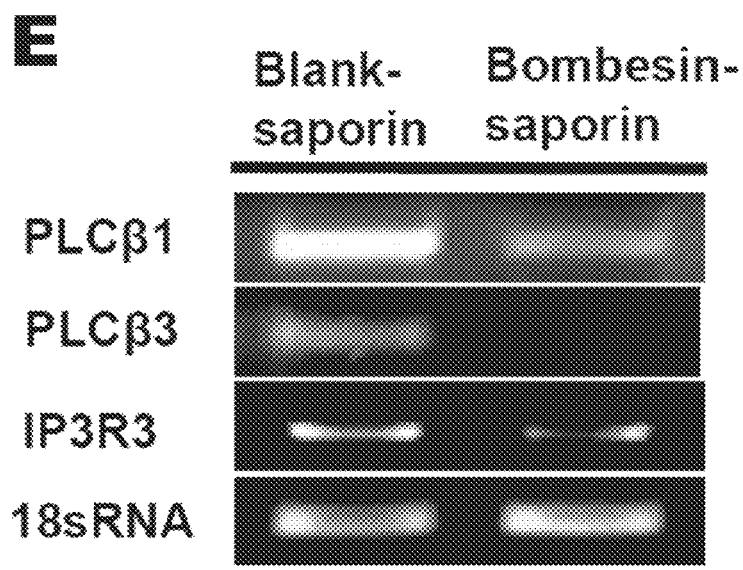
Figure 10:
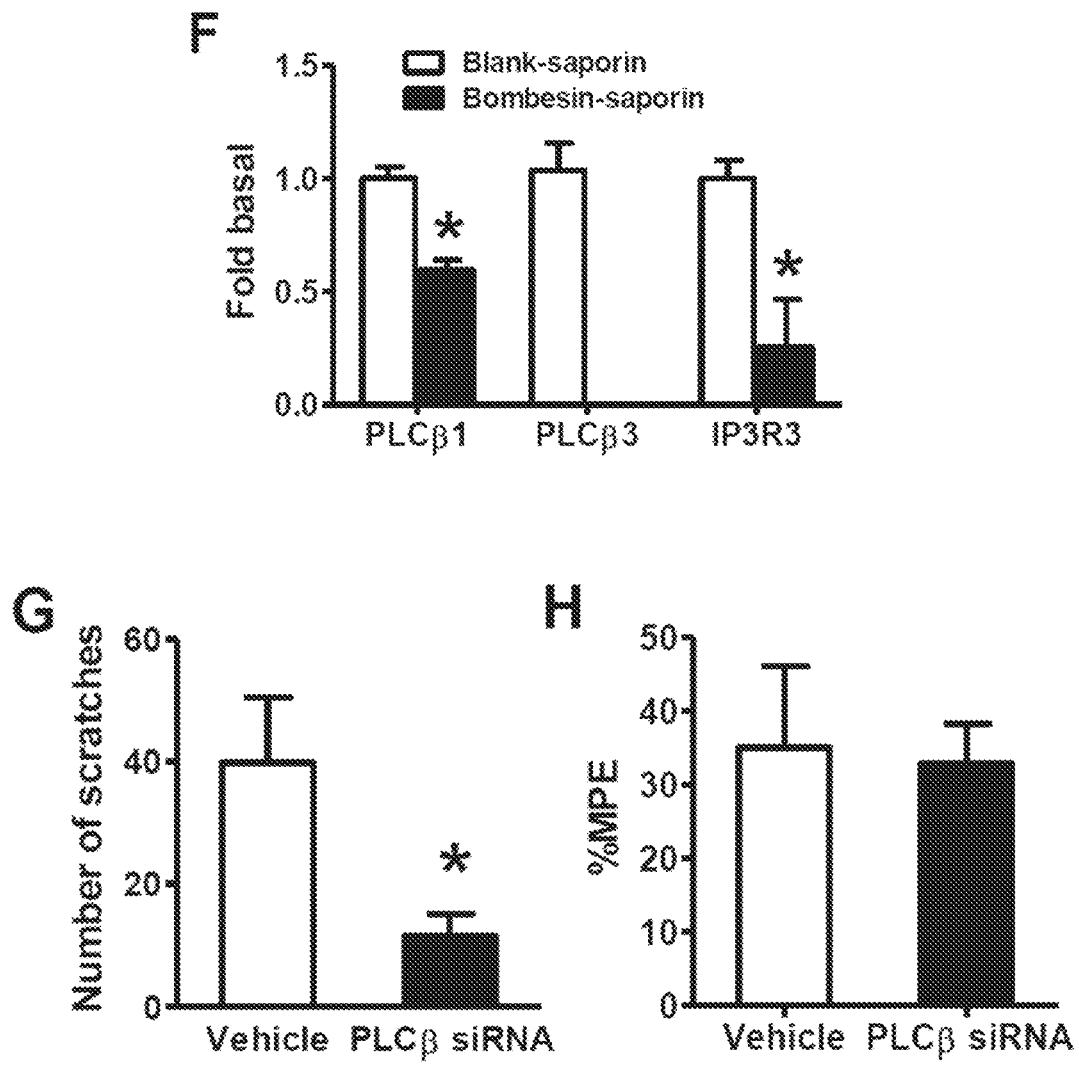
Figure 10:
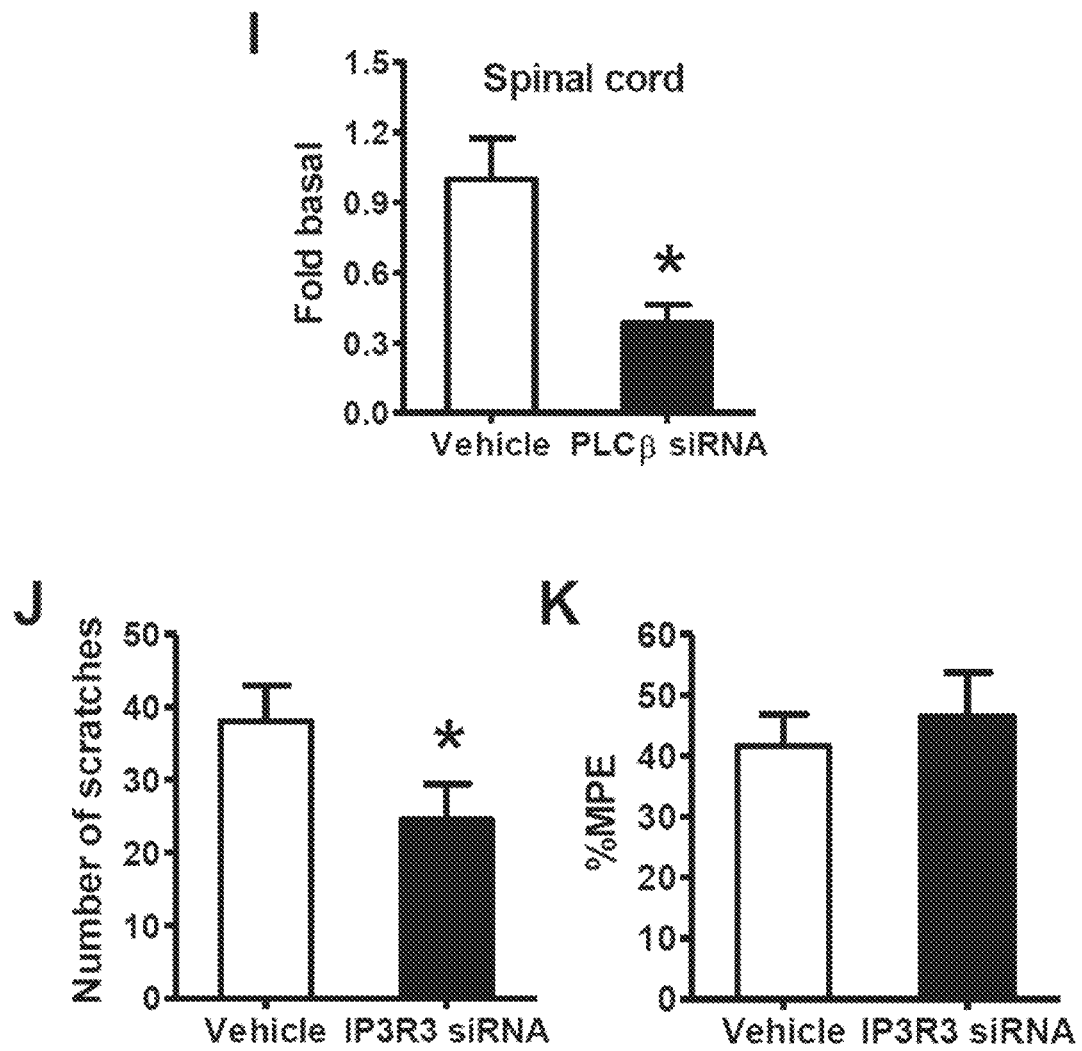

FIG. 10 Cross Activation of the GRPR Signal Transduction Pathway by MOR1D in Response to Morphine. The responses of HEK 293 cells expressing vary receptors to morphine or GRP were tested using calcium imaging. (A) HEK 293 cells co-expressing MOR1D and GRPR showed calcium response to both morphine and GRP. Cells co-expressing MOR1D and GRPR were unable to respond to morphine, whereas they responded to GRP. (B) The GRPR antagonist completely blocked morphine and GRP-induced Ca2+ increase in cells co-expressing MOR1D and GRPR. Naloxone blocked morphine- and reduced GRP-induced Ca2+ response in cells co-expressing MOR1D and GRPR. (C) Both PLC inhibitor U73122 and IP3 receptor antagonist 2-APB blocked the response to morphine and GRP in cells co-expressing MOR1D and GRPR. U73343, an inactive structural analog of U73122 had no effect on morphine- or GRP-evoked Ca2+ increase. (D) Quantified data comparing peak intracellular calcium concentration. Naloxone significantly reduced GRP-induced [Ca2+]i increase in cells co-expressing MOR1D and GRPR. n=3, *p<0.05. (E and F) GRPR+ cells in superficial dorsal horn were ablated by bombesin-saporin. The superficial dorsal horn was dissected for qRT-PCR. Gel image (E) and quantitative analysis (F) showed that PLCβ3 mRNA was lost in bombesin-saporin-treated group. PLCβ1 and IP3R3 mRNA were significantly decreased by bombesin-saporin treatment. (G) Two days after the last injection of PLCβ siRNA (1.25 μg, i.t.), MIS was significantly reduced. *p<0.05. (H) MIA was not significantly affected by PLCβ siRNA. (I) PLCβ mRNA level in the superficial dorsal horn was significantly reduced by i.t. injection of PLCβ siRNA. *p<0.05. (J) Two days after i.t. IP3R3 siRNA, MIS was significantly reduced. *p<0.05. (K) MIA was not affected by IP3R3 siRNA. (L) IP3R3 mRNA level in the superficial dorsal horn was significantly reduced by i.t. injection of IP3R3 siRNA. n=5. *p<0.05. In all experiments, n=6~7 per group. Error bars represent standard error of the mean. See also FIG. 11.

Figure 11A:
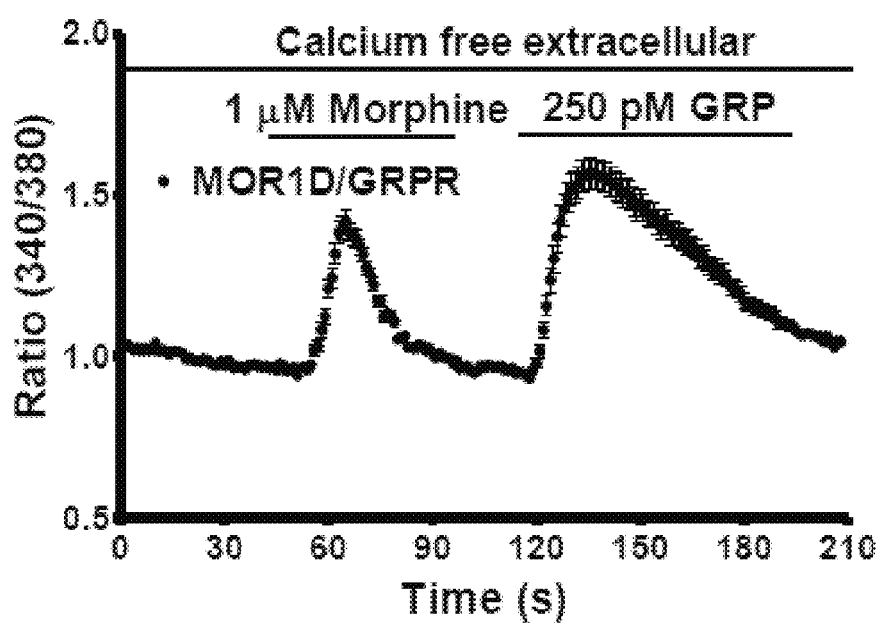
Figure 11:
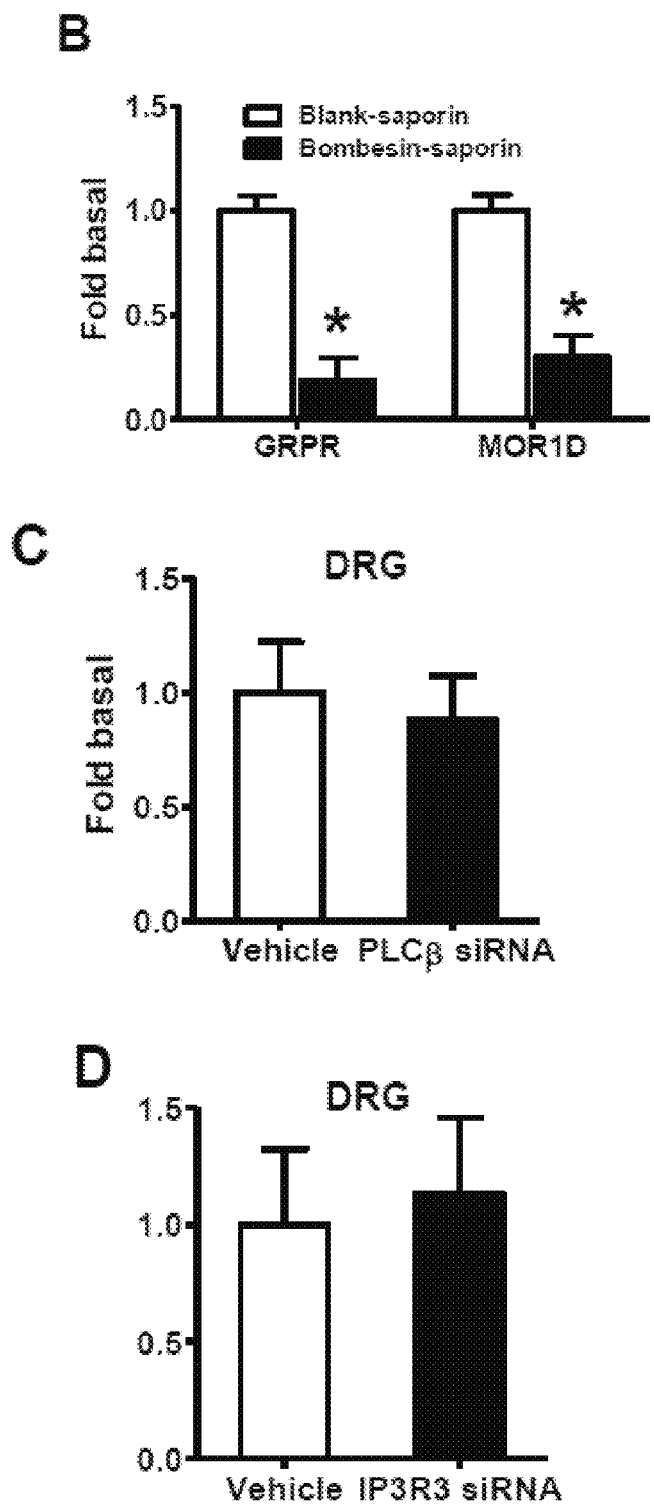
Figure 11:
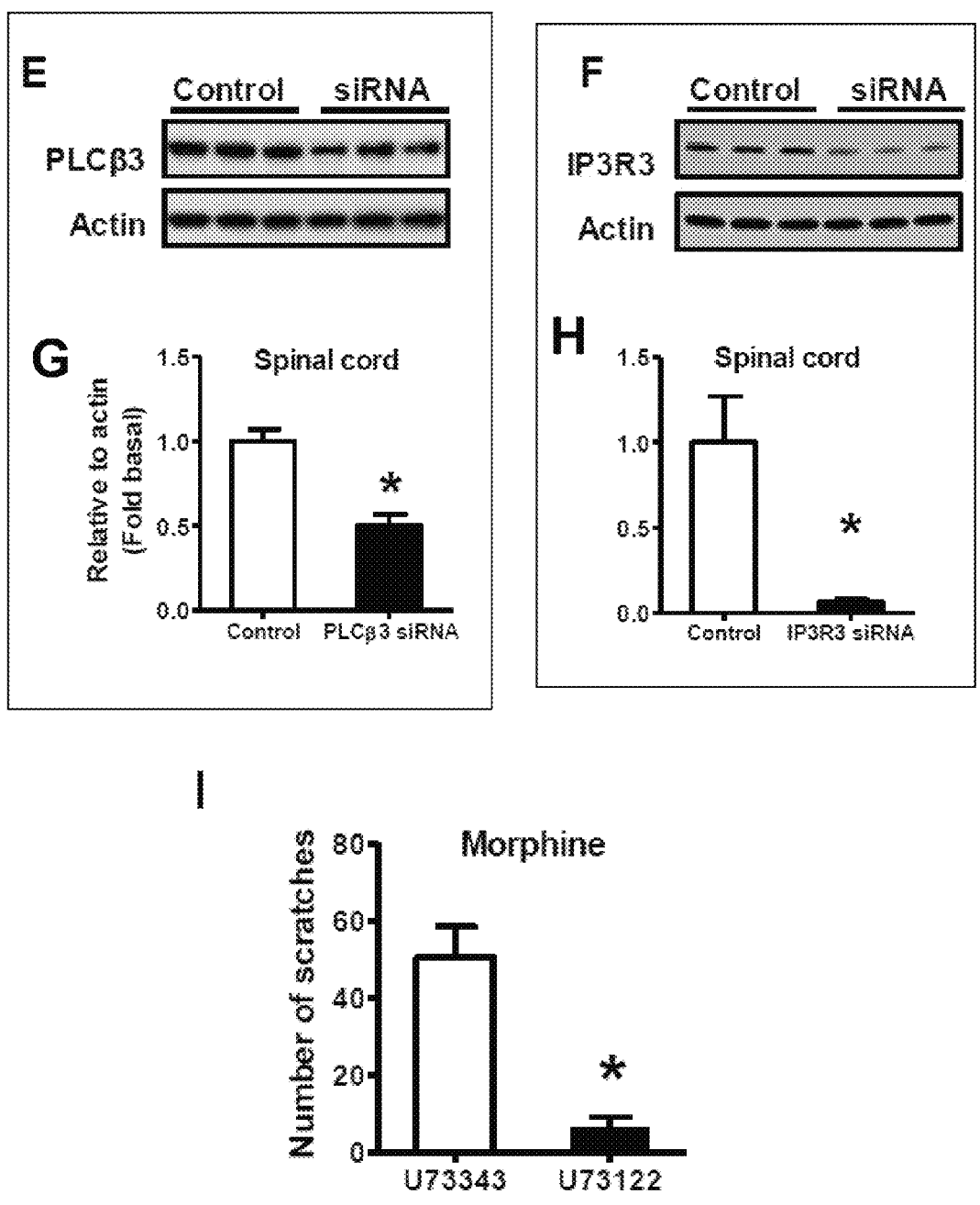
Figure 11:
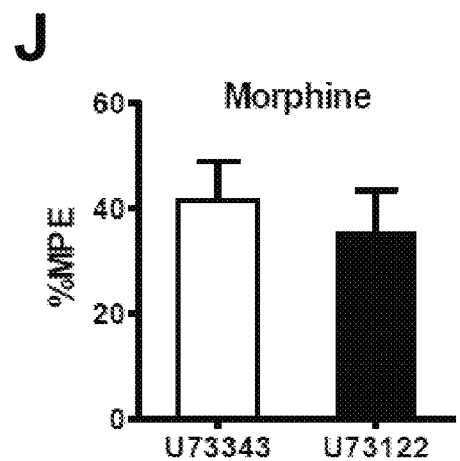
Figure 11:
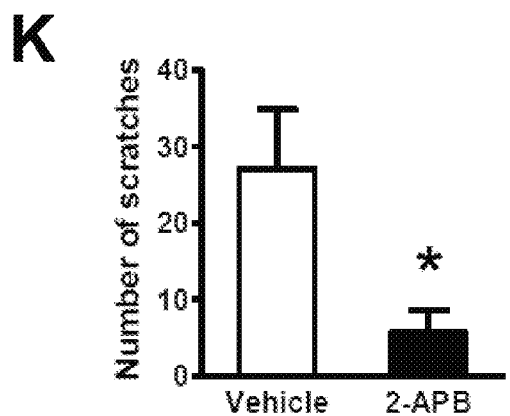
Figure 11:
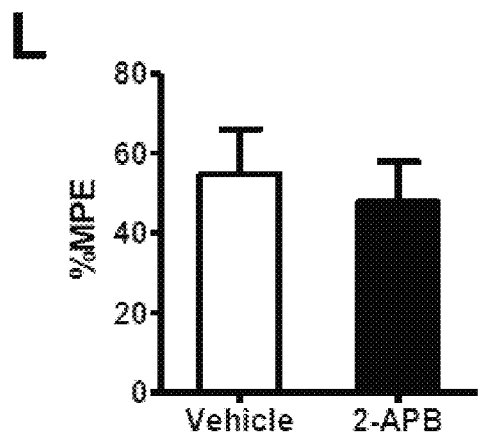

FIG. 11 Cross Activation of Spinal GRPR/PLC/IP3 Signaling Pathway is Important for MIS. (A) In calcium free extra-cellular buffer, both morphine and GRP induced calcium spikes in HEK 293 cells expressing MOR1D/GRPR. (B) GRPR+ cells in superficial dorsal horn were selectively ablated by bombesin-saporin. The superficial dorsal horn was dissected for qRT-PCR. The level of GRPR mRNA and MOR1D mRNA was significantly decreased by bombesin-saporin treatment. (C) PLCβ mRNA level in DRG neurons was not affected by i.t. injection of PLCβ1/β3 siRNA. n=5. (D) IP3R3 mRNA level in DRG neurons was not reduced by i.t. injection of IP3R3 siRNA. n=5.(E-H) Representative blots (E, F) and quantified data (G, H) show PLCβ3 (E, G) and IP3R3 (F, H) protein in spinal cord was significantly knocked down by PLCβ3 siRNA and IP3R3 siRNA, respectively. n=4, *p<0.05. (I) I.t. MIS was significantly reduced by pre-injection of U73122, a PLC inhibitor. n=6, *p<0.05. (J) Analgesic effect of intrathecal morphine tested by tail immersion assay was not significantly affected by U73122. n=6. (K and L) Co-injection of 2-APB, an IP3R antagonist significantly inhibited MIS (K), but not MIA (L) as tested by tail immersion assay. n=6, *p<0.05. Error bars represent standard error of the mean.

Figure 12:
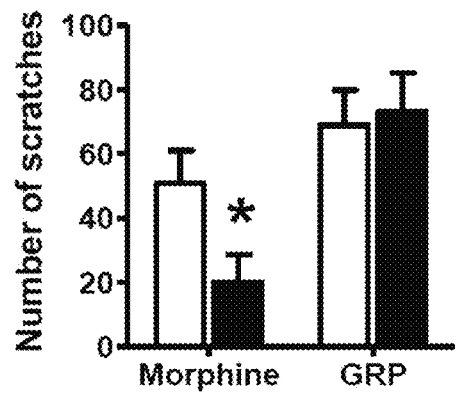
Figure 12:
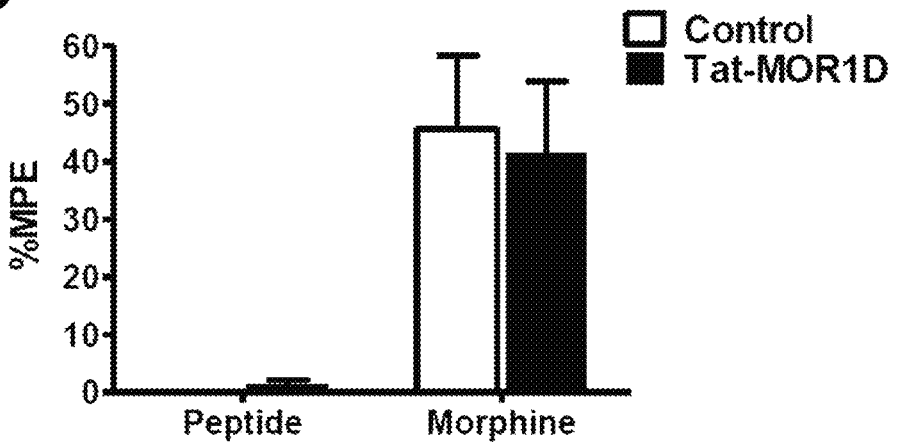
Figure 12:
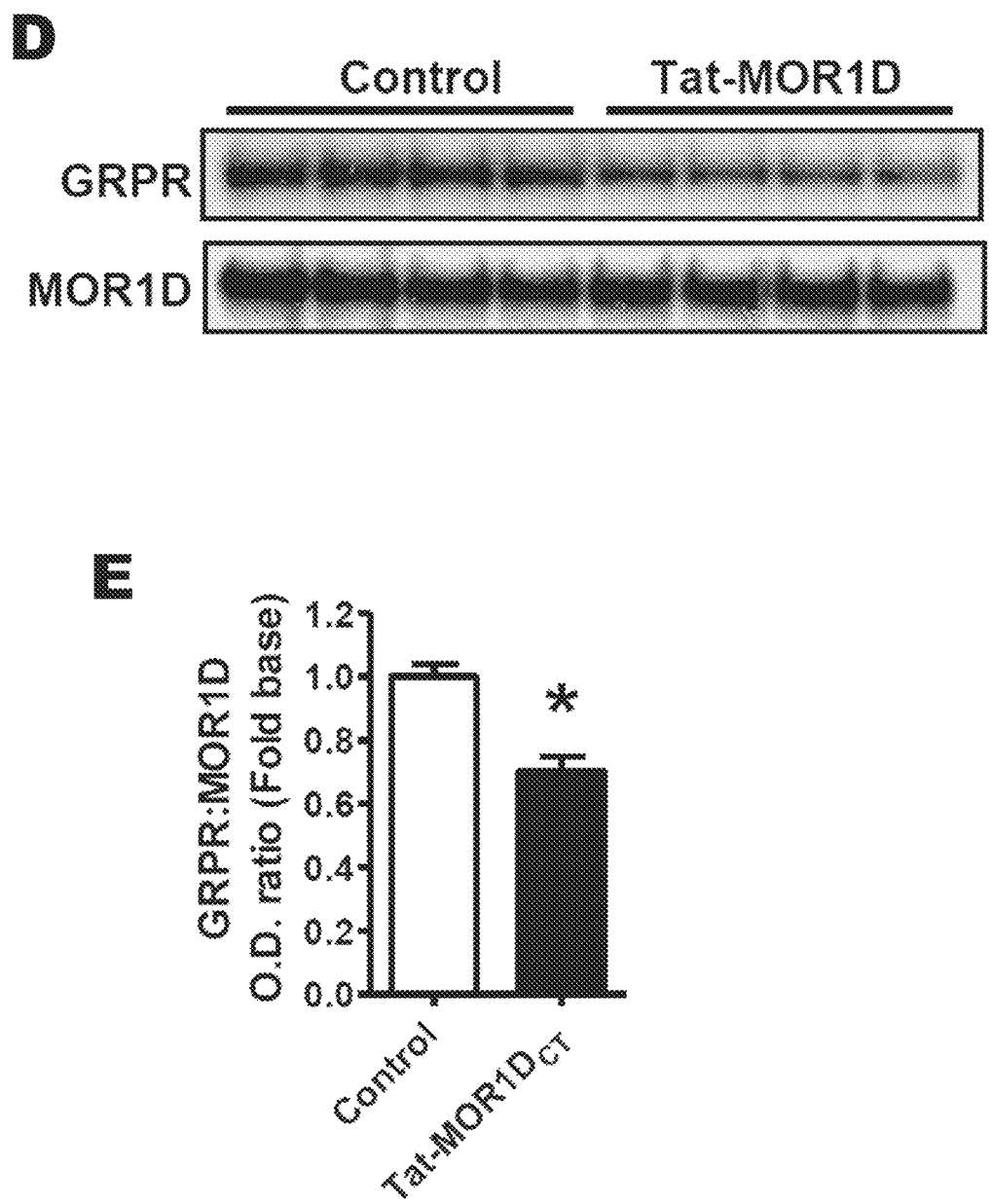

FIG. 12 MOR1D C-Terminus is Critical for MIS and MOR1D/GRPR Dimerization. (A) Sequence comparison of MOR1D and MOR1 reveals a unique motif in MOR1D C-terminus. Synthesized peptide Tat-MOR1DCT contains a Tat domain from human immunodeficiency virus-type 1 and the motif from MOR1DCT. Control peptide contains Tat domain and scrambled sequence of MOR1DCT. (B) Tat-MOR1DCT blocked MIS without affecting GIS. *p<0.05. (C) Tat-MOR1DCT had no effect on MIA. *p<0.05. (D and E) Co-IP by anti-MOR1D (D) and quantified O.D. ratio of GRPR and MOR1D (E) showing Tat-MOR1DCT decreased GRPR/MOR1D interaction in the lumbar spinal cord. In all experiments, n=6~8 per group. Error bars represent standard error of the mean.

FIG. 13 is the sequence of MOR1-2B (SEQ ID NO: 589), the human analog of MOR1D.

DETAILED DESCRIPTION OF THE INVENTION

The present invention provides methods and combinations for substantially inhibiting the opioid-induced internalization of GRPR in a pruritus specific neuron. As used herein, "pruritus specific neuron" refers to a neuron that expresses a pruritus specific receptor, is located in the central nervous system, and is responsible for transmitting the itch sensation. For instance, GRPR is a pruritus specific receptor, and neurons expressing GRPR in the dorsal horn are pruritus specific neurons. Generally speaking, a method of the invention comprises substantially inhibiting the interaction of GRPR with MOR1D and its analogs in other organisms, included, but not limited to MOR1-2B, the human analog. It is appreciated that the present invention is directed to analogs of MOR1D and MOR1-2B in other organisms and is not limited to the mouse and human analogs. Advantageously, substantially inhibiting the interaction of MOR1D or MORI-2B with GRPR provides a direct means of treating opioid-induced pruritus without compromising opioid analgesia. As a result, a method of the invention is advantageously used to reduce opioid-induced pruritus in a subject. The present invention also encompasses a combination comprising an agent to alleviate opioid-induced pruritus and at least one opioid analgesic.

I. Method of Inhibiting the Opioid-Induced Internalization of GRPR

One aspect of the present invention encompasses a method for substantially inhibiting the opioid-induced internalization of GRPR in a pruritus specific neuron. Generally speaking, the method comprises substantially inhibiting the interaction of GRPR with MOR1D (in mice) or MOR1-2B (in humans). Methods of measuring the internalization of GRPR are known in the art. Examples of these known techniques for measuring internalization of GRPR are illustrated in the examples section of the present application. Agents that inhibit the interaction of GRPR and MOR1D or MOR1-2B are described in detail below.

When administered to a subject, an agent that inhibits the interaction of GRPR and MOR1D or MOR1-2B may be used to alleviate opiate-induced pruritus. Methods of administering an agent that inhibits the interaction of GRPR and MOR1D or MOR1-2B are detailed below.

(a) Agents that Inhibit the Interaction of GRPR and MOR1D or MOR1-B2

In some embodiments, the interaction of GRPR with MOR1D or MOR1-B2 is inhibited by a MOR1D or MOR1-2B binding agent that inhibits interaction of GRPR and MOR1D or MOR1-2B, respectively. Methods of measuring the interaction of GRPR and MOR1D or MOR1-2B are known in the art. For instance, as detailed in the examples, immunoprecipitation may be used to determine interaction between GRPR and MOR1D or MOR1-2B. As used herein, a "MOR1D binding agent" or "MOR1-2B binding agent" binds to MOR1D or MOR1-2B, respectively, and inhibits the interaction of MOR1D or MOR1-2B and GRPR. In preferred embodiments, the interaction of GRPR with MOR1D or MOR1-2B is inhibited by a GRPR-binding agent that inhibits interaction of GRPR and MOR1D or MOR1-2B. As used herein, a "GRPR-binding agent" binds to GRPR and inhibits the interaction of MOR1D or MOR1-2B and GRPR. Non-limiting examples of agents that may be used to inhibit the interaction of GRPR with MOR1D or MOR1-2B may include, but are not limited to, peptides, small molecules, antibodies, or the like.

In a preferred embodiment, the agent that inhibits interaction of GRPR and MOR1D or MOR1-2B is a peptide. In a particularly preferred embodiment, the peptide is derived from the C-terminal end of MOR1D or MOR1-2B. The C-terminal end of mouse MOR1D comprises the amino acid sequence EHPSTANTVDRTNHQRNEEPSS (SEQ ID NO:245). In some embodiments, the peptide derived from the C-terminal end of MOR1D comprises at least 5, at least 6, at least 7, at least 8, at least 9, at least 10, at least 11, at least 12, at least 13, at least 14, at least 15, at least 16, at least 17, at least 18, at least 19, at least 20, or at least 21, contiguous amino acids of the peptide comprising the amino acid sequence EHPSTANTVDRTNHQRNEEPSS (SEQ ID NO:245). In other embodiments, the peptide derived from the C-terminal end of MOR1D consists of an amino acid sequence listed in Table A. In a preferred alternative of the embodiment, the peptide derived from the C-terminal end of MOR1D comprises at least 7 contiguous amino acids of the peptide consisting of the amino acid sequence EHPSTANTVDRT-NHQRNEEPSS (SEQ ID NO:245). In an exemplary embodiment, the peptide derived from the C-terminal end of MOR1D comprises RNEEPSS (SEQ ID NO:82).

In another embodiment of the present invention, the peptide derived from the C-terminal end of MOR1-2B comprises DHPSTANTVDRTNHQRERRQKSDW (SEQ ID NO:548). In some embodiments, the peptide derived from the C-terminal end of MOR1-2B comprises at least 5, at least 6, at least 7, at least 8, at least 9, at least 10, at least 11, at least 12, at least 13, at least 14, at least 15, at least 16, at least 17, at least 18, at least 19, at least 20, or at least 21, contiguous amino acids of the peptide derived from the amino acid sequence DHPSTANTVDRTNHQRERRQKSDW (SEQ ID NO:548). In an alternate embodiment, the peptide derived from the C-terminal end of MOR1-2B consists of an amino acid sequence listed in Table B. In a preferred alternative of the embodiment, the peptide derived from the C-terminal end of MOR1-2B comprises at least 7 contiguous amino acids of the peptide consisting of the amino acid sequence DHPSTANTVDRTNHQRERRQKSDW (SEQ ID NO:548). In an exemplary embodiment, the peptide derived from the C-terminal end of MOR1D comprises RERRQKSDW (SEQ ID NO:410).

TABLE A

Amino Acid Sequence of the Peptide derived from the C-terminal end of MOR1D

| SEQ ID NO: | Amino Acid Sequence |
|---|---|
| 1 | EHPST |
| 2 | ANTVD |
| 3 | RTNHQ |
| 4 | RNEEP |
| 5 | HPSTA |
| 6 | NTVDR |
| 7 | TNHQR |
| 8 | NEEPS |
| 9 | PSTAN |
| 10 | TVDRT |
| 11 | NHQRN |
| 12 | EEPSS |
| 13 | STANT |
| 14 | VDRTN |
| 15 | HQRNE |
| 16 | QRNEE |
| 17 | TANTV |
| 18 | DRTNH |
| 19 | QRNEE |
| 20 | ANTVD |
| 21 | RTNHQ |
| 22 | RNEEP |
| 23 | NTVDR |
| 24 | TNHQR |

TABLE A-continued

Amino Acid Sequence of the Peptide derived from the C-terminal end of MOR1D

| SEQ ID NO: | Amino Acid Sequence |
|---|---|
| 25 | NEEPS |
| 26 | TVDRT |
| 27 | NHQRN |
| 28 | EEPSS |
| 29 | VDRTN |
| 30 | HQRNE |
| 31 | DRTNH |
| 32 | QRNEE |
| 33 | RTNHQ |
| 34 | RNEEP |
| 35 | TNHQR |
| 36 | NEEPS |
| 37 | NHQRN |
| 38 | EEPSS |
| 39 | HQRNE |
| 40 | QRNEE |
| 41 | RNEEP |
| 42 | NEEPS |
| 43 | EEPSS |
| 44 | EHPSTA |
| 45 | NTVDRT |
| 46 | NHQRNE |
| 47 | HPSTAN |
| 48 | TVDRTN |
| 49 | HQRNEE |
| 50 | PSTANT |
| 51 | VDRTNH |
| 52 | QRNEEP |
| 53 | STANTV |
| 54 | DRTNHQ |
| 55 | RNEEPS |
| 56 | TANTVD |
| 57 | RTNHQR |
| 58 | NEEPSS |
| 59 | ANTVDR |
| 60 | TNHQRN |
| 61 | NTVDRT |

TABLE A-continued

Amino Acid Sequence of the Peptide derived from the C-terminal end of MOR1D

| SEQ ID NO: | Amino Acid Sequence |
|---|---|
| 62 | NHQRNE |
| 63 | TVDRTN |
| 64 | HQRNEE |
| 65 | VDRTNH |
| 66 | QRNEEP |
| 67 | DRTNHQ |
| 68 | RNEEPS |
| 69 | RTNHQR |
| 70 | NEEPSS |
| 71 | TNHQRN |
| 72 | NHQRNE |
| 73 | HQRNEE |
| 74 | QRNEEP |
| 75 | RNEEPS |
| 76 | NEEPSS |
| 77 | EHPSTAN |
| 78 | TVDRTNH |
| 79 | QRNEEPS |
| 80 | HPSTANT |
| 81 | VDRTNHQ |
| 82 | RNEEPSS |
| 83 | PSTANTV |
| 84 | DRTNHQR |
| 85 | STANTVD |
| 86 | RTNHQRN |
| 87 | TANTVDR |
| 88 | TNHQRNE |
| 89 | ANTVDRT |
| 90 | NHQRNEE |
| 91 | NTVDRTN |
| 92 | HQRNEEP |
| 93 | TVDRTNH |
| 94 | QRNEEPS |
| 95 | VDRTNHQ |
| 96 | RNEEPSS |
| 97 | DRTNHQR |
| 98 | RTNHQRN |
| 99 | TNHQRNE |
| 100 | NHQRNEE |
| 101 | HQRNEEP |
| 102 | QRNEEPS |
| 103 | RNEEPSS |
| 104 | EHPSTANT |
| 105 | VDRTNHQR |
| 106 | HPSTANTV |
| 107 | DRTNHQRN |
| 108 | PSTANTVD |
| 109 | TNHQRNEE |
| 110 | STANTVDR |
| 111 | TNHQRNEE |
| 112 | TANTVDRT |
| 113 | NHQRNEEP |
| 114 | ANTVDRTN |
| 115 | HQRNEEPS |
| 116 | NTVDRTNH |
| 117 | QRNEEPSS |
| 118 | TVDRTNHQ |
| 119 | VDRTNHQR |
| 120 | DRTNHQRN |
| 121 | RTNHQRNE |
| 122 | TNHQRNEE |
| 123 | NHQRNEEP |
| 124 | HQRNEEPS |
| 125 | QRNEEPSS |
| 126 | EHPSTANTV |
| 127 | DRTNHQRNE |
| 128 | HPSTANTVD |
| 129 | RTNHQRNEE |
| 130 | PSTANTVDR |
| 131 | TNHQRNEEP |
| 132 | STANTVDRT |
| 133 | NHQRNEEPS |
| 134 | TANTVDRTN |
| 135 | HQRNEEPSS |
| 136 | ANTVDRTNH |

TABLE A-continued

Amino Acid Sequence of the Peptide derived from the C-terminal end of MOR1D

| SEQ ID NO: | Amino Acid Sequence |
|---|---|
| 137 | NTVDRTNHQ |
| 138 | TVDRTNHQR |
| 139 | VDRTNHQRN |
| 140 | DRTNHQRNE |
| 141 | RTNHQRNEE |
| 142 | TNHQRNEEP |
| 143 | NHQRNEEPS |
| 144 | HQRNEEPSS |
| 145 | EHPSTANTVD |
| 146 | RTNHQRNEEP |
| 147 | HPSTANTVDR |
| 148 | TNHQRNEEPS |
| 149 | PSTANTVDRT |
| 150 | NHQRNEEPSS |
| 151 | STANTVDRTN |
| 152 | TANTVDRTNH |
| 153 | ANTVDRTNHQ |
| 154 | NTVDRTNHQR |
| 155 | TVDRTNHQRN |
| 156 | VDRTNHQRNE |
| 157 | DRTNHQRNEE |
| 158 | RTNHQRNEEP |
| 159 | TNHQRNEEPS |
| 160 | EHPSTANTVDR |
| 161 | TNHQRNEEPSS |
| 162 | HPSTANTVDRT |
| 163 | PSTANTVDRTN |
| 164 | STANTVDRTNH |
| 165 | TANTVDRTNHQ |
| 166 | ANTVDRTNHQR |
| 167 | NTVDRTNHQRN |
| 168 | TVDRTNHQRNE |
| 169 | VDRTNHQRNEE |
| 170 | DRTNHQRNEEP |
| 171 | RTNHQRNEEPS |
| 172 | TNHQRNEEPSS |
| 173 | EHPSTANTVDRT |
| 174 | HPSTANTVDRTN |
| 175 | PSTANTVDRTNH |
| 176 | STANTVDRTNHQ |
| 177 | TANTVDRTNHQR |
| 178 | ANTVDRTNHQRN |
| 179 | NTVDRTNHQRNE |
| 180 | TVDRTNHQRNEE |
| 181 | VDRTNHQRNEEP |
| 182 | DRTNHQRNEEPS |
| 183 | RTNHQRNEEPSS |
| 184 | EHPSTANTVDRTN |
| 185 | HPSTANTVDRTNH |
| 186 | PSTANTVDRTNHQ |
| 187 | STANTVDRTNHQR |
| 188 | TANTVDRTNHQRN |
| 189 | ANTVDRTNHQRNE |
| 190 | NTVDRTNHQRNEE |
| 191 | TVDRTNHQRNEEP |
| 192 | VDRTNHQRNEEPS |
| 193 | DRTNHQRNEEPSS |
| 194 | EHPSTANTVDRTNH |
| 195 | HPSTANTVDRTNHQ |
| 196 | PSTANTVDRTNHQR |
| 197 | STANTVDRTNHQRN |
| 198 | TANTVDRTNHQRNE |
| 199 | ANTVDRTNHQRNEE |
| 200 | NTVDRTNHQRNEEP |
| 201 | TVDRTNHQRNEEPS |
| 202 | VDRTNHQRNEEPSS |
| 203 | EHPSTANTVDRTNHQ |
| 204 | HPSTANTVDRTNHQR |
| 205 | PSTANTVDRTNHQRN |
| 206 | STANTVDRTNHQRNE |
| 207 | TANTVDRTNHQRNEE |
| 208 | ANTVDRTNHQRNEEP |
| 209 | NTVDRTNHQRNEEPS |
| 210 | TVDRTNHQRNEEPSS |
| 211 | EHPSTANTVDRTNHQR |

TABLE A-continued

Amino Acid Sequence of the Peptide derived from the C-terminal end of MOR1D

| SEQ ID NO: | Amino Acid Sequence |
|---|---|
| 212 | HPSTANTVDRTNHQRN |
| 213 | PSTANTVDRTNHQRNE |
| 214 | STANTVDRTNHQRNEE |
| 215 | TANTVDRTNHQRNEEP |
| 216 | ANTVDRTNHQRNEEPS |
| 217 | NTVDRTNHQRNEEPSS |
| 218 | EHPSTANTVDRTNHQR |
| 219 | HPSTANTVDRTNHQRN |
| 220 | PSTANTVDRTNHQRNE |
| 221 | STANTVDRTNHQRNEE |
| 222 | TANTVDRTNHQRNEEP |
| 223 | ANTVDRTNHQRNEEPS |
| 224 | NTVDRTNHQRNEEPSS |
| 225 | EHPSTANTVDRTNHQRN |
| 226 | HPSTANTVDRTNHQRNE |
| 227 | PSTANTVDRTNHQRNEE |
| 228 | STANTVDRTNHQRNEEP |
| 229 | TANTVDRTNHQRNEEPS |
| 230 | ANTVDRTNHQRNEEPSS |
| 231 | EHPSTANTVDRTNHQRNE |
| 232 | HPSTANTVDRTNHQRNEE |
| 233 | PSTANTVDRTNHQRNEEP |
| 234 | STANTVDRTNHQRNEEPS |
| 235 | TANTVDRTNHQRNEEPSS |
| 236 | EHPSTANTVDRTNHQRNEE |
| 237 | HPSTANTVDRTNHQRNEEP |
| 238 | PSTANTVDRTNHQRNEEPS |
| 239 | STANTVDRTNHQRNEEPSS |
| 240 | EHPSTANTVDRTNHQRNEEP |
| 241 | HPSTANTVDRTNHQRNEEPS |
| 242 | PSTANTVDRTNHQRNEEPSS |
| 243 | EHPSTANTVDRTNHQRNEEPS |
| 244 | HPSTANTVDRTNHQRNEEPSS |
| 245 | EHPSTANTVDRTNHQRNEEPSS |

TABLE B

Amino Acid Sequence of the Peptide derived from the C-terminal end of MOR1-2B

| SEQ ID NO: | Amino Acid Sequence |
|---|---|
| 246 | DHPST |
| 247 | ANTVD |
| 248 | RTNHQ |
| 249 | RERRQ |
| 250 | HPSTA |
| 251 | NTVDR |
| 252 | TNHQR |
| 253 | ERRQK |
| 254 | PSTAN |
| 255 | TVDRT |
| 256 | NHQRE |
| 257 | RRQKS |
| 258 | STANT |
| 259 | VDRTN |
| 260 | HQRER |
| 261 | RQKSD |
| 262 | TANTV |
| 263 | DRTNH |
| 264 | QRERR |
| 265 | QKSDW |
| 266 | ANTVD |
| 267 | RTNHQ |
| 268 | RERRQ |
| 269 | NTVDR |
| 270 | TNHQR |
| 271 | ERRQK |
| 272 | TVDRT |
| 273 | NHQRE |
| 274 | RRQKS |
| 275 | VDRTN |
| 276 | HQRER |
| 277 | RQKSD |
| 278 | QKSDW |
| 279 | DRTNH |
| 280 | QRERR |
| 281 | QKSDW |
| 282 | RTNHQ |
| 283 | RERRQ |

TABLE B-continued

Amino Acid Sequence of the Peptide derived from the C-terminal end of MOR1-2B

| SEQ ID NO: | Amino Acid Sequence |
| --- | --- |
| 284 | TNHQR |
| 285 | ERRQK |
| 286 | NHQRE |
| 287 | RRQKS |
| 288 | HQRER |
| 289 | RQKSD |
| 290 | QRERR |
| 291 | QKSDW |
| 292 | RERRQ |
| 293 | ERRQK |
| 294 | RRQKS |
| 295 | RQKSD |
| 296 | QKSDW |
| 297 | DHPSTA |
| 298 | NTVDRT |
| 299 | NHQRER |
| 300 | RQKSDW |
| 301 | HPSTAN |
| 302 | TVDRTN |
| 303 | HQRERR |
| 304 | PSTANT |
| 305 | VDRTNH |
| 306 | QRERRQ |
| 307 | STANTV |
| 308 | DRTNHQ |
| 309 | RERRQK |
| 310 | TANTVD |
| 311 | RTNHQR |
| 312 | ERRQKS |
| 313 | ANTVDR |
| 314 | TNHQRE |
| 315 | RRQKSD |
| 316 | NTVDRT |
| 317 | NHQRER |
| 318 | RQKSDW |
| 319 | TVDRTN |
| 320 | HQRERR |
| 321 | VDRTNH |
| 322 | QRERRQ |
| 323 | DRTNHQ |
| 324 | RERRQK |
| 325 | RTNHQR |
| 326 | ERRQKS |
| 327 | TNHQRE |
| 328 | RRQKSD |
| 329 | NHQRER |
| 330 | RQKSDW |
| 331 | HQRERR |
| 332 | QRERRQ |
| 333 | RERRQK |
| 334 | ERRQKS |
| 335 | RRQKSD |
| 336 | RQKSDW |
| 337 | DHPSTAN |
| 338 | TVDRTNH |
| 339 | QRERRQ |
| 340 | HPSTANT |
| 341 | VDRTNHQ |
| 342 | RERRQKS |
| 343 | PSTANTV |
| 344 | DRTNHQR |
| 345 | ERRQKSD |
| 346 | RRQKSDW |
| 347 | STANTVD |
| 348 | RTNHQRE |
| 349 | TANTVDR |
| 350 | TNHQRER |
| 351 | ANTVDRT |
| 352 | NHQRERR |
| 353 | NTVDRTN |
| 354 | HQRERRQ |
| 355 | TVDRTNH |
| 356 | QRERRQK |
| 357 | VDRTNHQ |
| 358 | RERRQKS |

TABLE B-continued

Amino Acid Sequence of the Peptide derived from the C-terminal end of MOR1-2B

| SEQ ID NO: | Amino Acid Sequence |
|---|---|
| 359 | DRTNHQR |
| 360 | ERRQKSD |
| 361 | RTNHQRE |
| 362 | RRQKSDW |
| 363 | TNHQRER |
| 364 | NHQRERR |
| 365 | HQRERRQ |
| 366 | QRERRQK |
| 367 | RERRQKS |
| 368 | ERRQKSD |
| 369 | RRQKSDW |
| 370 | DHPSTANT |
| 371 | VDRTNHQR |
| 372 | ERRQKSDW |
| 373 | HPSTANTV |
| 374 | DRTNHQRE |
| 375 | PSTANTVD |
| 376 | RTNHQRER |
| 377 | STANTVDR |
| 378 | TNHQRERR |
| 379 | TANTVDRT |
| 380 | NHQRERRQ |
| 381 | ANTVDRTN |
| 382 | HQRERRQK |
| 383 | NTVDRTNH |
| 384 | QRERRQKS |
| 385 | TVDRTNHQ |
| 386 | RERRQKSD |
| 387 | VDRTNHQR |
| 388 | ERRQKSDW |
| 389 | DRTNHQRE |
| 390 | RTNHQRER |
| 391 | TNHQRERR |
| 392 | NHQRERRQ |
| 393 | HQRERRQK |
| 394 | QRERRQKS |
| 395 | RERRQKSD |
| 396 | ERRQKSDW |
| 397 | DHPSTANTV |
| 398 | DRTNHQRER |
| 399 | HPSTANTVD |
| 400 | RTNHQRERR |
| 401 | PSTANTVDR |
| 402 | TNHQRERRQ |
| 403 | STANTVDRT |
| 404 | NHQRERRQK |
| 405 | TANTVDRTN |
| 406 | HQRERRQKS |
| 407 | ANTVDRTNH |
| 408 | QRERRQKSD |
| 409 | NTVDRTNHQ |
| 410 | RERRQKSDW |
| 411 | TVDRTNHQR |
| 412 | VDRTNHQRE |
| 413 | DRTNHQRER |
| 414 | RTNHQRERR |
| 415 | TNHQRERRQ |
| 416 | NHQRERRQK |
| 417 | HQRERRQKS |
| 418 | QRERRQKSD |
| 419 | RERRQKSDW |
| 420 | DHPSTANTVD |
| 421 | RTNHQRERRQ |
| 422 | HPSTANTVDR |
| 423 | TNHQRERRQK |
| 424 | PSTANTVDRT |
| 425 | NHQRERRQKS |
| 426 | STANTVDRTN |
| 427 | HQRERRQKSD |
| 428 | TANTVDRTNH |
| 429 | QRERRQKSDW |
| 430 | ANTVDRTNHQ |
| 431 | NTVDRTNHQR |
| 432 | TVDRTNHQRE |
| 433 | VDRTNHQRER |

TABLE B-continued

Amino Acid Sequence of the Peptide derived from the C-terminal end of MOR1-2B

| SEQ ID NO: | Amino Acid Sequence |
|---|---|
| 434 | DRTNHQRERR |
| 435 | RTNHQRERRQ |
| 436 | TNHQRERRQK |
| 437 | NHQRERRQKS |
| 438 | HQRERRQKSD |
| 439 | QRERRQKSDW |
| 440 | DHPSTANTVDR |
| 441 | TNHQRERRQKS |
| 442 | HPSTANTVDRT |
| 443 | NHQRERRQKSD |
| 444 | PSTANTVDRTN |
| 445 | HQRERRQKSDW |
| 446 | STANTVDRTNH |
| 447 | TANTVDRTNHQ |
| 448 | ANTVDRTNHQR |
| 449 | NTVDRTNHQRE |
| 450 | TVDRTNHQRER |
| 451 | VDRTNHQRERR |
| 452 | DRTNHQRERRQ |
| 453 | RTNHQRERRQK |
| 454 | TNHQRERRQKS |
| 455 | NHQRERRQKSD |
| 456 | HQRERRQKSDW |
| 457 | DHPSTANTVDRT |
| 458 | NHQRERRQKSDW |
| 459 | HPSTANTVDRTN |
| 460 | PSTANTVDRTNH |
| 461 | STANTVDRTNHQ |
| 462 | TANTVDRTNHQR |
| 463 | ANTVDRTNHQRE |
| 464 | NTVDRTNHQRER |
| 465 | TVDRTNHQRERR |
| 466 | VDRTNHQRERRQ |
| 467 | DRTNHQRERRQK |
| 468 | RTNHQRERRQKS |
| 469 | TNHQRERRQKSD |
| 470 | NHQRERRQKSDW |
| 471 | DHPSTANTVDRTN |
| 472 | HPSTANTVDRTNH |
| 473 | PSTANTVDRTNHQ |
| 474 | STANTVDRTNHQR |
| 475 | TANTVDRTNHQRE |
| 476 | ANTVDRTNHQRER |
| 477 | NTVDRTNHQRERR |
| 478 | TVDRTNHQRERRQ |
| 479 | VDRTNHQRERRQK |
| 480 | DRTNHQRERRQKS |
| 481 | RTNHQRERRQKSD |
| 482 | TNHQRERRQKSDW |
| 483 | DHPSTANTVDRTNH |
| 484 | HPSTANTVDRTNHQ |
| 485 | PSTANTVDRTNHQR |
| 486 | STANTVDRTNHQRE |
| 487 | TANTVDRTNHQRER |
| 488 | ANTVDRTNHQRERR |
| 489 | NTVDRTNHQRERRQ |
| 490 | TVDRTNHQRERRQK |
| 491 | VDRTNHQRERRQKS |
| 492 | DRTNHQRERRQKSD |
| 493 | RTNHQRERRQKSDW |
| 494 | DHPSTANTVDRTNHQ |
| 495 | HPSTANTVDRTNHQR |
| 496 | PSTANTVDRTNHQRE |
| 497 | STANTVDRTNHQRER |
| 498 | TANTVDRTNHQRERR |
| 499 | ANTVDRTNHQRERRQ |
| 500 | NTVDRTNHQRERRQK |
| 501 | TVDRTNHQRERRQKS |
| 502 | VDRTNHQRERRQKSD |
| 503 | DRTNHQRERRQKSDW |
| 504 | DHPSTANTVDRTNHQR |
| 505 | HPSTANTVDRTNHQRE |
| 506 | PSTANTVDRTNHQRER |
| 507 | STANTVDRTNHQRERR |
| 508 | TANTVDRTNHQRERRQ |

TABLE B-continued

Amino Acid Sequence of the Peptide derived from the C-terminal end of MOR1-2B

| SEQ ID NO: | Amino Acid Sequence |
|---|---|
| 509 | ANTVDRTNHQRERRQK |
| 510 | NTVDRTNHQRERRQKS |
| 511 | TVDRTNHQRERRQKSD |
| 512 | VDRTNHQRERRQKSDW |
| 513 | DHPSTANTVDRTNHQRE |
| 514 | HPSTANTVDRTNHQRER |
| 515 | PSTANTVDRTNHQRERR |
| 516 | STANTVDRTNHQRERRQ |
| 517 | TANTVDRTNHQRERRQK |
| 518 | ANTVDRTNHQRERRQKS |
| 519 | NTVDRTNHQRERRQKSD |
| 520 | TVDRTNHQRERRQKSDW |
| 521 | DHPSTANTVDRTNHQRER |
| 522 | HPSTANTVDRTNHQRERR |
| 523 | PSTANTVDRTNHQRERRQ |
| 524 | STANTVDRTNHQRERRQK |
| 525 | TANTVDRTNHQRERRQKS |
| 526 | ANTVDRTNHQRERRQKSD |
| 527 | NTVDRTNHQRERRQKSDW |
| 528 | DHPSTANTVDRTNHQRERR |
| 529 | HPSTANTVDRTNHQRERRQ |
| 530 | PSTANTVDRTNHQRERRQK |
| 531 | STANTVDRTNHQRERRQKS |
| 532 | TANTVDRTNHQRERRQKSD |
| 533 | ANTVDRTNHQRERRQKSDW |
| 534 | DHPSTANTVDRTNHQRERRQ |
| 535 | HPSTANTVDRTNHQRERRQK |
| 536 | PSTANTVDRTNHQRERRQKS |
| 537 | STANTVDRTNHQRERRQKSD |
| 538 | TANTVDRTNHQRERRQKSDW |
| 539 | DHPSTANTVDRTNHQRERRQK |
| 540 | HPSTANTVDRTNHQRERRQKS |
| 541 | PSTANTVDRTNHQRERRQKSD |
| 542 | STANTVDRTNHQRERRQKSDW |
| 543 | DHPSTANTVDRTNHQRERRQKS |
| 544 | HPSTANTVDRTNHQRERRQKSD |
| 545 | PSTANTVDRTNHQRERRQKSDW |
| 546 | DHPSTANTVDRTNHQRERRQKSD |
| 547 | HPSTANTVDRTNHQRERRQKSDW |
| 548 | DHPSTANTVDRTNHQRERRQKSDW |

In yet another embodiment of the present invention, the agent that inhibits interaction of GRPR and MOR1D or MOR1-2B is an antibody. Antibodies of the invention may include antibodies that bind GRPR and MOR1D or MOR1-2B. Antibodies useful herein include those antibodies which have been isolated, characterized, purified, are functional and have been recovered (obtained) for use in a functional therapeutic composition. In a particularly preferred embodiment, an isolated antibody of the present invention that binds to MOR1D or MOR1-2B recognizes epitopes within the C-terminal end of MOR1D or MOR1-2B. The C-terminal end of mouse MOR1D comprises the amino acid sequence EHPSTANTVDRTNHQRNEEPSS (SEQ ID NO:245). In one embodiment, the isolated antibody of the present invention that binds to MOR1D recognizes an epitope with the amino acid sequence EHPSTANTVDRTNHQRNEEPSS (SEQ ID NO:245). The C-terminal end of human MOR1-2B comprises the amino acid sequence DHPSTANTVDRTNHQRERRQKSDW (SEQ ID NO:548). In another embodiment, the isolated antibody of the present invention that binds to MOR1-2B recognizes an epitope with the amino acid sequence DHPSTANTVDRTNHQRERRQKSDW (SEQ ID NO:548).

"Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

Further by "antibody" is meant a functional monoclonal antibody, or an immunologically effective fragment thereof; such as an Fab, Fab', or F(ab')2 fragment thereof. In some contexts herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Also included within the definition "antibody" for example are single chain forms, generally designated Fv, regions, of antibodies with this specificity. Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated. Antibodies are properly cross-linked via disulfide bonds, as is known.

The basic antibody structural unit of an antibody useful herein comprises a tetramer. Each tetramer is composed of two identical pairs of polypeptide chains, each pair having one "light' (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgO, IgM, IgA, IgD and IgE, respectively. Within light and heavy chains, the variable and constant regions are joined by a "J" region of about 12 or more amino acids, with the heavy chain also including a "D" region of about 10 more amino acids.

The variable regions of each light/heavy chain pair form the antibody binding site. Thus, an intact antibody has two binding sites. The chains exhibit the same general structure of relatively conserved framework regions (FR) joined by three hypervariable regions, also called complementarily determining regions (hereinafter referred to as "CDRs.") The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acids to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In an aspect, monoclonal anti-GRPR and anti-MOR1D or anti-MOR1-2B antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with a peptide representing an epitope encompassing a region of the tau protein coding sequence or an appropriate subregion thereof. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an anti-GRPR and anti-MOR1D or anti-MOR1-2B antibody that is composed partially or fully of amino acid sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for tau is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

If desired, the design of humanized immunoglobulins may be carried out as follows. When an amino acid falls under the following category, the framework amino acid of a human immunoglobulin to be used (acceptor immunoglobulin) is replaced by a framework amino acid from a CDR-providing nonhuman immunoglobulin (donor immunoglobulin): (a) the amino acid in the human framework region of the acceptor immunoglobulin is unusual for human immunoglobulin at that position, whereas the corresponding amino acid in the donor immunoglobulin is typical for human immunoglobulin at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model (Queen, et al., op. cit., and Co, ct al, Proc. Natl. Acad. Sci. USA (1991) 88:2869). When each of the amino acids in the human framework region of the acceptor immunoglobulin and a corresponding amino acid in the donor immunoglobulin is unusual for human immunoglobulin at that position, such an amino acid is replaced by an amino acid typical for human immunoglobulin at that position.

The antibodies of the present invention may also be used as fusion proteins known as single chain variable fragments (scFv). These scFvs comprise of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or theronine. ScFvs can be used to facilitate phage display or can be used for flow cytometry, immunohistochemistry, or as targeting domains. Methods of making and using scFvs are known in the art.

In a preferred embodiment, the scFvs of the present invention are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

(b) Cell-Penetrating Peptide

In some embodiments, an agent that inhibits the interaction of GRPR and MOR1D or MOR1-2B is fused to a cell-penetrating peptide. In an exemplary embodiment, a peptide derived from the C-terminal end of MOR1D or MOR1-2B is fused to a cell-penetrating peptide. Cell-Penetrating Peptides (CPPs), also known as protein transduction domains (PTDs), membrane translocating sequences (MTSs), and Trojan peptides are short peptides (40 amino acids), with the ability to gain access to the interior of almost any cell. Non limiting examples of CPPs that may be fused to the peptide derived from the C-terminal end of MOR1D or MOR1-2B include penetratin (PTD RQIKWFQNRRMKWKK; SEQ ID NO:549), TAT (YGRKKRRQRRR; SEQ ID NO:550), SynB1 (RGGRLSYSRRRFSTSTGR; SEQ ID NO:551), SynB3 (RRLSYSRRRF; SEQ ID NO:552), PTD-4 (PIRRKKLRRLK; SEQ ID NO:553), PTD-5 (RRQRRTSKLMKR; SEQ ID NO:554), FHV Coat-(35-49) (RRRRNRTRRNRRRVR; SEQ ID NO:555), BMV Gag-(7-25) (KMTRAQRRAAARRNRWTAR; SEQ ID NO:556), HTLV-II Rex-(4-16) (TRRQRTRRARRNR; SEQ ID NO:557), D-Tat (GRKKRRQRRRPPQ; SEQ ID NO:558), R9-Tat (GRRRRRRRRRPPQ; SEQ ID NO:559), Transportan (GWTLNSAGYLLGKINLKALAALAKKIL; SEQ ID NO:560), MAP (KLALKLALKLALALKLA; SEQ ID NO:561), SBP (MGLGLHLLVLAAALQGAWSQPKKKRKV; SEQ ID NO:562), FBP (GALFLGWLGAAGSTMGAWSQPKKKRKV; SEQ ID NO:563), MPG (ac-GALFLGFLGAAGSTMGAWSQPKKKRKV-cya; SEQ ID NO:564), MPG(ENLS) (ac-GALFLGFLGAAGSTMGAWSQPKSKRKV-cya; SEQ ID NO:565), Pep-1 (ac-KETWWETWWTEWSQPKKKRKV-cya; SEQ ID NO:566), Pep-2 (ac-KETWFETWFTEWSQPKKKRKV-cya; SEQ ID NO:567), Polyarginines R×N (4<N<17) chimera, Polylysines K×N (4<N<17) chimera, (RAca)6R, (RAbu)6R, (RG)6R, (RM)6R, (RT)6R, (RS)6R, R10, (RA)6R, and R7.

In a preferred embodiment, the peptide derived from the C-terminal end of MOR1D or MOR1-2B is fused to the TAT cell penetrating peptide. In one alternative of the embodiment, the peptide derived from the C-terminal end of MOR1D is fused to the C terminus of the TAT cell penetrating peptide. In a preferred alternative of the embodiment, the peptide derived from the C-terminal end of MOR1-2B is fused to the C terminus of the TAT cell penetrating peptide.

Methods of generating a fusion peptide are known in the art. It is appreciated that any of those known methods for generating a fusion protein will work for purposes of the present invention.

(c) Administering the Peptide

The peptide of the invention generally will cross the blood brain barrier (BBB) of the subject to contact GRPR or MOR1D or MOR1-2B in the central nervous system. The peptide may be delivered across the (BBB). Methods of delivering antagonists across the BBB are known in the art and it can be appreciated that any of such known methods will work for purposes of the present invention. For instance, the peptide may be delivered via injection into the intrathecal space. Additionally, modalities for peptide delivery across the BBB may entail its disruption by osmotic means, biochemically by the use of vasoactive substances such as bradykinin, or even by localized exposure to high intensity focused ultrasound (HIFU). Other strategies to cross the BBB may entail the use of endogenous transport systems, including carrier-mediated transporters, receptor-mediated transcytosis, and blocking of active efflux transporters.

Injectable preparations of the peptide, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally or intrathecally acceptable diluent or solvent. Among the acceptable vehicles and solvents that may be employed, non-limiting examples are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

For therapeutic purposes, formulations for administration of the peptide may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in solvents that include, but are not limited to water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Accordingly, any known adjuvant compatible with the peptide of the present invention is suitable and can be readily determined by one of skill in the art.

The amount of the peptide that may be combined with the carrier materials to produce a single dosage of the composition will vary depending upon the subject and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

II. Combinations

Another aspect of the present disclosure provides a combination comprising an agent that substantially inhibits the interaction of GRPR with MOR1D or MOR1-2B and an at least one analgesic agent. Suitable analgesic agents are described below.

(a) Analgesic Agent

A combination of the invention comprises at least one analgesic agent. For instance, a combination of the invention may comprise at least one, at least two, at least three, at least four, at least five, at least six, or more than six analgesic agents. In preferred embodiments, at least one analgesic agent may be an opioid. As used herein, an "opioid" is a substance that binds to an opioid receptor and possesses biological activity. A non-limiting example of an opioid is an opiate. In certain embodiments, the combination may comprise at least one opioid analgesic and at least one non-opioid analgesic.

i. Opioid Analgesic Agents

An analgesic agent of the present invention may be an opioid analgesic agent. In some embodiments, an opioid analgesic may be a full or a partial opioid receptor agonist. In exemplary embodiments of the invention, the opioid analgesic agent induces pruritus. Examples of useful opioid agonists include, but are not limited to, alfentanil, allylprodine, alphaprodine, anilehdine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenopehdine, piminodine, pihtramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

In other embodiments, a combination may comprise more than one opioid analgesic. For instance, a combination may comprise more than one full opioid agonist, more than one partial opioid agonist, or at least one full opioid agonist and at least one partial opioid agonist.

The amount of the opiate analgesic agent that comprises a combination of the invention depends, in part, upon the analgesic chosen and whether the dosage form is to be formulated for immediate release or sustained release of the analgesic. For example, if morphine is the intended opiate, the morphine may be present in single doses between about 10 mg and about 60 mg including, but not limited to, about 15 mg, about 20 mg, about 30 mg and about 40 mg. Alternatively, a pharmaceutical combination may be formulated to include between about 30 mg to about 60 mg of morphine in a single slow-release tablet or capsule, including, but not limited to about 35 mg, about 40 mg, about 45 mg, about 50 mg, and about 55 mg. If meperidine is chosen as the analgesic or a member of the analgesic combination, the meperidine may be present in single doses ranging from about 50 mg to about 150 mg, including, but not limited to about 60 mg, about 70 mg, about 80 mg, about 90 mg, about 100 mg, about 110 mg, about 120 mg, about 130 mg, and about 140 mg of meperidine. If fentanyl is chosen as the analgesic or a member of the analgesic combination, the fentanyl may be present in doses equivalent to doses ranging from about 200 µg, to about 1600 µg per single dose, including about 400 µg, about 600 µg, about 800 µg, about 1000 ug, and about 1200 µg of fentanyl base. If hydromorphone is chosen as the analgesic or a member of the analgesic combination, the hydromorphone may be present in doses ranging from about 1 mg to about 5 mg of hydromorphone per single dose, including, but not limited to about 2 mg, about 3 mg, and about 4 mg of hydromorphone. If oxymorphone is chosen as the analgesic or a member of the analgesic combination, the oxymorphone may be present in doses ranging from about 1 mg to about 10 mg per single dose, including, but not limited to, about 3 mg, about 5 mg, and about 7 mg per single dose. If oxycodone is chosen as the analgesic or a member of the analgesic combination, the oxycodone may be present in doses ranging from about 5 mg to about 20 mg per single dose, including, but not limited to, about 7 mg, about 10 mg, about 12 mg, about 15 mg, about 17 mg, and about 19 mg per single dose. If hydrocodone is chosen as the analgesic or a member of the analgesic combination, the hydrocodone may be present in doses ranging from about 2.5 mg to about 15 mg, including, but not limited to, about 5 mg, about 7.5 mg and about 10 mg per single dose. If methadone is chosen as the analgesic or a member of the analgesic combination, the methadone may be present in doses ranging from about 5 mg to about 10 mg per single dose, including, but not limited to, about 6 mg, about 7 mg, about 8 mg, and about 9 mg per single dose. If propoxyphene is chosen as the analgesic or a member of the analgesic combination, the propoxyphene may be present in doses ranging from about 32 mg to about 65 mg of the hydrochloride salt or from about 50 mg to about 100 mg of the napsylate salt per single dose. If pentazocine is chosen as the analgesic or a member of the analgesic combination, the pentazocine may be present in doses including, but not limited to, about 50 mg pentazocine base or doses of a pharmaceutically-acceptable salt of pentazocine approximately equivalent to about 50 mg of pentazocine base per single dose. If levorphanol is chosen as the analgesic or a member of the analgesic combination, the levorphanol may be present in doses including but not limited to about 2 mg of levorphanol tartrate per single dose. If codeine is chosen as the analgesic or a member of the analgesic combination, the codeine may be present in doses including but not limited to doses of a pharmaceutically-acceptable salt of codeine approximately equivalent to a range from about 30 mg to about 60 mg of codeine phosphate or approximately equivalent to a range of about 15 mg to about 60 mg of codeine sulfate per single dose.

ii. Non-Opioid Analgesic Agent

In another embodiment, a combination of the invention may comprise at least one non-opioid analgesic. Non-limiting examples of useful non-opioid analgesics include nonsteroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof.

Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium thsalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. It is understood that combinations of these non-opioid analgesics may be included in a combination of the present invention.

For a more detailed description of the NSAIDs, see Paul A. Insel, Analgesic-Antipyretic and Anti-inflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996) and Glen R. Hanson, Analgesic, Antipyretic and Anti-Inflammatory Drugs in Remington: The Science and Practice of Pharmacy Vol II 1196-1221 (A. R. Gennaro ed. 19th ed. 1995) which are hereby incorporated by reference in their entireties. Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Dosages of non-opioid analgesic agents are known in the art, and depend, in part, on the subject, the analgesic agent, the origin of the pain, and the administration route. For instance, in some embodiments, the dosage of rofecoxib may be between about 5 mg and about 60 mg per day, including, but not limited to, about 10 mg, about 20 mg, about 30 mg, about 40 mg, and about 50 mg per day; the dosage of celecoxib may be between about 25 mg and about 500 mg per day, including, but not limited to, about 50 mg, about 100 mg, about 150 mg, about 200 mg, about 250 mg, about 300 mg, about 350 mg, about 400 mg, and about 450 mg per day; the dosage of naprosyn may be between about 250 mg and 1250 mg per day, including, but not limited to, about 400 mg, about 500 mg, about 600 mg, about 700 mg, about 800 mg, about 900 mg, and about 1000 mg per day; and the dosage of aspirin may be between about 80 mg and about 400 mg per day, including, but not limited to, about 100 mg, about 150 mg, about 200 mg, about 250 mg, about 300 mg, and about 350 mg per day. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

iii. Combinations of Opioid and Non-Opioid Analgesic Agents

As detailed above, a combination of the invention may comprise more than one analgesic agent. This is particularly true if the analgesic agents, when administered together, produce a synergistic analgesic effect. In certain embodiments, a combination comprises at least one opioid analgesic agent and at least one non-opioid analgesic.

Acetaminophen has been shown to have a synergistic analgesic activity with the opiate analgesics. Accordingly, in some embodiments, a combination may comprise at least one opioid analgesic and acetaminophen. In the embodiments of the present invention comprising acetaminophen, the acetaminophen is generally present in a range of between about 10 mg and about 2000 mg, including, but not limited to about 50 mg, about 100 mg, about 250 mg, about 500 mg, about 750 mg, about 1,000 mg, about 1250 mg, about 1500 mg, and about 1750 mg of acetaminophen. In certain embodiments, the acetaminophen is present in a range of about 50 mg to about 1000 mg per dosage form, including, but not limited to about 100 mg, about 150 mg, about 200 mg, about 250 mg, about 300 mg, about 325 mg, about 500 mg, about 750 mg, and about 800 mg per dosage form. For more details on combinations comprising acetaminophen, see U.S. Pat. No. 6,375,957, hereby incorporated by reference in its entirety.

iv. Pharmaceutical Compositions Comprising Analgesic Agents

An analgesic agent detailed above may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Non-limiting examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic(pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyhc, salicylic, galactahc and galacturonic acid. Suitable pharmaceutically-acceptable base addition salts of compounds of use in the present methods include, but are not limited to, metallic salts made from aluminum, calcium, lithium, magnesium, potassium, sodium and zinc or organic salts made from N, N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with any of the compounds of the invention.

(b) Other Agents

Combinations of the present invention may further comprise additional agents. For instance, a combination may comprise an agent directed to alleviating an unwanted side effect of the analgesic agent. Non-limiting examples may include an anti-nausea agent, an anti-vomiting agent, an agent to alleviate constipation, an agent to alleviate respiratory depression, an opioid antagonist, and combinations thereof.

Anti-nausea or anti-vomiting agents may include 5-HT3 receptor antagonists such as dolasetron, granisetron, ondansetron, tropisetron, and palonosetron; dopamine antagonists, such as dompehdone, droperidol, halopehdol, chlorpromazine, promethazine, prochlorperazine, metoclopramide, and alizapride; antihistamines (H1 histamine receptor antagonists) such as cyclizine, diphenhydramine, dimenhydrinate (Gravol), meclizine, promethazine (pentazine, phenergan, promacot), and hydroxyzine; cannabinoids such as cannabis (marijuana), dronabinol (Marinol), nabilone (Cesamet), and sativex; benzodiazepines, such as midazolam and lorazepam; anticholinergics such as hyoscine (also known as scopolamine); steroids such as dexamethasone; trimethobenzamide; ginger; emetrol; propofol given intravenously; peppermint; or other suitable anti-nasea or anti-vomiting agents. The amount of an anti-nausea or anti-vomiting agent included in a combination of the invention may be readily determined by one of skill in the art. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

Agents to alleviate constipation are well known in the art. In particular, combinations of opioids and agents to alleviate constipation are known in the art. For instance, see U.S. Pat. No. 6,982,283.

Opioid antagonists useful in the present invention may include, for example and without limitation, naltrexone, naloxone, nalmefene, nalide, nalmexone, nalorphine, nalorphine dinicotinate, cyclazocine, levallorphan, pharmaceutically acceptable salts thereof, and mixtures thereof. In certain embodiments, the opioid antagonist is naloxone or naltrexone. Typically the amount of antagonist included in a combination of the invention may vary with the analgesic or analgesics, the patient, and the source of the antagonist. In certain embodiments, the amount of the opioid antagonist included in the dosage form, may be about 0.00001 mg to 275 mg, including, but not limited to, about 0.0001 mg, about 0.001 mg, about 0.01 mg, about 0.1 mg, about 10 mg, about 50 mg, about 100 mg, about 150 mg, about 200 mg, and about 250 mg of the opiod antagnoist. Those skilled in the art will also appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493. For instance, see U.S. Pat. No. 6,475,494 or 6,696,066.

(c) Pharmaceutical Compositions and Routes of Administration

Combinations of the invention may comprise a pharmaceutical composition. The agents of the invention may be formulated separately, or in combination. In some embodiments, the compositions may comprise pharmaceutically acceptable excipients. Examples of suitable excipients may include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, methyl cellulose, and combinations thereof. The compositions of the present invention may additionally include: lubricating agents such as talc, magnesium stearate, and mineral oil; wetting agents; emulsifying and suspending agents; preserving agents such as methyl- and propylhydroxy-benzoates; sweetening agents; flavoring agents and combinations thereof. The compositions of the invention may be formulated so as to provide quick, sustained or delayed release of the active ingredient after administration to a subject by employing procedures known in the art.

The active compounds of the invention may be effective over a wide dosage range and are generally administered in pharmaceutically effective amounts. It will be understood, however, that the amount of the compounds actually administered will be determined by a physician, in the light of the relevant circumstances, including the condition to be treated, the analgesic to be administered, the age, weight, and response of the individual patient, the severity of the patient's symptoms, and the like.

The composition of the present invention may be administered in a pharmaceutical product in a form selected from, but not limited to, tablets, capsules, gel capsules, liquid formulations, injectible formulations, oral formulations, powder formulations, and the like. It is appreciated that those of skill in the art are aware of methods to produce the pharmaceutical products contemplated by the present invention.

The tablets or capsules of the present invention may be coated or otherwise compounded to provide a dosage form affording the advantage of prolonged action. For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate as are known in the art.

The liquid forms in which the compositions of the present invention may be incorporated for administration include, but are not limited to, aqueous solutions, suitably flavored syrups, oil suspensions and flavored emulsions with edible oils such as cottonseed oil, sesame oil, coconut oil, or peanut oil as well as elixirs and similar pharmaceutical vehicles. Liquid dosage forms for oral administration may also include pharmaceutically acceptable emulsions, solutions, suspensions, and elixirs containing inert diluents commonly used in the art, such as water. Such compositions may also comprise adjuvants, such as wetting agents, emulsifying and suspending agents, and sweetening, flavoring, and perfuming agents.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

DEFINITIONS

As used herein, the term "splice variant" is the polypeptide product of alternative or differential splicing of an mRNA. Alternative splicing is a process by which the exons of the RNA produced by transcription of a gene (a primary gene transcript or pre-mRNA) are reconnected in multiple ways during RNA splicing.

As used herein, "subject" encompasses mammals with pruritus specific neurons that comprise GRPR. In one embodiment, subject refers to a mammal selected from the group comprising rodents, non-human primates, and humans. In another embodiment, subject refers to humans.

As used herein, "substantially," generally means greater than 50%. For example, "substantially inhibiting activation" means inhibiting greater than 50% of the activation compared to no inhibition. Similarly, "substantially impeding function" means inhibiting greater than 50% of the function compared to no impedance. In some embodiments, substantially may mean greater than 55, 60, 65, 70, 75, 80, 85, 90, or 95%. In other embodiments, substantially may mean greater than 95, 96, 97, 98, or 99%.

As used herein, "reducing" means reversing, alleviating, inhibiting the progress of, or preventing pruritus, or one or more symptoms of such disorder or condition.

As used herein, "internalization" refers to the process of transporting GRPR from the cell surface to an intracellular compartment. "Opioid-induced internalization" refers to internalization of GRPR after opioid administration.

EXAMPLES

The following examples illustrate various iterations of the invention.

Introduction to Examples 1-9.

Itch and pain are two fundamental sensory perceptions evoked by distinct external inputs. They are encoded and transmitted by primary nociceptive fibers and varying subpopulations of dorsal horn neurons (Davidson and Giesler, 2010; Patel and Dong, 2010). The ability to discriminate between itch and pain allows animals to employ the proper motor response (scratching vs. withdrawal) so that potentially damaging stimuli from the environment can be avoided. Intriguingly, it has been well documented that itch and pain may counteract each other under some conditions. Indeed, a wide range of noxious stimuli including thermal, mechanical, chemical and electrical stimuli are able to inhibit itch (Ikoma et al., 2006). Conversely, it is widely assumed that itch may be unmasked by pain reduction, and one of the most cited examples of this antagonistic relationship is opioid-induced itch, or pruritus (Davidson and Giesler, 2010; Ikoma et al., 2006; Paus et al., 2006). In fact, pruritus is one of the most prevalent acute side effects of the spinal or epidural use of opioids in patients who undergo pain treatment or in those who receive cesarean section (Ballantyne et al., 1988; Chaney, 1995; Hales, 1980), which has hampered the use of opioids as an analgesic to their full extent. The most influential theory offered to explain the antagonism of itch and pain is perhaps the "occlusion" or selectivity hypothesis, which stipulates that pruriceptors are part of nociceptors and that an inactivation of the pain signaling centrally is a prerequisite for activation of the itch signaling (Carstens, 1997; McMahon and Koltzenburg, 1992). The occlusion hypothesis has gained more support from an analysis of mutant mice lacking vesicular glutamate transporter 2 in subsets of dorsal root ganglia (DRG) neurons that displayed attenuated pain but enhanced itch (Lagerstrom et al., 2010; Liu et al., 2010). In the spinal cord, all spinothalamic track (STT) neurons in primates recorded to be responsive to capsaicin also responded to pruritic stimuli (Davidson et al., 2007). In addition, ablation of dorsal horn neurons expressing neurokinin 1 receptor (NK1) attenuated both pain and itch in rats (Carstens et al., 2010; Nichols et al., 1999). Mice lacking neurons expressing gastrin-releasing peptide receptor (GRPR), a molecular signature for the putative itch-specific labeled line in the spinal cord, nearly eliminate their scratching response to pruritic stimuli without altering normal nociceptive transmission (Sun and Chen, 2007; Sun et al., 2009). Conversely, mice lacking a subset of neurons expressing transcription factor Bhlhb5 during development display enhanced spontaneously scratching behavior but their pain behavior is not reduced (Ross et al., 2010), suggesting that removal of pain signaling is not a prerequisite for induction of itch and that the central itch signaling can be induced independently of nociceptive transmission. Collectively, convincing evidence in support of "occlusion" theory in the spinal cord is lacking.

Opioid-induced itch has been suggested to be mediated primarily through the μ opioid receptor (MOR), a key receptor for opiates (Kieffer, 1999). Intrathecal (i.t.) injection of morphine, a prototypical opiate agonist, produces dose-dependent scratching behavior (Ko and Naughton, 2000; Kuraishi et al., 2000). Consistently opioid antagonists have been found to reduce itch and concomitantly attenuate the analgesic effects of opiates (Ballantyne et al., 1988; Ko et al., 2004). MOR1 is activated by exogenous morphine without rapid internalization in several cell types including dorsal horn neurons (Alvarez et al., 2002; Keith et al., 1996; Trafton et al., 2000). Activation of MOR1 primarily inhibits adenylyl cyclase, and the cAMP/PKA signaling pathway (Law et al., 2000). Since opioid-induced itch, or pruritus, is most notable and severe when opioids are intrathecally applied, one tantalizing hypothesis is that opioids evoke itch sensation by activating GRPR signaling.

Example 1

Morphine-Induced Scratching (MIS) Occurs Independent of Morphine-Induced Analgesia (MIA)

Figure 1:
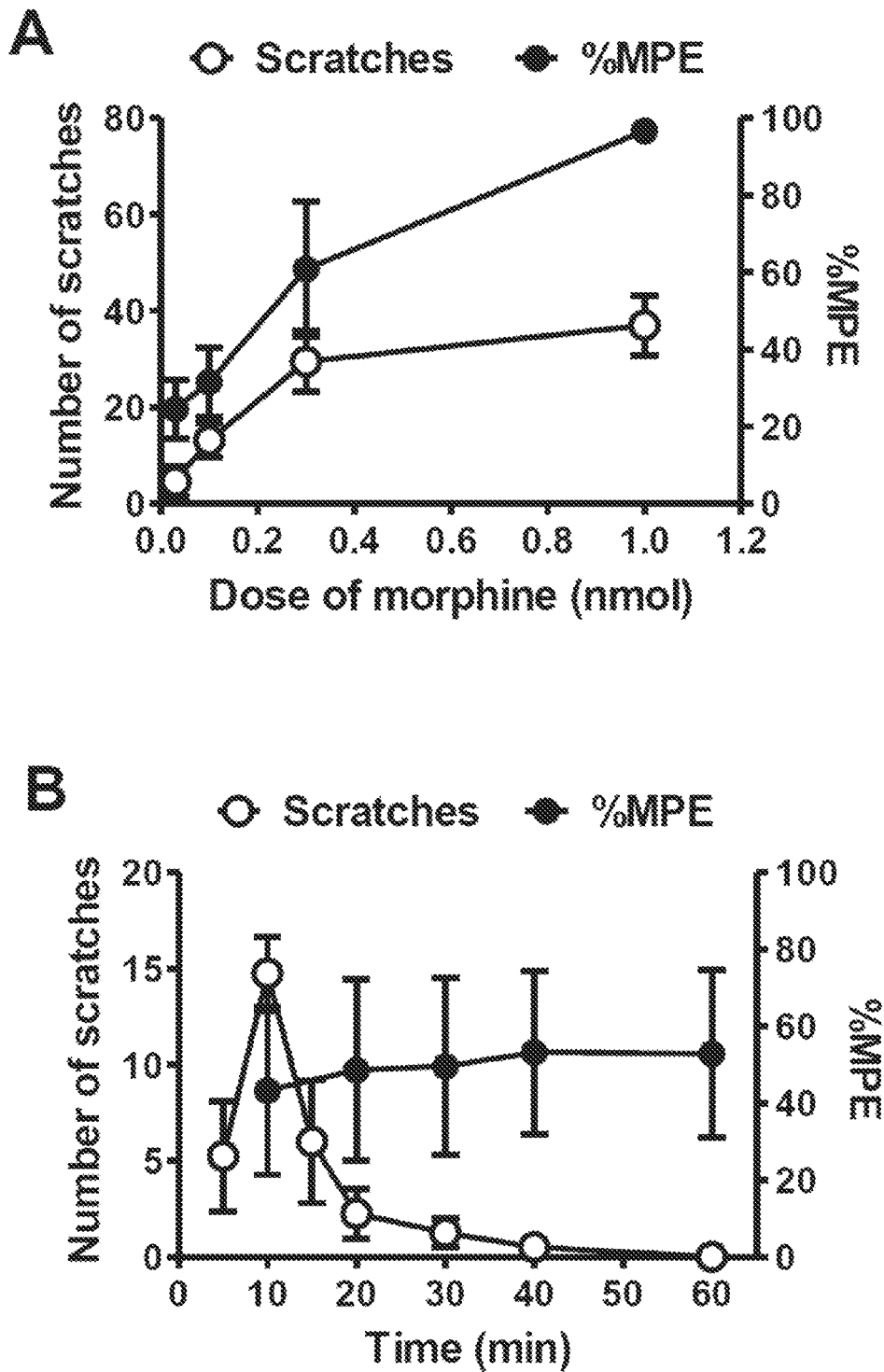
FIG. 1 MIS is not correlated with MIA. (A) Dose effect of i.t. morphine on MIS and MIA in 30 min. (B) Time course of morphine (0.3 nmol, i.t.) on MIS and MIA. (C) For induction of acute MIA tolerance, mice were treated with morphine (100 mg/kg, subcutaneous injection) or saline. Anti-nociception was assessed by tail immersion assay. Twenty-four hr after the morphine treatment, mice had returned to the basal nociceptive latencies. (D) Twenty-four hr after morphine (100 mg/kg, subcutaneous injection) treatment, acute antinociceptive tolerance was tested with i.t. morphine and tail-flick latencies were recorded. *$p<0.05$. (E) i.t. morphine induced comparable scratches in acute morphine antinociceptive tolerant and control mice. (F) For induction of chronic MIA tolerance, mice received daily injection of morphine (10 mg/kg, subcutaneous injection) or saline for 5 days and examined for MIA tolerance daily by. (G) After 5 days of systemic morphine injection, i.t. morphine also showed antinociceptive tolerance. *$p<0.05$. (H) i.t. morphine induced comparable scratches in chronic morphine antinociceptive tolerant and control mice. In all experiments, the dose of i.t. morphine is 0.3 nmol. n=6~8 per group. Error bars represent standard error of the mean.
Figure 1:
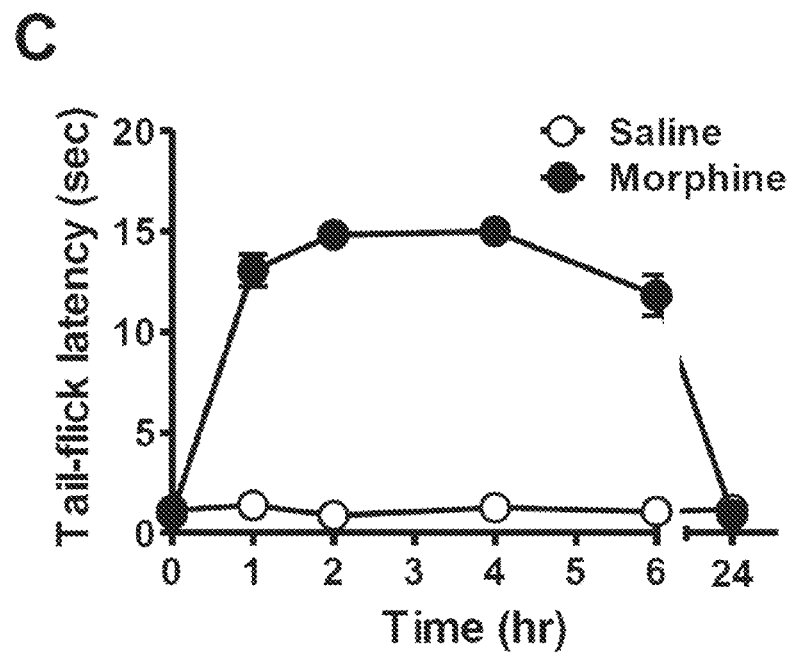
Figure 1:
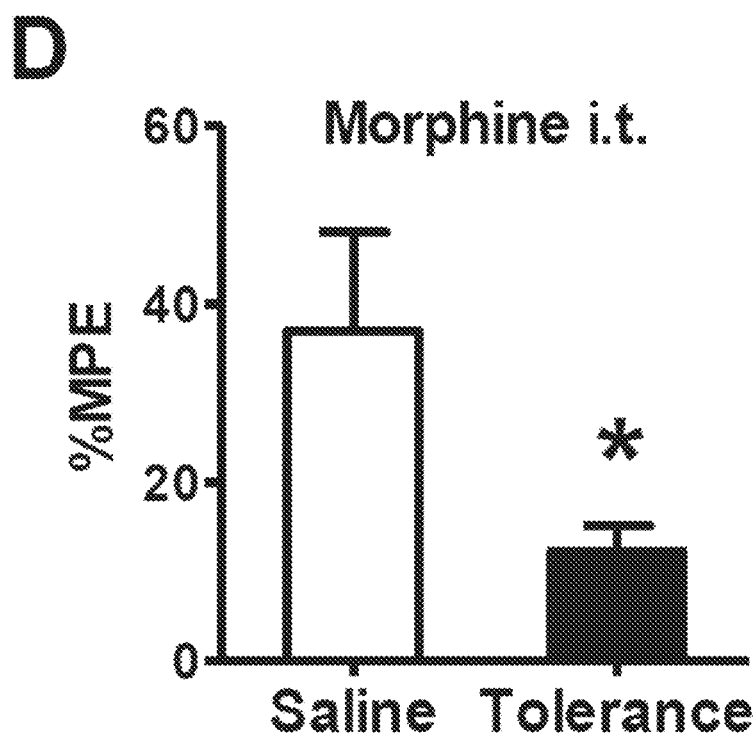
Figure 1:
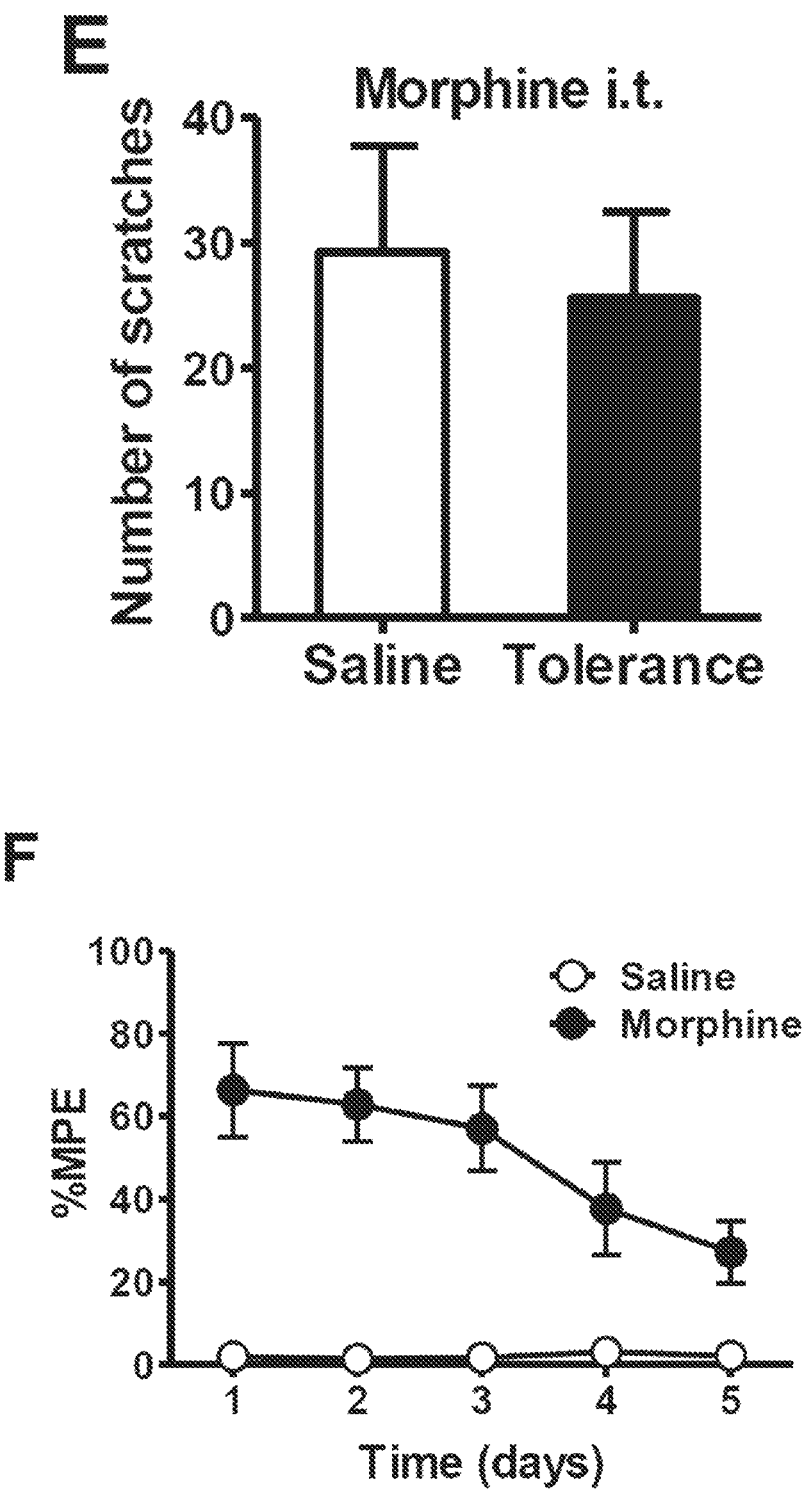
Figure 1:
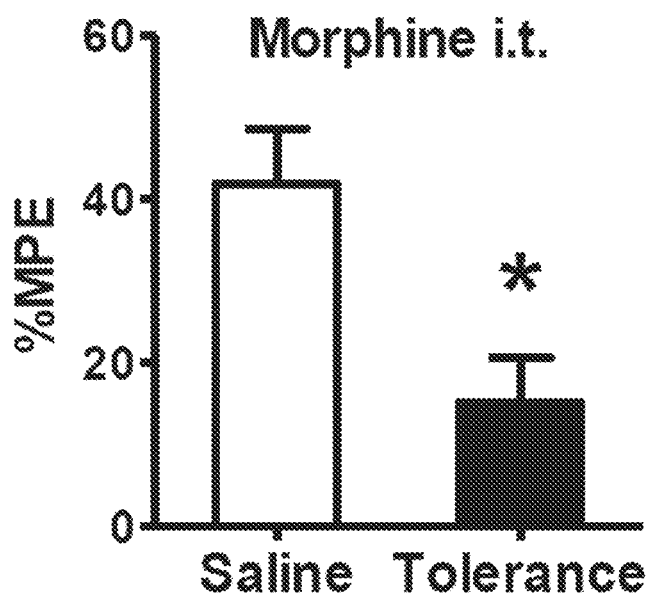
Figure 1:
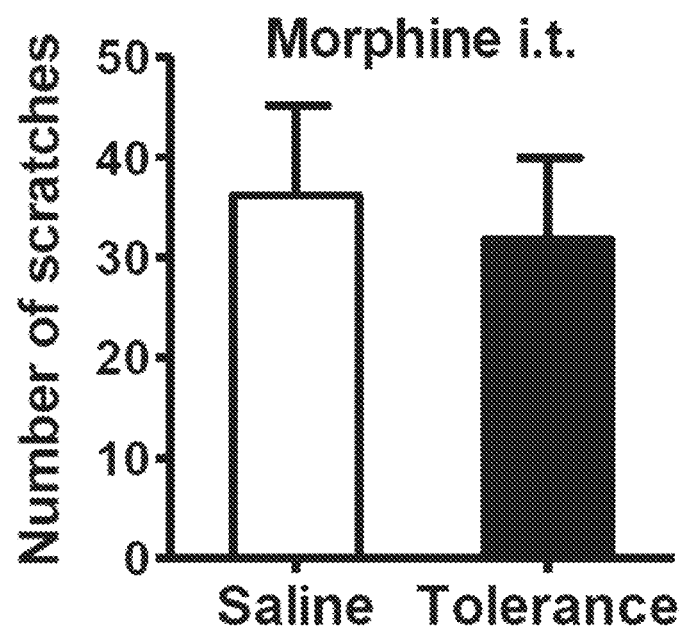

To examine whether MIS and MIA are correlated to each other, the dose-response curve and time course of MIS and MIA were studied after intrathecal (i.t.) injection of morphine. As shown in FIG. 1A, both MIA and MIS increased in a dose-dependent manner. However, when the morphine dose increased from 0.3 nmol to 1.0 nmol, MIA effect was enhanced by 81%, while MIS only had a slight increase. In addition, time course analysis at 0.3 nmol of morphine revealed obvious segregation of MIA and MIS (FIG. 1B). After i.t. morphine MIS increased dramatically within 10 min and quickly decreased. No scratches were seen after 40 min. In contrast, MIA maintained at a maximal level for at least one hr. To further examine whether opioid-induced itch is due to pain inhibition, a morphine tolerance paradigm was employed in which the degree of tolerance to morphine is measured by the latency of tail-flick (analgesic effect) (Fairbanks and Wilcox, 1999). If pain inhibition unmasks itch, MIS would be attenuated in mice with morphine tolerance. Twenty-four hr after morphine pretreatment, tail-flick latencies of mice returned to their baseline (FIG. 1C). As expected, mice pretreated with morphine developed morphine tolerance as measured by a significant reduction of MIA relative to the saline control (FIG. 1D). Surprisingly, despite reduced analgesic effect, MIS did not differ between the two groups (FIG. 1E). To further confirm that MIS could be separated from MIA, chronic morphine tolerance was induced by repeated subcutaneous injection of morphine. Tail immersion assay showed gradually reduced amplitude of MIA during the five days of induction (FIG. 1F). On the sixth day, morphine tolerance was evident by a significant reduction of MIA relative to the saline control (FIG. 1G). Again, there was not a significant difference of MIS between the control and tolerant mice (FIG. 1H). Therefore, despite dose-related MIS and MIA response, MIS occurs irrespective of the degree of MIA, indicating that MIS and MIA are mediated by distinct mechanisms.

Example 2

MOR1D is an Itch-Specific Receptor

Figure 2:
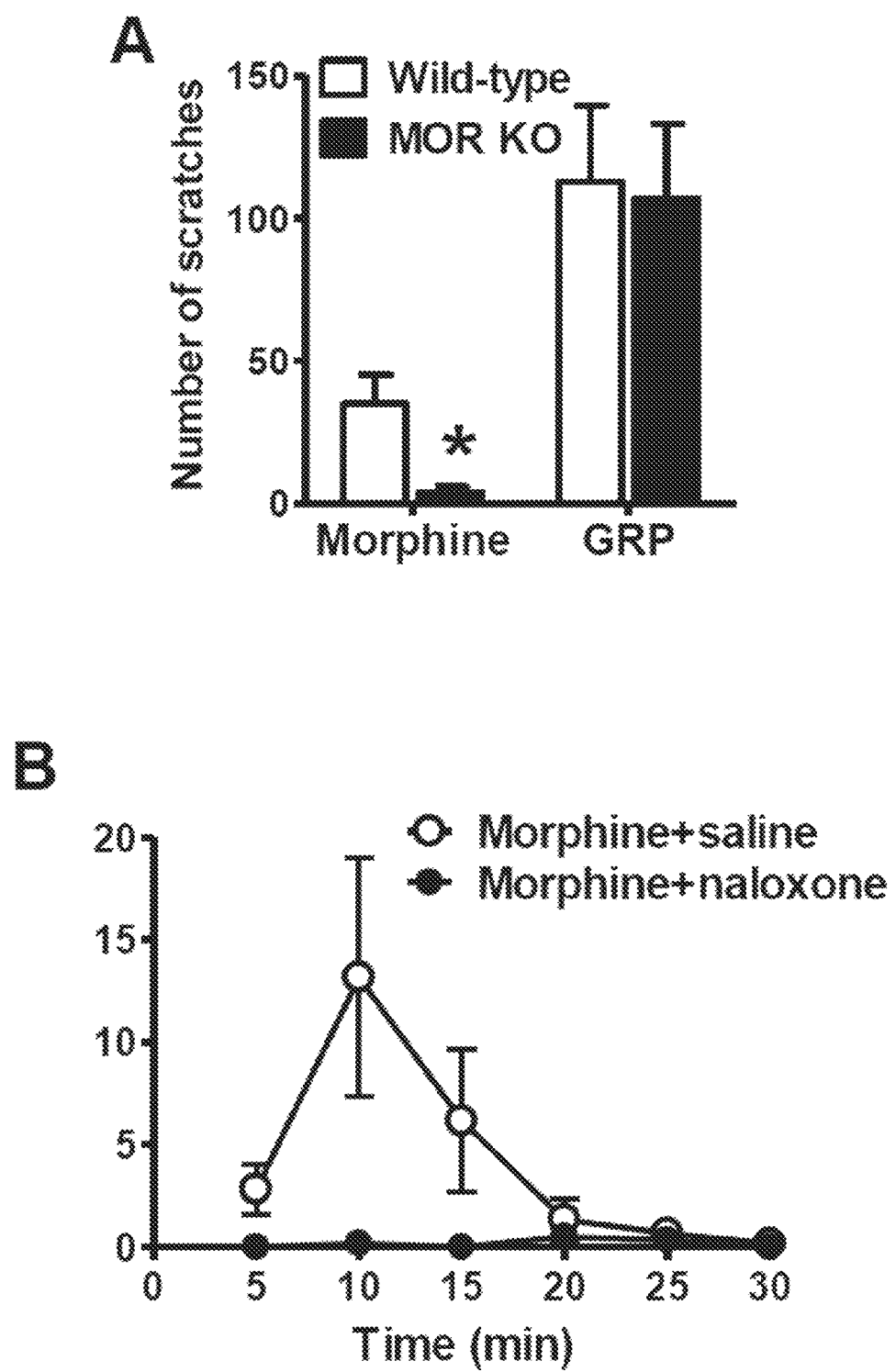
FIG. 2 Identification of MIA- and MIS-specific isoforms. (A) MIS was severely impaired in MOR KO mice, whereas GIS in MOR KO mice was comparable to that in wild-type littermate control mice. *$p<0.05$. (B) MIS was significantly reduced by naloxone (3 mg/kg, s.c.). $p<0.05$. (C) Schematic representation of partial alternative MOR splicing in the mouse. Clear rectangles represent the targeting exons by siRNA. (D) MIS was significantly reduced by MOR siRNA targeting at exon 1 (MOR1, 1C, 1D, and 1E) and exon 9 (MOR1C, 1D, and 1E), but not by siRNA targeting at exon 4 (MOR1) or exon 7 (MOR1C and 1E). *$p<0.05$. Sequence of siRNAs are included in supplementary file. (E) MOR siRNA targeting at exon 1 (MOR1, 1C, 1D, and 1E) and exon 4 (MOR1), but not exon 7 (MOR1C and 1E) or exon 9 (MOR1C, 1D, and 1E) significantly reduced morphine analgesic effect. *$p<0.05$. (F) Representative gel images showing decreased MOR1 mRNA level after exon 1 and exon 4 specific siRNA treatments and decreased MOR1D mRNA level after exon 1 and exon 9 specific siRNA treatments. 18S RNA, an internal control, was comparable among all groups. (G) Exon 1 and exon 4 specific siRNA significantly knocked down MOR1 mRNA in spinal cord as detected by q-RT-PCR.
Figure 2:
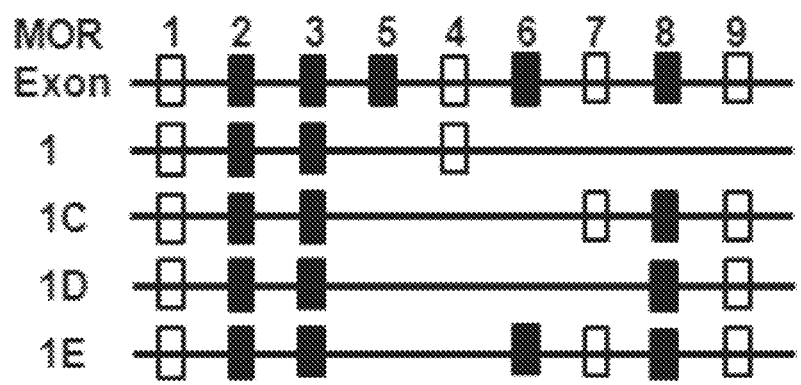
Figure 2:
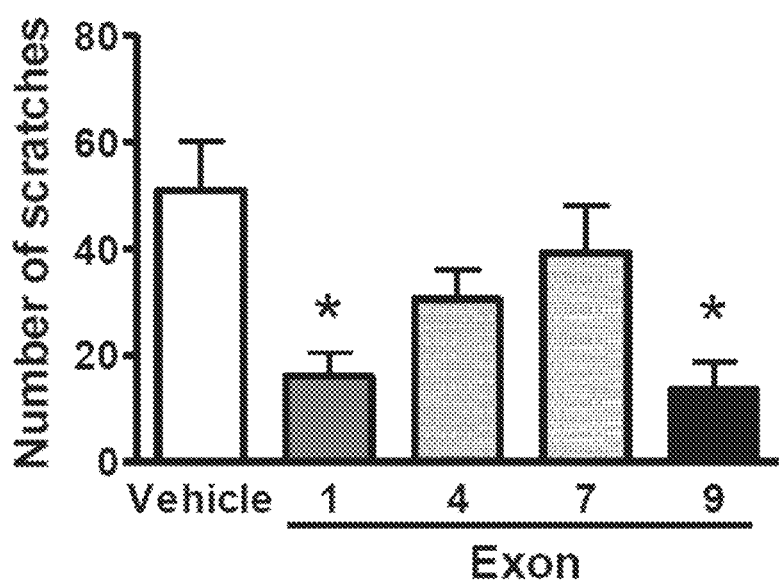
Figure 2:
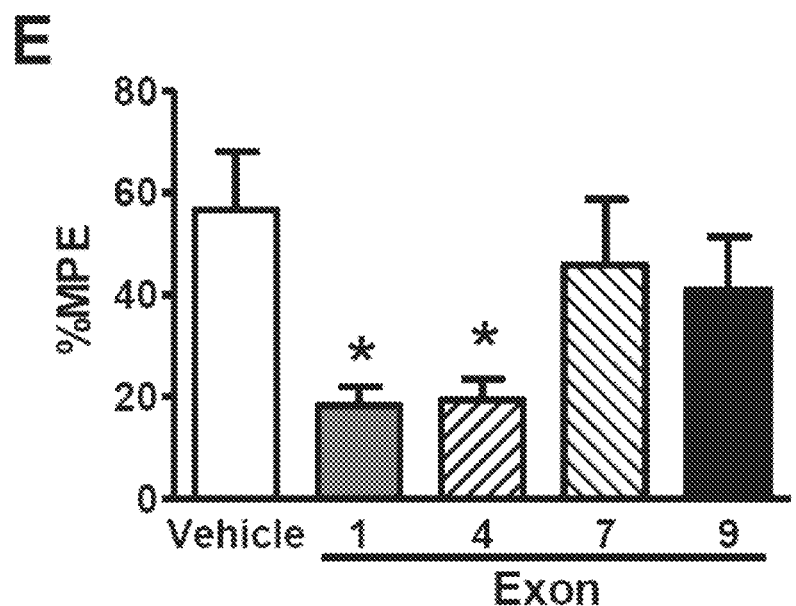
Figure 2:
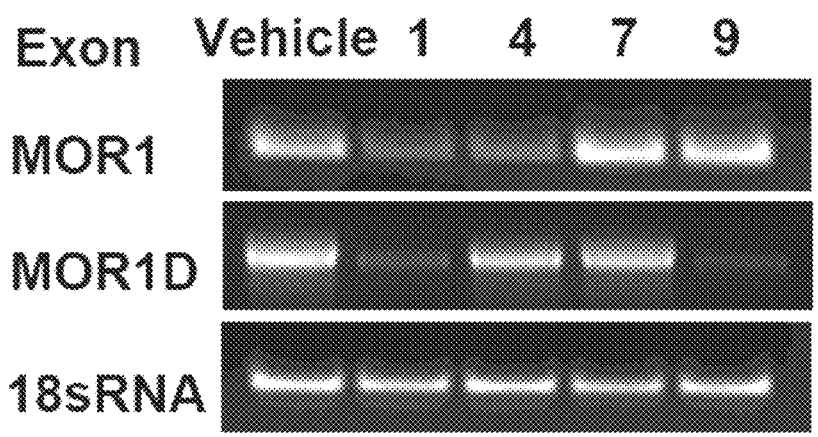
Figure 2:
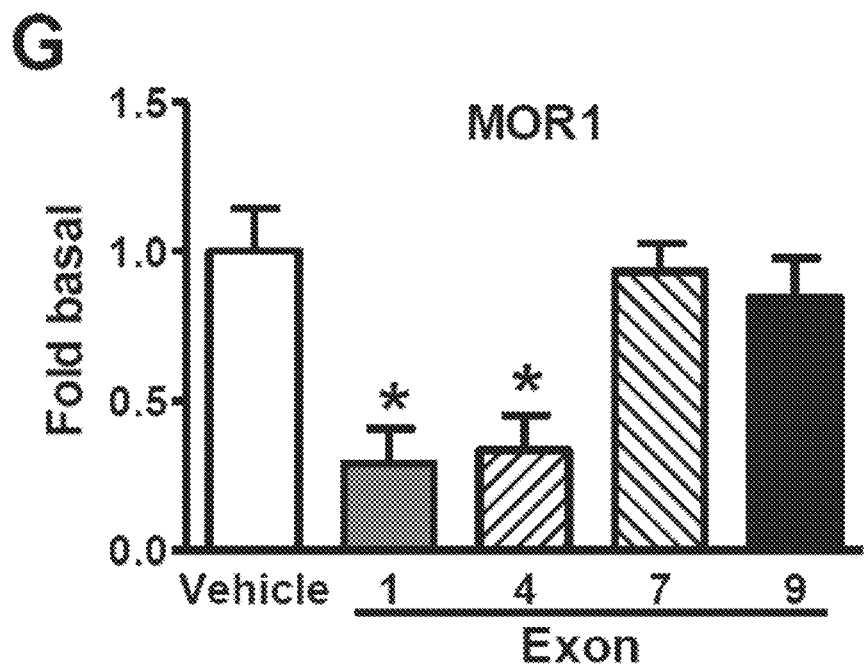
Figure 2:
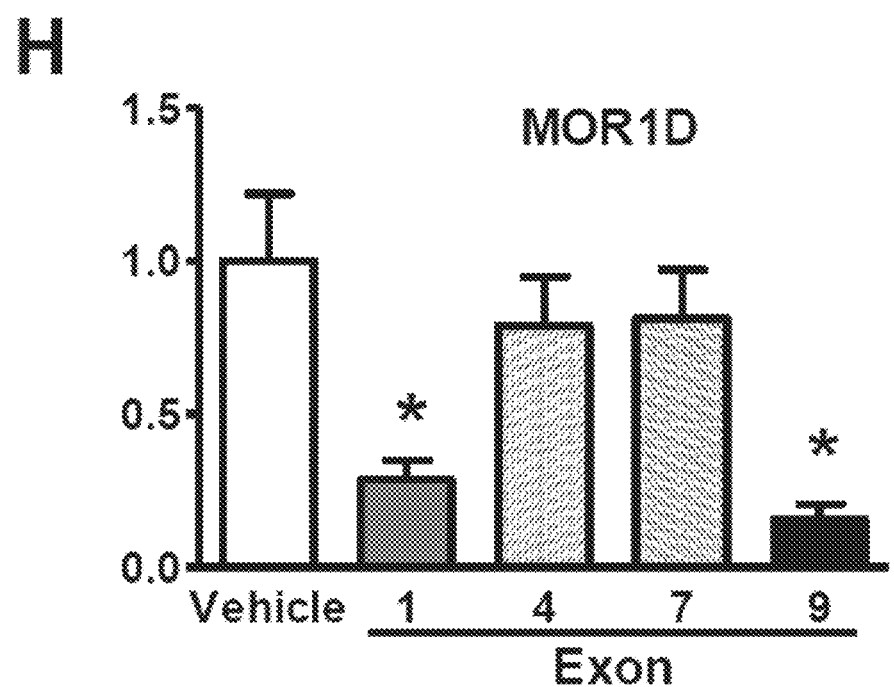

The finding that MIS is separable from MIA prompted further study of the molecular basis of disassociation of MIS and MIA. Mice lacking the Oprm gene displayed loss of MIA (Loh et al., 1998; Matthes et al., 1996; Sora et al., 1997), but whether the Oprm gene in the spinal cord is important for MIS has not been examined. We examined MIS in mice lacking the coding exons 2 and 3 of the Oprm gene (Loh et al., 1998), and found that MIS was nearly abolished in the MOR knockout mice, whereas gastrin-releasing peptide induced scratching (GIS) was not affected (FIG. 2A). Consistent with previous studies (Ballantyne et al., 1988; Ko et al., 2004), MIS was also abolished by naloxone, a non-specific MOR antagonist (FIG. 2B). The mouse Oprm gene encodes 16 coding exons, comprising dozens of spliced isoforms which primarily differ at C-terminus (Pan, 2005; Pasternak). For example, MOR1 comprises exon 1~4, while MOR1D of exons 1~3 and 8~9 (FIG. 2C). The multiplicity of the Oprm isoform system has been suggested to underlie the heterogeneoity and variability of analgesic and scratching effects exerted by different agonists (Andoh et al., 2008; Pasternak, 2004; Ravindranathan et al., 2009). It was postulated that different isoforms are responsible for MIS and MIA respectively. To test this, exon-specific siRNA knockdown experiment in the spinal cord of mice was performed, followed by examining the effect of knockdown on MIS. Knockdown of either exon 1 contained by the majority of MOR isoforms including MOR1, or exon 9 contained by isoforms 1C, 1D and 1E significantly attenuated MIS (FIG. 2D). In contrast, siRNA knockdown of exon 4 contained by MOR1 or exon 7 contained by 1C and 1E failed to reduce MIS significantly (FIG. 2D). Interestingly, knockdown of exon 1 or 4 markedly attenuated MIA, whereas knockdown of exon 7 or 9 had no effect on MIA (FIG. 2E).

Quantitative RT-PCR tests confirmed that spinal MOR1 mRNA was selectively decreased by exon 1 or exon 4 siRNA (FIGS. 2F and 2G), and spinal MOR1D mRNA was significantly reduced after exon 1 or exon 9 siRNA treatment (FIGS. 2F and 2H). In contrast, neither MOR1 nor MOR1D expression in DRG neurons was compromised by siRNA treatments (FIGS. 3A and 3B). To exclude the possibility that exon 9 siRNA might affect GRPR function, i.t. GIS was examined, and no significant reduction of GIS after MOR isoform knockdown was found (FIG. 3C). These results indicate that exon 9 is critical for MIS but not for MIA, whereas exon 4 is for MIA but not for MIS. Thus, spinal MOR1D has emerged as a MIS-specific isoform, whereas MOR1 possesses MIA-specific function.

Example 3

Co-Localization of GRPR and MOR1D in the Dorsal Horn of the Spinal Cord

To determine the expression pattern of MOR1D in the spinal cord of mice, a mouse antibody specifically against a unique MOR1D C-terminus was generated using the same strategy previously described, because a lack of cross-activity of MOR1D antibody with MOR1 antibody is well documented (Abbadie et al., 2000). Immunostaining using anti-MOR1D antibody indicates that MOR1D is expressed mainly in lamina I of the wild-type spinal cord (FIG. 4A and FIG. 5A), and no staining was observed in the spinal cord of MOR KO mouse (FIG. 5B). In contrast, MOR1 staining is largely restricted to lamina II with a few in lamina I (FIG. 4B). Importantly, no co-localization of MOR1 and MOR1D was detected in the spinal cord of mice (FIG. 4C). MOR1D and MOR1 antibody specifically recognized human embryonic kidney 293 (HEK 293) cells transfected with MOR1D and MOR1, respectively (FIG. 5B), and no cross activity was observed between the two antibodies. Together, these data validate the specificity of MOR1D antibody.

Next, it was examined whether MOR1D may overlap with GRPR expression. Double-staining of MOR1D and GRPR revealed that the expression of the two receptors overlaps in lamina I cells (FIGS. 4D-4F). In twenty-five sections across the lumbar spinal cord, approximately 31% of GRPR+ cells in lamina I were co-stained with MOR1D, and ~65% of MOR1D+ cells were co-stained with GRPR. No overlapping expression between GRPR and MOR1 was observed (FIGS. 4G-4I).

Example 4

Opioid-Induced Scratching was Abolished by the Blockade of the GRPR Function in the Spinal Cord To examine whether GRPR is important for mediating opioid-induced itch, MIS was compared between GRPR KO and wild-type mice. Strikingly, MIS was nearly abolished in GRPR KO mice (FIG. 6A). In contrast, no significant difference in MIA was observed between the groups (FIG. 6B). The abolition of MIS in GRPR KO mice was recapitulated when a highly selective MOR agonists, either DAMGO or fentanyl, was intrathecally injected (FIGS. 6C and 6E). Analgesic effects did not differ between GRPR KO and their littermate controls after DAMGO or Fentanyl treatment (FIGS. 6D and 6F). Consistently, it was also found that i.t. injection of a GRPR antagonist dramatically inhibited MIS (FIG. 6G), whereas MIA remained unchanged (FIG. 6H and FIG. 7A). These findings provide further evidence for the requirement of spinal GRPR in MIS, but not in nociceptive transmission. Importantly, the GRPR antagonist itself has no significant effect on acute pain as tested by tail immersion assay (FIG. 7B) and von Frey (FIG. 7C). These results suggest that GRPR is essential for mediating opioid-induced itch in mice, but not in opioid-mediated anti-nociception.

Example 5

Heterodimerization and Co-Internalization of MOR1D and GRPR

The co-expression of GRPR and MOR1D, along with their requirement for MIS, prompted the question of whether GRPR and MOR1D may physically interact through receptor heterodimerization, a mechanism commonly employed by GPCRs to increase their diverse pharmacological and physiological properties (Bouvier, 2001; Milligan, 2009). Co-immunoprecipitation (co-IP) was performed using extracts of HEK 293 cell expressing both Myc-tagged GRPR and HA-tagged MOR1D or both Myc-tagged GRPR and HA-tagged MOR1. Anti-HA antibody precipitated a band corresponding in size to Myc-GRPR in cells co-expressing Myc-GRPR and HA-MOR1D (FIG. 8A, L4), whereas no band was present in cells co-expressing MOR1 and GRPR (FIG. 8A, L3). Conversely, precipitation with anti-Myc antibody identified a band corresponding to HA-MOR1D in cells co-expressing GRPR and MOR1D (FIG. 8B, L4). This physical interaction is specific to MOR1D because HA-MOR1 was not precipitated by anti-Myc antibody in cells co-expressing GRPR and MOR1 (FIG. 8B, L3). To examine the physical interaction of MOR1D and GRPR in vivo, co-IP experiments were performed using the spinal cord membrane preparation. GRPR co-precipitated with MOR1D (FIG. 8C, L3), but not by MOR1 antibody or an irrelevant rabbit IgG (FIG. 8C, L2). Together, these results indicate that physical interactions between GRPR and MOR1D exist both in vitro and in vivo.

To test whether MOR1D may cross-activate GRPR and internalized with GRPR in response to morphine, internalization of Myc-tagged GRPR was first examined in HEK 293 cells stably expressing either MOR1D and GRPR or MOR1 and GRPR after morphine stimulation. Morphine failed to induce GRPR internalization in cells expressing GRPR alone (FIGS. 8D and 8E) or in cells co-expressing MOR1 and GRPR (FIGS. 8F and 8G). In contrast, GRPR internalization was significantly enhanced in HEK 293 cells co-expressing MOR1D and GRPR (FIGS. 8F and 8G). Consistent with a previous study (Whistler et al., 1999), no internalization of HA-MOR1 by morphine was found, regardless of whether cells express MOR1 only (FIGS. 8D and 8E) or co-express GRPR (FIGS. 8F and 8G). However, cells expressing MOR1D (FIGS. 8D and 8E) or MOR1D and GRPR (FIGS. 8F and 8G) showed significant MOR1D internalization in response to morphine. Both MOR1 and MOR1D were internalized in the presence of DAMGO, regardless of whether GRPR was present (FIG. 9). These results suggest that the co-existence of GRPR and MOR1D is a prerequisite for morphine-mediated GRPR internalization.

Next it was assessed whether naloxone would affect morphine-induced MOR1D-GRPR internalization. Naloxone inhibited morphine-induced GRPR or MOR1D internalization in a dose-dependent manner and at a dose of 10 μM could nearly abolish MOR1D-GRPR internalization (FIG. 8H). Interestingly, the GRPR antagonist inhibited morphine-induced internalization of GRPR but not MOR1D (FIG. 8I). Consistently, GRP was able to internalize GRPR, regardless of whether GRPR were co-expressed with MOR1D or MOR1

(FIG. 8D-G). However, neither MOR1D nor MOR1 internalized upon GRP stimulation, regardless of whether they were co-expressed with GRPR (FIG. 8D-G). Taken together, these results indicate that despite co-expression of MOR1D and GRPR, they cannot be reciprocally activated; only MOR1D is able to cross-activate GRPR in response to morphine, not vice versa.

Example 6

Cross-Activation of the GRPR Signaling Transduction Pathway by MOR1D Upon Morphine Stimulation GRPR can activate multiple signaling pathways including the phospholipase C (PLC)/inositol 1,4,5-trisphosphate (IP3)/Ca2+ signaling pathway in response to GRPR agonists in a number of heterologous cell lines (Jensen et al., 2008; Kroog et al., 1995). To examine whether GRPR-dependent calcium response might be cross-activated by morphine, Ca2+ signals were examined in HEK 293 cells expressing various combinations of MOR1, MOR1D and GRPR using calcium imaging. Both morphine and GRP induced calcium spikes in cells co-expressing MOR1D and GRPR (FIG. 10A), suggesting an activation of GRPR by morphine or GRP. Morphine- or GRP-induced calcium signals were not affected in calcium free extracellular buffer, indicating the endoplasmic reticulum origin of the calcium (FIG. 11A). However, morphine failed to evoke Ca2+ spikes in cells co-expressing MOR1 and GRPR or in cells containing only GRPR; neither morphine nor GRP generated a calcium response in cells expressing MOR1D alone (FIG. 10A).

To ascertain whether morphine-induced calcium spike is a consequence of a cross-activation of GRPR, cells co-expressing MOR1D and GRPR were pretreated with the GRPR antagonist or naloxone. Morphine-induced calcium spike was blocked by the GRPR antagonist and naloxone (FIG. 10B). GRP-induced calcium spikes were completely blocked by the GRPR antagonist and significantly reduced by naloxone (FIGS. 10B and 10D). Both morphine- and GRP-evoked Ca2+ increase were blocked by U73122 (a selective PLC inhibitor that prevents IP3 liberation) or 2-APB (an IP3 receptor (IP3R) antagonist), while U73343 (an inactive structural analog control for U73122) had no effect on calcium response to morphine or GRP (FIG. 10C). This data provides further support that morphine cross activates GRPR through MOR1D as well as the PLC/IP3/Ca2+ signaling pathway.

Example 7

Co-Expression of PLCβ Isoforms, IP3R3 and GRPR in the Spinal Cord

A prerequisite for PLC and IP3R signaling molecules to act downstream of GRPR is that they are co-expressed in GRPR+ cells. To circumvent the difficulties of double staining each individual PLC and IP3R isoform with GRPR, advantage was taken of mice whose GRPR neurons-+ are ablated specifically in the spinal cord by bombesin-saporin treatment (Sun et al., 2009), and qRT-PCR was used to compare the mRNA change of individual isoforms in the superficial dorsal horn between mice treated with bombesin-saporin and with blank-saporin. As confirmed by the significant decrease of GRPR mRNA (FIG. 11B), there was a complete loss of PLCβ3 expression and a significant decrease of PLCβ1, IP3R type 3 (IP3R3) and MOR1D mRNA in bombesin-saporin treated tissues as compared to the control (FIGS. 10E, 10F and 11B). These results reveal co-expression of PLCβ1/3, IP3R3, MOR1D and GRPR.

Example 8

Inhibition of PLC/IP3 Signaling Significantly Attenuates MIS but not MIA

Figure 10L:
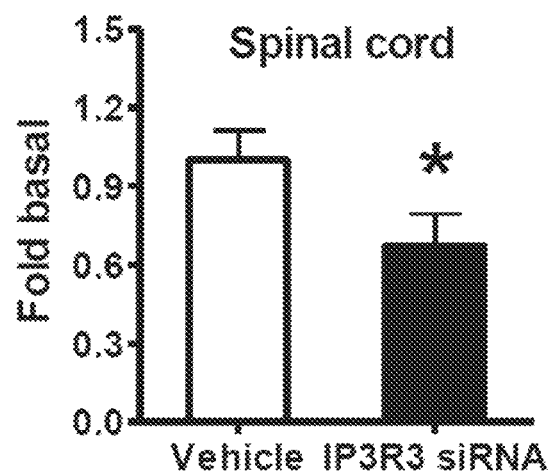

To determine the physiological relevance of morphine-induced signaling transduction in vivo, a spinal siRNA knockdown approach was employed to investigate whether PLC/IP3 signaling is important for MIS. Consistently, siRNA knockdown of PLCβ1/3 and IP3R3 in mice all compromised MIS (FIGS. 10G and 10J). In contrast, the same treatments did not alter MIA (FIGS. 10H and 10K). The efficiency and selectivity of siRNA were determined by qRT-PCR. Spinal PLC and IP3R3 mRNA level was significantly knocked down by approximately 62% and 33%, respectively (FIGS. 10I and 10L). No significant knockdown of the PLCβ and IP3R3 mRNA in DRG neurons was observed (FIGS. 11C and 11D).

I.t. injection of U73122 significantly attenuated MIS compared to the vehicle (FIG. 11E). Interestingly, a blockade of PLC with U73122 did not impact MIA (FIG. 11F). I.t. injection of 2-APB markedly reduced MIS (FIG. 11G), but it had no effect on MIA (FIG. 11H). Collectively, these data provide in vivo evidence that the PLC/IP3 signaling is important for MIS but dispensable for MIA.

Example 9

MOR1D C-Terminus is Critical for MIS and MOR1D and GRPR Heterodimeric Interaction The difference between MOR1 and MOR1D isoforms lies in a motif consisting of seven amino acids (RNEEPSS; SEQ ID NO:82) in MOR1D C-terminus (FIG. 12A). This motif is likely to be essential for MOR1D and GRPR physical interaction. To test this, a Tat-fusion peptide (Tat-MOR1DCT) containing a Tat (YGRKKRRQRRR; SEQ ID NO:496), a trans-activating domain of HIV protein that can permeate cell membrane (Schwarze et al., 1999), and the RNEEPSS (SEQ ID NO:82) motif was synthesized (FIG. 12A) and injected into the spinal cord. Introduction of Tat-MOR1DCT permits its competition with MOR1D for physical contacts with GRPR in vivo. Remarkably, i.t. injection of Tat-MOR1DCT specifically blocked MIS, while leaving GIS (FIG. 12B) and MIA (FIG. 12C) unperturbed. Subsequent co-IP analysis using the membrane extracts of the spinal cord injected with Tat-MOR1DCT and the vehicle revealed that Tat-MOR1DCT significantly reduced the amount of GRPR precipitated by MOR1D antibody relative to the vehicle (FIGS. 12D and 12E). These results demonstrate that MOR1D C-terminus is critical for MOR1D-GRPR dimerization and MIS.

Discussion for Examples 1-9.

This study presents molecular, cellular, biochemical and behavioral data that demonstrate uncoupling of opioid-induced itch and opioid-induced anti-nociception in the spinal cord. Functionally, morphine tolerance tests show no correlation between MIA and MIS. At the molecular level, MOR1D was identified as an isoform critical for mediating MIS but not MIA, whereas the MOR1 isoform is required for MIA but not MIS. At the cellular level, we show that MOR1D expression is largely restricted to lamina I and overlaps with GRPR, whereas MOR1 is mainly located in lamina II in the spinal cord. MOR1D is the first identified MOR isoform that does not possess the cardinal function of an opioid receptor.

These data argue against the prevailing view that opioid induces itch as result of pain inhibition, and uncover that opioid-induced itch is an active process, independently initiated by MOR1D-mediated activation of GRPR. Coupled with the finding that MIA remains unaffected in GRPR KO mice, the present studies further support the finding that GRPR is an itch-specific receptor (Sun and Chen, 2007) and GRPR-expressing neurons represent a labeled line for itch in the spinal cord (Sun et al., 2009).

Unidirectional Cross Activation of GRPR by MOR1D Through Heterodimeric Interactions GRP is an itch-specific peptide that is presumably released from primary afferents to activate spinal GRPR in response to pruritic stimuli (Sun and Chen, 2007). Spinal morphine may promote presynaptic release of GRP to activate central GRPR signaling. Several observations, however, suggest that GRP is dispensable for morphine-induced activation of GRPR. First, MOR antagonist naloxone abolished MIS but did not change GIS. Consistently, GIS is normal in MOR KO mice. Second, in HEK 293 cells expressing both MOR1D and GRPR, GRP failed to cause MOR1D internalization. These results indicate that the activation of GRPR in response to morphine is mediated via a postsynaptic mechanism. Indeed, MOR1D and GRPR dimers are detectable by co-immunoprecipitation in heterologous cells, and MOR1D and GRPR can also be co-immunoprecipitated from spinal cord membrane preparation. Thus, spinal opiates produce itch through MOR1D and GRPR heterodimerization. Importantly, in vivo interference with Tat-MOR1Dct markedly reduces co-immunoprecipitation of GRPR and MOR1D and blunts MIS. Taken together, these data demonstrate the importance of physical interactions between MOR1D and GRPR in MIS.

Calcium imaging studies illustrate that neither GRPR nor MOR1D alone are able to elicit a calcium response to morphine. Strikingly, a blockade of PLCβ and IP3R abolished morphine-induced calcium signaling in cells co-expressing MOR1D and GRPR. These results are in accord with previous observations that the ability of the Gi-coupled receptors to evoke calcium signaling often depends on a concomitant activation of the Gq-coupled receptors (Samways and Henderson, 2006). Distinguished from previous studies, the present study provides behavioral relevance for the PLCβ/IP3-dependent Ca2+ signaling evoked by morphine: siRNA knockdown shows that PLCβ1/β3 and IP3R3 are critical signaling transduction components required for MIS but not for MIA. Interestingly, PLCβ3 in DRG neurons has been shown to be required for MIA (Xie et al., 1999) as well as for histaminergic itch (Han et al., 2006). The fact that spinal opioid-induced itch is histamine-independent (Ko et al., 2004), along with the finding in the present studies that no change of PLCβ and IP3R occurs in DRG neurons by siRNA knockdown, indicates that the canonical PLCβ/IP3/Ca2+ signal transduction pathway in the spinal cord is itch-specific, and is different from its function in DRG neurons.

GPCR heterodimerization synergistically modulates respective receptor activity, resulting in either enhanced or inhibited ligand binding properties, or conferring novel function not originally possessed by the singular receptors (George et al., 2000; Jordan and Devi, 1999; Lopez and Salome, 2009). In contrast to reciprocal regulation of each receptor by respective agonists commonly found in GPCR heterodimerization, which allows for coincidental detection, the results in the present studies uncover a unidirectional signaling model for GPCR crosstalk: while morphine-encoded encoded itch information is transmitted from MOR1D to GRPR, GRP-encoded itch signaling cannot be reversely relayed to MOR1D by GRPR. Interestingly, the observation that MOR1D-GRPR co-immunoprecipitated band from spinal cord membrane preparation is detected in the absence of morphine stimulation indicates a constitutive presence of MOR1D-GRPR heterodimeric assembly in vivo. How can GRPR be activated and internalized by morphine via MOR1D, whereas MOR1D cannot be internalized by GRP? One can envision that MOR1D and GRPR heterodimers may exist in a relatively unstable and dynamic equilibrium state that can be either strengthened/activated upon morphine stimulation, resulting in a co-internalization, or weakened in response to GRP, leading to a dissociation of heterodimers so that only GRPR internalizes. This is reminiscent of agonist-dependent dimerization and internalization of the δ opioid receptor (Cvejic and Devi, 1997), and may also explain why the GRPR antagonist blocks morphine-mediated GRPR but not MOR1D endocytosis. Such a unidirectional signaling may ensure that opioid-encoded itch information is correctly relayed to the GRPR-signaling machinery, and avoid accidental engagement of MOR1D that may result in inappropriate signaling in a condition when GRPR is activated by GRP released from primary afferents. This one-way communication mechanism allows for added versatility to the physiological significance for GPCR heterodimerization, and enables opioid receptors to carry out an unorthodox function.

Why has such a mechanism evolved to permit cross activation of itch signaling by opioids? One plausible explanation is that opioid-induced pruritus may serve as the body's warning sign for opiate overdose or for internal metabolism disorders. For example, patients with cholestasis often suffer from terrible pruritus, which has been attributable to enhanced endogenous opioidergic signaling that is centrally mediated because opiate antagonists could ameliorate cholestasic itch, along with several other systemic itch conditions (Bergasa, 2005; Jones and Bergasa, 1990; Metze et al., 1999).

The present study raises important questions. For example, are the classic signaling molecules (e.g. Gβγ, adenylyl cyclase, K channel etc) of the Gi-coupled MOR receptor also involved? Our study cannot exclude this possibility that MOR1D may additionally regulate GRPR signaling through intracellular cross talks. In this regard, MIS provides a reliable, unique and unparalleled behavioral paradigm for facilitating further dissection of detailed intracellular signaling mechanisms of MOR1D and GRPR interactions and for understanding the corresponding physiological relevance.

Uncoupling of Itch and Pain: Therapeutic Implications

The identification of itch-specific MOR1D may shed light into the physiological and therapeutic relevance of the multiplicity of the MOR system. Although opiate antagonists may be used clinically to ameliorate spinal opioid-induced itch, their undiscriminating actions on both MOR1D and MOR1 might hinder opioid analgesia (Szarvas et al., 2003). The finding in the present studies, which couples MIS and MIA, enables new therapeutic strategies. Pharmacological or antibody disruption of GPCR heterodimerization may be a highly cell type-specific targeting approach (Agnati et al., 2003; Hipser et al.; Waldhoer et al., 2005), and the unique C terminus of MOR1D may be one of the best therapeutic targets. This heterodimeric-specific approach would not perturb the normal function of GRPR or MOR1D in other tissues where they are singularly expressed and where their physiological function may be important. Likewise, if MOR1D-GRPR signaling were involved in cholestsic itch, such a specific blockade may overcome side effects such as withdrawal-like symptoms often associated with the use of opioid antagonists in cholestsic itch (Bergasa, 2005). The present study implies that the physiological significance of multiple MOR isoforms may go beyond their normal anti-nociception paradigm that has been primarily restricted to the heterogeneity of opioid analgesia and patients (Pasternak, 2010). Although the disassociation between centrally mediated MIA and non-neural tissue-mediated side effects of opioids has been reported (Ling et al., 1989; Manara et al., 1986), it is much more difficult to separate MIA from the side effect originating centrally. In this regard, an interesting question arises as to whether MOR1D may mediate other types of opiate side effects since it is expressed in other brain areas such as the nucleus of the solitary tract, in which no co-localizatoin with MOR1 has been found (Abbadie et al., 2000). The uncoupling of MIA and MIS underscores the necessity of elucidating the function of individual MOR isoforms, which may promise novel pain therapy without debilitating side effects.

Materials and Methods for Examples 1-9.

Animals.

Generation and genotyping of GRPR KO and MOR KO were described previously (Hampton et al., 1998; Loh et al., 1998). All the experiments were performed in accordance with the guidelines of the National Institutes of Health and were approved by the Animal Studies Committee at Washington University School of Medicine. Male GRPR KO mice, MOR KO mice, their wild-type littermate mice and C57BL/6J mice aged between 7 and 12 weeks were used for experiments. All behavioral tests were done by observers blinded to the treatment or genotype of animals.

Drugs and Reagents.

Morphine, DAMGO, fentanyl, GRP, naloxone, bombesin-saporin (Advanced Targeting), the GRPR antagonist (D-Phe-6-Bn(6-13)OMe), U73122, U73343, 2-APB, siRNA (Sigma), Tat-MOR1 DCT and sequence-scrambled control peptide were administered intrathecally. Morphine, DAMGO, fentanyl, GRP, naloxone, bombesin-saporin (Advanced Targeting) and the GRPR antagonist, D-Phe-6-Bn(6-13)OMe was dissolved in sterile saline. U73122 and U73343 were dissolved in 10% DMSO. 2-APB was dissolved in 2% ethanol. The drugs were administered intrathecally at a volume of 5 µl. Small interfering RNA (siRNA, Sigma-Aldrich) were dissolved in DEPC-treated PBS containing 15% ExGen 500 in vivo transfection reagent (Fermentas) and administered intrathecally at a volume of 5 µl. Tat-fusion peptide Tat-MOR1 DCT (YGRKKRRQRRRRNEEPSS; SEQ ID NO:568) and sequence-scrambled control peptide (YGRKKRRQRRRSEPNSER; SEQ ID NO:569) were synthesized by NeoBioScience and dissolved in saline.

Behavior.

Scratching behavior and tail immersion assay were performed as previously described (Sun and Chen, 2007). All tail-flick results were expressed as percentage of maximum possible effect [% MPE=(post drug latency−pre drug latency)×100/(cutoff time−pre drug latency)]. Morphine antinociceptive tolerance was induced as described (Fairbanks and Wilcox, 1999) (Zhao et al., 2007).

Scratching Behavior.

Itch behavioral tests were performed as previously described (Sun and Chen, 2007). Briefly, prior to experiments, mice were given 30 min to acclimate to a small plastic chamber (15×26×12 cm). Mice were then briefly removed from the chamber and given i.t. injections of morphine, DAMGO or fentanyl. I.t. injections into the lumbar region of unanesthetized mice were performed as described previously (Hylden and Wilcox, 1980). The number of scratching responses was counted for 30 min at 5-min intervals. One scratch is defined as a lifting of the hind limb towards the body and then a replacing of the limb back to the floor, regardless of how many scratching strokes take place between those two movements. Antagonists or inhibitors were given 15 min prior to morphine.

Tail Immersion Assay.

Warm water tail immersion assay was conducted as described previously (Chen et al., 2001). Mice tails were dipped beneath the 50° C. water in a temperature-controlled water bath (IITC Inc.). The latency to withdrawal was measured with a 15-s cutoff. For opioid analgesia study, tail-flick results were expressed as percentage of maximum possible effect [% MPE=(post drug latency−pre drug latency)/100/(cutoff time−pre drug latency)].

Tolerance Induction.

Morphine antinociceptive tolerance was induced as described (Fairbanks and Wilcox, 1999; Zhao et al., 2007). For acute tolerance induction, mice were treated with morphine (100 mg/kg, s.c.) or equal amount of saline (100 µl, s.c.). Antinociception was assessed by tail immersion assay. Twenty-four hr after the morphine treatment, mice had returned to their basal nociceptive lantencies. Both groups of mice were then treated with morphine (0.3 nmol, i.t.) and scratching behavior was observed for 30 min. Tail-flick latency was recorded before and 30 min after intrathecal morphine injection. For chronic morphine tolerance induction, mice received daily morphine injections (10 mg/kg s.c. between 1500 and 1600) for 5 days. For assessment of tolerance, the antinociceptive effect of morphine was determined daily before and 30 min after the morphine injection by tail immersion assay as described above, and the effect of morphine (% MPE) was compared.

Complete Freund's Adjuvant (CFA) Model.

In CFA induced inflammatory pain, mice received an injection of CFA (20 µl, Sigma) into the plantar of the right hindpaw. Mechanical sensitivity was assessed using von Frey assay.

Von Frey Assay.

Mechanical sensitivity was assessed using a set of calibrated von Frey filaments (Stoelting). Each filament was applied 5 consecutive times and the smallest filament that evoked reflexive flinches of the paw on 3 of the 5 trials was taken as paw withdrawal threshold.

Preparation and I.T. Injection of siRNA.

Selective siRNA duplexes for mouse Oprm exons, PLCβ1/β3 and IP3R3 were purchased from Sigma. Sequence information or catalog number is listed in the Table 1.

|  | Sence Sequence/catalog number |
| --- | --- |
| Oprm exon 1 | SASI_Mm01_00187710 |
| Oprm exon 4 | UCUGGAAGCAGAAACUGCUuu (SEQ ID NO: 570) |
| Oprm exon 7 | AAACCCUGCAAGAGUUGCAuu (SEQ ID NO: 571) |
| Oprm exon 9 | UGAGGAACCUUCUUCCUGAuu (SEQ ID NO: 572) |
| PLC β1 | SASI_Mm01_00180965 |
| PLC β3 | SASI_Mm01_00178753 |
| IP3R3 | SASI_Mm01_00026614 |

Selective siRNA duplexes for mouse Oprm exons, PLCβ1/3 and IP3R3 were intrathecally injected daily for 3 consecutive days. Behavior testing and tissue harvest were carried out at 48 hr after the last injection. RNA was dissolved in diethyl pyrocarbonate-treated PBS and prepared immediately prior to administration by mixing the RNA solution with a transfection reagent, ExGen 500 (Fermentas). The final concentration of RNA was 1.25 µg/5 µl. siRNA or ExGen 500 alone (defined as vehicle) in 5 µl was delivered to the lumbar region of the spinal cord. The injection was given daily for 3 consecutive days (Luo et al., 2005; Tan et al., 2009). Behavior testing and tissue harvest were carried out 48 hr after the last injection.

Laser Capture Microdissection (LCM).

LCM were performed as previously described (van Baarlen et al., 2009) with minor modifications. Frozen sections (30 µm thickness) of the lumber spinal cord were cut at −20° C. and stored at −80° C. Immediately before LCM, the frozen sections were brought to room temperature for 1 min, and then fixed in 70% ethanol for 1 min, followed by washing in nuclease-free water. Then the slide was dehydrated in an ethanol/xylene gradient series: 10 dips in 70% ethanol, 2 times 10 dips in 95% ethanol, 10 dips in 100% ethanol, 1 min 100% ethanol, 10 dips in xylene, 2 times 1 min incubation in xylene. The sections were dried for 5~10 min at room temperature and kept in dry chamber with Drierite.

Laminae I&II of the spinal cord were dissected using the Pix-Cell II with HS caps (Arcturus). The settings were 100 mW, 1.2 mSec with a 30-µm laser beam.

Quantitative RT-PCR (qRT-PCR).

RNA was isolated from the LCM sample caps using the PicoPure RNA isolation kit (Arcturus) following manufacturer's recommendations. For DRG neurons, RNA was isolated using Trizol reagent (Invitrogen). For a reverse transcription reaction, 2 µg of RNA was used following manufacturer's recommendations (SuperScript II, Invitrogen). cDNA samples were stored at −20° C. Quantitative PCR amplification was performed in 96-well plates on an Mx3000 QPCR system (Stratagene). All samples were run in triplicate using an annealing temperature of 60° C. Primers sequences were listed in Table 2.

siRNA−$\Delta C_T$, for the vehicle. The equation, $2^{\Delta\Delta C_T}$, denotes the ratio of the level of target transcripts in the siRNA-treated group to the vehicle group. This number is converted to fold of control, where the control is set at 1.

Immunohistochemistry and Specificity Test of Rabbit anti-MOR1D.

Rabbit anti-MOR1D serum was generated using specific peptide HQRNEEPSS (SEQ ID NO:135) conjugated with KLH as previously described (Abbadie et al., 2000). To test the specificity of the antibody, floating frozen spinal sections of wild-type mice and MOR KO mice were used for immunostaining. HEK 293 cells expressing MOR1D or MOR1 were also used for immunostaining to test the specificity of rabbit anti-MOR1D and guinea pig anti-MOR1. For MOR1D/GRPR double staining, the sections were incubated with rabbit anti-MOR1D (1:10,000) in PBS containing 2% normal donkey serum and 0.3% Triton X-100 overnight followed by FITC-conjugated donkey anti-rabbit (1:400; Jackson) for 2 hr. After washing with PBS, sections were incubated with rabbit anti-GRPR antibody (MBL, 1:100) labeled with biotin (Invitrogen) for 2 hr at room temperature. Sections were briefly fixed in 4% paraformadehyde for 10 min. After washing, sections were incubated with Cy3-conjugated streptavidin (1:100, Jackson) for 2 hr. For MOR1/GRPR and MOR1D/MOR1 double staining, sections were incubated overnight at 4° C. with rabbit anti-GRPR (1:4000)/guinea pig anti-MOR1 (Chemicon, 1:2000) or rabbit anti-MOR1D (1:10,000)/guinea pig anti-MOR1 (1:2000). After washing, sections were incubated for 2 hr at room temperature with Cy3-conjugated donkey anti-rabbit secondary antibody (1:400, Jackson) and FITC-conjugated donkey anti-guinea pig secondary antibody (1:400, Jackson).

Generation of MOR1D antibody and Immunohistochemistry.

Rabbit anti-MOR1D antibody was generated using specific peptide HQRNEEPSS (SEQ ID NO:135) conjugated with KLH as previously described (Abbadie et al., 2000). Double staining was performed using standard protocols.

TABLE 2

|  | Forward primer | Reverse primer |
| --- | --- | --- |
| PLC β1 | 5'-GAGGAAGGCATTTACAACCAAG-3'<br>(SEQ ID NO: 573) | 5'-ACTGCTCTTGCCGAAGATTAAG-3'<br>(SEQ ID NO: 574) |
| PLC β3 | 5'-CTGATGGGCCGTATCCTG-3'<br>(SEQ ID NO: 575) | 5'-AGGAACTGCCCCGAAATC-3'<br>(SEQ ID NO: 576) |
| IP3R3 | 5'-GGGCGCAGAACAACGAGAT-3'<br>(SEQ ID NO: 577) | 5'-GAAGTTTTGCAGGTCACGGTT-3'<br>(SEQ ID NO: 578) |
| MOR1 | 5'-GTTCACCAGCATCTTCACG -3'<br>(SEQ ID NO: 579) | 5'-TGCATACCACTGCTCCATC -3'<br>(SEQ ID NO: 580) |
| MOR1D | 5'-ACCCAGTTCTTTATGCGTTC -3'<br>(SEQ ID NO: 581) | 5'-TCAGGAAGAAGGTTCCTCATTC-3'<br>(SEQ ID NO: 582) |
| GRPR | 5'-AGCAAGAGCTTCAGGAAGCAG-3'<br>(SEQ ID NO: 583) | 5'-CTAGACATACCCCTCATGACAG-3'<br>(SEQ ID NO: 584) |
| 18S RRNA | 5'-AAACGGCTACCACATCCAAG-3'<br>(SEQ ID NO: 585) | 5'-CCTCCAATGGATCCTCGTTA-3'<br>(SEQ ID NO: 586) |

Expression of target mRNA was normalized to expression of 18S rRNA. The differences in mRNA expression between treatments were analyzed using the Comparative $C_T$ Method (Gallup et al., 2005). The threshold cycle ($C_T$) is defined as the cycle at which the amount of amplified PCR product from the target cDNA reaches a fixed threshold. In each treatment, $\Delta C_T = C_T$ for the target−$C_T$ for GAPDH $\Delta\Delta C_T = \Delta C_T$ for the Cell Culture and Transfections.

The wild-type mouse GRPR receptor was tagged at the amino terminus with the Myc epitope tag sequence EQKLISEEDL (SEQ ID NO:587) using polymerase chain reaction and subcloned into a pcDNA3.1 expression vector (Invitrogen) containing a neomycin resistance. The wild-type mouse MOR1 and MOR1D receptors were tagged at the amino terminus with the HA epitope tag sequence YPYDVPDYA (SEQ ID NO:588) using polymerase chain reaction and subcloned into a pcDNA3.1 expression vector (Invitrogen) containing a hygromycin resistance. HEK293 cells were grown in Dulbecco's modified Eagle's medium supplemented with 10% fetal bovine serum in a humidified atmosphere containing 5% CO2. The cells were first transfected with plasmid containing the neomycin resistance by electroporation (GenePulserXcell, Bio-Rad). Stable transfectants were selected in the presence of 500 μg/ml G418 (Invitrogen). To generate lines co-expressing two differentially epitope-tagged receptors, the cells were subjected to a second round of transfection and selected in the presence of 500 μg/ml G418 and 100 μg/ml hygromycin (Roche). Clones expressing Myc-GRPR, HA-MOR1, HA-MOR1D, HA-MOR1/Myc-GRPR, and HA-MOR1D/Myc-GRPR were generated. Receptor expression was monitored using quantitative Western blot analysis to ensure that clones co-expressing about 1:1 ratio of GRPR and MOR were selected.

Co-Immunoprecipitation and Western Blot Analysis.

Protein Extraction.

HEK293 cells expressing MOR1D/GRPR or MOR1/GRPR were plated onto poly-D-lysine-coated 100-mm dishes and grown to 80% confluence. The cells were exposed to the cross-linking agents dithiobis-(succinimidylpropionate) (Pierce) and subsequently lysed as described (Koch et al., 2001). The cell membranes were prepared and solubilized in detergent buffer (50 mM Tris-HCl, pH7.4, 150 mM NaCl, 5 mM EDTA, 1% Nonidet P-40, 0.5% sodium deoxycholate, 0.1% SDS, and proteinase inhibitors). Lumbar spinal cord were dissected on ice and quickly frozen in −80° C. Membrane proteins were extracted as described (Liu et al., 2009). Samples were removed into a microtube containing ice-cold sample buffer (20 mM Tris-HCl [pH 7.4], 1 mM dithiothreitol, 10 mM NaF, 2 mM $Na_3VO_4$, 1 mM EDTA, 1 mM EGTA, 5 mM microcystin-LR, and 0.5 mM phenylmethylsulfonyl fluoride), and homogenized by sonication. Homogenates were centrifuged at 700×g for 10 min at 4° C. The supernatant was centrifuged at 40,000×g at 4° C. for 30 min to obtain the membrane pellet. The membrane was solubilized as described previously (Luo et al., 1997; Mao et al., 2005) in sample buffer containing 0.5% sodium deoxycholate. After incubation at 4° C. for 20 min, Triton X-100 was added to a final concentration of 0.5%. Insoluble proteins were sedimented at 50,000×g at 4° C. for 30 min. The supernatants were used for coimmunoprecipitation.

Co-Immunoprecipitation.

Two hundred μg of solubilized samples were incubated with a rabbit antibody against MOR1D, MOR1 (Neuromics) or HA (BD bioscience), or a mouse antibody against c-Myc (Covance) overnight at 4° C. The complex was precipitated with 50% protein A or G agarose/sepharose bead slurry (Amersham) for anti-HA and anti-Myc antibody. The precipitate was deglycosylated by PNGase F (NEB) for 1 hr at 37° C. For anti-MOR1D and anti-MOR1 antibody, the complex was precipitated with 50% TrueBlot™ anti-rabbit IgG bead slurry (eBioscience). The beads were washed four times in PBS with 0.3% Triton X-100 and boiled in LDS sample buffer (Invitrogen) with 50 mM dithiothreitol for 10 min.

Western Blot Analysis.

The equal amount of proteins were separated on SDS NuPAGE Bis-Tris 4-12% gels (Invitrogen) and transferred to polyvinylidene fluoride membrane (Invitrogen). The blots were blocked in blocking buffer (5% nonfat dry milk in PBS and 0.1% Tween 20) for 1 hr at room temperature and incubated with mouse anti Myc (1:1,000), rabbit anti HA (1:1,000), rabbit anti-MOR1D (1:10,000), rabbit anti-GRPR (1:10,000), rabbit anti-MOR1 (1:10,000), rabbit anti-PLCβ3 (1:10,000; kindly provided by Prof. Paul Sternweis) or mouse anti-IP3R3 (1:1,000; kindly provided by Prof. Emily Liman) for 16 hr at 4° C. This was followed by 1 h incubation in goat horseradish peroxidase-linked secondary antibodies (Santa Cruz) at 1:2,500. Immunoblots were developed with the enhanced chemiluminescence reagents (Amersham).

Internalization Assays.

ELISA:

The receptor internalization assay was performed as described previously (Pfeiffer et al., 2002). Briefly, cells in poly-D-lysine-treated 24-well plates were preincubated with primary antibody of mouse anti-Myc or rabbit anti-HA at 1 μg/ml) for 2 hr at 4° C., followed by the treatment with agonist (1 μM) in OPTIMEM (Invitrogen) or OPTIMEM alone for 30 min. Subsequently, cells were fixed and incubated with the peroxidase conjugated secondary antibody (Santa Cruz, 1:1000) for 2 hr. After washing, the plates were developed with 300 μl of ABTS solution. After 20 min, 250 μl of the substrate solution from each well was transferred to a 96-well plate and analyzed at 405 nm using a microplate reader.

Immunofluorescence Staining:

The staining assay was performed as described previously (Koch et al., 2001). Briefly, cells were grown on poly-D-lysine-treated coverslips overnight. After washing, the cells were incubated with rabbit anti-HA or mouse anti-Myc for 2 hr at 4° C. to label cell surface receptors. The cells were subsequently exposed to 1 μM morphine or 1 μM GRP for 30 min at 37° C. to induce receptor endocytosis. The cells were then fixed with 4% paraformaldehyde for 40 min at room temperature and washed three times in PBS. Specimens were incubated for 3 min in 50% methanol and 3 min in 100% methanol, washed several times in PBS, and preincubated with PBS and 2% normal donkey serum for 1 hr at room temperature. Bound primary antibody was detected with FITC-conjugated donkey anti rabbit secondary antibody (1:200, Jackson) or Cy3-conjugated donkey anti mouse secondary antibody (1:400, Jackson).

Calcium Imaging.

The cells were grown on poly-D-lysine treated coverslips overnight and loaded with Fura 2-acetomethoxy ester (Molecular Probes) for 30 min at 37° C. After washing, cells were imaged at 340 and 380 nm excitation wavelengths to detect intracellular free calcium. Calibration was performed using Fura-2 Calcium Imaging Calibration Kit (Invitrogen) following manufacturer's instruction. Each experiment was done at least three times, and at least 50 cells were analyzed each time.

Statistical Analysis.

Statistical comparisons were performed with two-way analysis of variance (ANOVA) or Student's t-test. All data were expressed as the mean±standard error of the mean (s.e.m.) and error bars represent s.e.m. $P<0.05$ was considered statistically significant.

REFERENCES

1. Abbadie, C., Pan, Y., Drake, C. T., and Pasternak, G. W. (2000). Comparative immunohistochemical distributions of carboxy terminus epitopes from the mu-opioid receptor splice variants MOR-1D, MOR-1 and MOR-1C in the mouse and rat CNS. Neuroscience 100, 141-153.
2. Agnati, L. F., Ferre, S., Lluis, C., Franco, R., and Fuxe, K. (2003). Molecular mechanisms and therapeutical implications of intramembrane receptor/receptor interactions among heptahelical receptors with examples from the striatopallidal GABA neurons. Pharmacol Rev 55, 509-550.

3. Alvarez, V. A., Arttamangkul, S., Dang, V., Salem, A., Whistler, J. L., Von Zastrow, M., Grandy, D. K., and Williams, J. T. (2002). mu-Opioid receptors: Ligand-dependent activation of potassium conductance, desensitization, and internalization. J Neurosci 22, 5769-5776.
4. Andoh, T., Yageta, Y., Konno, M., Yamaguchi-Miyamoto, T., Takahata, H., Nojima, H., Nemoto, H., and Kuraishi, Y. (2008). Evidence for separate involvement of different mu-opioid receptor subtypes in itch and analgesia induced by supraspinal action of opioids. J Pharmacol Sci 106, 667-670.
5. Ballantyne, J. C., Loach, A. B., and Carr, D. B. (1988). Itching after epidural and spinal opiates. Pain 33, 149-160.
6. Bergasa, N. V. (2005). The pruritus of cholestasis. J Hepatol 43, 1078-1088.
7. Bouvier, M. (2001). Oligomerization of G-protein-coupled transmitter receptors. Nat Rev Neurosci 2, 274-286.
8. Carstens, E. (1997). Responses of rat spinal dorsal horn neurons to intracutaneous microinjection of histamine, capsaicin, and other irritants. J Neurophysiol 77, 2499-2514.
9. Carstens, E. E., Carstens, M. I., Simons, C. T., and Jinks, S. L. (2010). Dorsal horn neurons expressing NK-1 receptors mediate scratching in rats. Neuroreport 21, 303-308.
10. Chaney, M. A. (1995). Side effects of intrathecal and epidural opioids. Can J Anaesth 42, 891-903.
11. Chen, Z. F., Rebelo, S., White, F., Malmberg, A. B., Baba, H., Lima, D., Woolf, C. J., Basbaum, A. I., and Anderson, D. J. (2001). The paired homeodomain protein DRG11 is required for the projection of cutaneous sensory afferent fibers to the dorsal spinal cord. Neuron 31, 59-73.
12. Cvejic, S., and Devi, L. A. (1997). Dimerization of the delta opioid receptor: implication for a role in receptor internalization. J Biol Chem 272, 26959-26964.
13. Davidson, S., and Giesler, G. J. (2010). The multiple pathways for itch and their interactions with pain. Trends Neurosci 33, 550-558.
14. Davidson, S., Zhang, X., Yoon, C. H., Khasabov, S. G., Simone, D. A., and Giesler, G. J., Jr. (2007). The itch-producing agents histamine and cowhage activate separate populations of primate spinothalamic tract neurons. J Neurosci 27, 10007-10014.
15. Fairbanks, C. A., and Wilcox, G. L. (1999). Spinal antinociceptive synergism between morphine and clonidine persists in mice made acutely or chronically tolerant to morphine. J Pharmacol Exp Ther 288, 1107-1116.
16. Gallup, J. M., Kawashima, K., Lucero, G., and Ackermann, M. R. (2005). New quick method for isolating RNA from laser captured cells stained by immunofluorescent immunohistochemistry; RNA suitable for direct use in fluorogenic TaqMan one-step real-time RT-PCR. Biol Proced Online 7, 70-92.
17. George, S. R., Fan, T., Xie, Z., Tse, R., Tam, V., Varghese, G., and O'Dowd, B. F. (2000). Oligomerization of mu- and delta-opioid receptors. Generation of novel functional properties. J Biol Chem 275, 26128-26135.
18. Hales, P. (1980). Pruritus after epidural morphine. Lancet 2, 204.
19. Hampton, L. L., Ladenheim, E. E., Akeson, M., Way, J. M., Weber, H. C., Sutliff, V. E., Jensen, R. T., Wine, L. J., Arnheiter, H., and Battey, J. F. (1998). Loss of bombesin-induced feeding suppression in gastrin-releasing peptide receptor-deficient mice. Proc Natl Acad Sci USA 95, 3188-3192.
20. Han, S. K., Mancino, V., and Simon, M. I. (2006). Phospholipase Cbeta 3 mediates the scratching response activated by the histamine H1 receptor on C-fiber nociceptive neurons. Neuron 52, 691-703.
21. Hipser, C., Bushlin, I., Gupta, A., Gomes, I., and Devi, L. A. Role of antibodies in developing drugs that target G-protein-coupled receptor dimers. Mt Sinai J Med 77, 374-380.
22. Hylden, J. L., and Wilcox, G. L. (1980). Intrathecal morphine in mice: a new technique. Eur J Pharmacol 67, 313-316.
23. Ikoma, A., Steinhoff, M., Stander, S., Yosipovitch, G., and Schmelz, M. (2006). The neurobiology of itch. Nat Rev Neurosci 7, 535-547.
24. Jensen, R. T., Battey, J. F., Spindel, E. R., and Benya, R. V. (2008). International Union of Pharmacology. LXVIII. Mammalian bombesin receptors: nomenclature, distribution, pharmacology, signaling, and functions in normal and disease states. Pharmacol Rev 60, 1-42.
25. Jones, E. A., and Bergasa, N. V. (1990). The pruritus of cholestasis: from bile acids to opiate agonists. Hepatology 11, 884-887.
26. Jordan, B. A., and Devi, L. A. (1999). G-protein-coupled receptor heterodimerization modulates receptor function. Nature 399, 697-700.
27. Keith, D. E., Murray, S. R., Zaki, P. A., Chu, P. C., Lissin, D. V., Kang, L., Evans, C. J., and von Zastrow, M. (1996). Morphine activates opioid receptors without causing their rapid internalization. J Biol Chem 271, 19021-19024.
28. Kieffer, B. L. (1999). Opioids: first lessons from knockout mice. Trends Pharmacol Sci 20, 19-26.
29. Ko, M. C., and Naughton, N. N. (2000). An experimental itch model in monkeys: characterization of intrathecal morphine-induced scratching and antinociception. Anesthesiology 92, 795-805.
30. Ko, M. C., Song, M. S., Edwards, T., Lee, H., and Naughton, N. N. (2004). The role of central mu opioid receptors in opioid-induced itch in primates. J Pharmacol Exp Ther 310, 169-176.
31. Koch, T., Schulz, S., Pfeiffer, M., Klutzny, M., Schroder, H., Kahl, E., and Hollt, V. (2001). C-terminal splice variants of the mouse mu-opioid receptor differ in morphine-induced internalization and receptor resensitization. J Biol Chem 276, 31408-31414.
32. Kroog, G. S., Jensen, R. T., and Battey, J. F. (1995). Mammalian bombesin receptors. Med Res Rev 15, 389-417.
33. Kuraishi, Y., Yamaguchi, T., and Miyamoto, T. (2000). Itch-scratch responses induced by opioids through central mu opioid receptors in mice. J Biomed Sci 7, 248-252.
34. Lagerstrom, M. C., Rogoz, K., Abrahamsen, B., Persson, E., Reinius, B., Nordenankar, K., Olund, C., Smith, C., Mendez, J. A., Chen, Z. F., et al. (2010). VGLUT2-dependent sensory neurons in the TRPV1 population regulate pain and itch. Neuron 68, 529-542.
35. Law, P. Y., Wong, Y. H., and Loh, H. H. (2000). Molecular mechanisms and regulation of opioid receptor signaling. Annu Rev Pharmacol Toxicol 40, 389-430.
36. Ling, G. S., Paul, D., Simantov, R., and Pasternak, G. W. (1989). Differential development of acute tolerance to analgesia, respiratory depression, gastrointestinal transit and hormone release in a morphine infusion model. Life Sci 45, 1627-1636.
37. Liu, Y., Abdel Samad, O., Zhang, L., Duan, B., Tong, Q., Lopes, C., Ji, R. R., Lowell, B. B., and Ma, Q. (2010). VGLUT2-dependent glutamate release from nociceptors is required to sense pain and suppress itch. Neuron 68, 543-556.

38. Liu, X. Y., Mao, L. M., Zhang, G. C., Papasian, C. J., Fibuch, E. E., Lan, H. X., Zhou, H. F., Xu, M., and Wang, J. Q. (2009). Activity-dependent modulation of limbic dopamine D3 receptors by CaMKII. Neuron 61, 425-438.
39. Loh, H. H., Liu, H. C., Cavalli, A., Yang, W., Chen, Y. F., and Wei, L. N. (1998). mu Opioid receptor knockout in mice: effects on ligand-induced analgesia and morphine lethality. Brain Res Mol Brain Res 54, 321-326.
40. Lopez, A., and Salome, L. (2009). Membrane functional organisation and dynamic of mu-opioid receptors. Cell Mol Life Sci 66, 2093-2108.
41. Luo, J., Wang, Y., Yasuda, R. P., Dunah, A. W., and Wolfe, B. B. (1997). The majority of N-methyl-D-aspartate receptor complexes in adult rat cerebral cortex contain at least three different subunits (NR1/NR2A/NR2B). Mol Pharmacol 51, 79-86.
42. Luo, M. C., Zhang, D. Q., Ma, S. W., Huang, Y. Y., Shuster, S. J., Porreca, F., and Lai, J. (2005). An efficient intrathecal delivery of small interfering RNA to the spinal cord and peripheral neurons. Mol Pain 1, 29.
43. Manara, L., Bianchi, G., Ferretti, P., and Tavani, A. (1986). Inhibition of gastrointestinal transit by morphine in rats results primarily from direct drug action on gut opioid sites. J Pharmacol Exp Ther 237, 945-949.
44. Mao, L., Yang, L., Tang, Q., Samdani, S., Zhang, G., and Wang, J. Q. (2005). The scaffold protein Homer1b/c links metabotropic glutamate receptor 5 to extracellular signal-regulated protein kinase cascades in neurons. J Neurosci 25, 2741-2752.
45. Matthes, H. W., Maldonado, R., Simonin, F., Valverde, O., Slowe, S., Kitchen, I., Befort, K., Dierich, A., Le Meur, M., Dolle, P., et al. (1996). Loss of morphine-induced analgesia, reward effect and withdrawal symptoms in mice lacking the mu-opioid-receptor gene. Nature 383, 819-823.
46. McMahon, S. B., and Koltzenburg, M. (1992). Itching for an explanation. Trends Neurosci 15, 497-501.
47. Metze, D., Reimann, S., Beissert, S., and Luger, T. (1999). Efficacy and safety of naltrexone, an oral opiate receptor antagonist, in the treatment of pruritus in internal and dermatological diseases. J Am Acad Dermatol 41, 533-539.
48. Milligan, G. (2009). G protein-coupled receptor heterodimerization: contribution to pharmacology and function. Br J Pharmacol 158, 5-14.
49. Nichols, M. L., Allen, B. J., Rogers, S. D., Ghilardi, J. R., Honore, P., Luger, N. M., Finke, M. P., Li, J., Lappi, D. A., Simone, D. A., et al. (1999). Transmission of chronic nociception by spinal neurons expressing the substance P receptor. Science 286, 1558-1561.
50. Pan, Y. X. (2005). Diversity and complexity of the mu opioid receptor gene: alternative pre-mRNA splicing and promoters. DNA Cell Biol 24, 736-750.
51. Pasternak, G. W. (2004). Multiple opiate receptors: deja vu all over again. Neuropharmacology 47 Suppl 1, 312-323.
52. Pasternak, G. W. (2010). Molecular insights into mu opioid pharmacology: From the clinic to the bench. Clin J Pain 26 Suppl 10, S3-9.
53. Patel, K. N., and Dong, X. (2010). An itch to be scratched. Neuron 68, 334-339.
54. Paus, R., Schmelz, M., Biro, T., and Steinhoff, M. (2006). Frontiers in pruritus research: scratching the brain for more effective itch therapy. J Clin Invest 116, 1174-1186.
55. Pfeiffer, M., Koch, T., Schroder, H., Laugsch, M., Hollt, V., and Schulz, S. (2002). Heterodimerization of somatostatin and opioid receptors cross-modulates phosphorylation, internalization, and desensitization. J Biol Chem 277, 19762-19772.
56. Ravindranathan, A., Joslyn, G., Robertson, M., Schuckit, M. A., Whistler, J. L., and White, R. L. (2009). Functional characterization of human variants of the mu-opioid receptor gene. Proc Natl Acad Sci USA 106, 10811-10816.
57. Ross, S. E., Mardinly, A. R., McCord, A. E., Zurawski, J., Cohen, S., Jung, C., Hu, L., Mok, S. I., Shah, A., Savner, E. M., et al. (2010). Loss of Inhibitory Interneurons in the Dorsal Spinal Cord and Elevated Itch in Bhlhb5 Mutant Mice. Neuron 65, 886-898.
58. Samways, D. S., and Henderson, G. (2006). Opioid elevation of intracellular free calcium: possible mechanisms and physiological relevance. Cell Signal 18, 151-161.
59. Schwarze, S. R., Ho, A., Vocero-Akbani, A., and Dowdy, S. F. (1999). In vivo protein transduction: delivery of a biologically active protein into the mouse. Science 285, 1569-1572.
60. Sora, I., Takahashi, N., Funada, M., Ujike, H., Revay, R. S., Donovan, D. M., Miner, L. L., and Uhl, G. R. (1997). Opiate receptor knockout mice define mu receptor roles in endogenous nociceptive responses and morphine-induced analgesia. Proc Natl Acad Sci USA 94, 1544-1549.
61. Sun, Y. G., and Chen, Z. F. (2007). A gastrin-releasing peptide receptor mediates the itch sensation in the spinal cord. Nature 448, 700-703.
62. Sun, Y. G., Zhao, Z. Q., Meng, X. L., Yin, J., Liu, X. Y., and Chen, Z. F. (2009). Cellular basis of itch sensation. Science 325, 1531-1534.
63. Szarvas, S., Harmon, D., and Murphy, D. (2003). Neuraxial opioid-induced pruritus: a review. J Clin Anesth 15, 234-239.
64. Tan, P. H., Yang, L. C., and Ji, R. R. (2009). Therapeutic potential of RNA interference in pain medicine. Open Pain J 2, 57-63.
65. Trafton, J. A., Abbadie, C., Marek, K., and Basbaum, A. I. (2000). Postsynaptic signaling via the [mu]-opioid receptor: responses of dorsal horn neurons to exogenous opioids and noxious stimulation. J Neurosci 20, 8578-8584.
67. van Baarlen, P., Troost, F. J., van Hemert, S., van der Meer, C., de Vos, W. M., de Groot, P. J., Hooiveld, G. J., Brummer, R. J., and Kleerebezem, M. (2009). Differential NF-kappaB pathways induction by Lactobacillus plantarum in the duodenum of healthy humans correlating with immune tolerance. Proc Natl Acad Sci USA 106, 2371-2376.
68. Waldhoer, M., Fong, J., Jones, R. M., Lunzer, M. M., Sharma, S. K., Kostenis, E., Portoghese, P. S., and Whistler, J. L. (2005). A heterodimer-selective agonist shows in vivo relevance of G protein-coupled receptor dimers. Proc Natl Acad Sci USA 102, 9050-9055.
69. Whistler, J. L., Chuang, H. H., Chu, P., Jan, L. Y., and von Zastrow, M. (1999). Functional dissociation of mu opioid receptor signaling and endocytosis: implications for the biology of opiate tolerance and addiction. Neuron 23, 737-746.
70. Xie, W., Samoriski, G. M., McLaughlin, J. P., Romoser, V. A., Smrcka, A., Hinkle, P. M., Bidlack, J. M., Gross, R. A., Jiang, H., and Wu, D. (1999). Genetic alteration of phospholipase C beta3 expression modulates behavioral and cellular responses to mu opioids. Proc Natl Acad Sci USA 96, 10385-10390.
71. Zhao, Z. Q., Gao, Y. J., Sun, Y. G., Zhao, C. S., Gereau, R. W. t., and Chen, Z. F. (2007). Central serotonergic neurons are differentially required for opioid analgesia but not for morphine tolerance or morphine reward. Proc Natl Acad Sci USA 104, 14519-14524.

What is claimed is:

1. A method for inhibiting opioid-induced internalization of gastrin-releasing peptide receptor (GRPR) in a neuron expressing GRPR in a subject, the method comprising administering to the subject a composition comprising a cell-penetrating peptide fused to the C-terminus of an agent that inhibits the interaction of GRPR with μ opioid receptor 1D (MOR1D), wherein the agent consisting of at least 5 and up to 22 contiguous amino acids of SEQ ID NO: 245 (EHP-STANTVDRTNHQRNEEPSS) wherein the at least 5 contiguous amino acids are selected from the group consisting of SEQ ID NO: 22 (RNEEP), SEQ ID NO: 25 (NEEPS) and SEQ ID NO: 28 (EEPSS), such that the agent inhibits opioid-induced internalization of GRPR by inhibiting the interaction of GRPR with MOR1D, and wherein the cell-penetrating peptide is selected from the group consisting of SEQ ID NO: 549, SEQ ID NO: 550, SEQ ID NO: 551, SEQ ID NO: 552, SEQ ID NO: 553, SEQ ID NO: 554, SEQ ID NO: 555, SEQ ID NO: 556, SEQ ID NO: 557, SEQ ID NO: 558, SEQ ID NO: 559, SEQ ID NO: 560, SEQ ID NO: 561, SEQ ID NO: 562, SEQ ID NO: 563, SEQ ID NO: 564, SEQ ID NO: 565, SEQ ID NO: 566 and SEQ ID NO: 567.

2. A method for inhibiting opioid-induced internalization of gastrin-releasing peptide receptor (GRPR) in a neuron expressing GRPR in a subject, the method comprising administering to the subject a composition comprising a cell-penetrating peptide fused to the C-terminus of an agent that inhibits the interaction of GRPR with μ opioid receptor 1D (MOR1D), wherein the agent is RNEEPSS (SEQ ID NO: 82), such that the agent inhibits opioid-induced internalization of GRPR by inhibiting the interaction of GRPR with MOR1D, and wherein the cell-penetrating peptide is selected from the group consisting of SEQ ID NO: 549, SEQ ID NO: 550, SEQ ID NO: 551, SEQ ID NO: 552, SEQ ID NO: 553, SEQ ID NO: 554, SEQ ID NO: 555, SEQ ID NO: 556, SEQ ID NO: 557, SEQ ID NO: 558, SEQ ID NO: 559, SEQ ID NO: 560, SEQ ID NO: 561, SEQ ID NO: 562, SEQ ID NO: 563, SEQ ID NO: 564, SEQ ID NO: 565, SEQ ID NO: 566 and SEQ ID NO: 567.

3. The method of claim 1, wherein the cell-penetrating peptide is SEQ ID NO: 550.

4. The method of claim 1, wherein the composition further comprises at least one analgesic agent.

* * * * *

UNITED STATES PATENT AND TRADEMARK OFFICE
CERTIFICATE OF CORRECTION

| | | |
|---|---|---|
| PATENT NO. | : 8,957,024 B2 | Page 1 of 1 |
| APPLICATION NO. | : 13/560620 | |
| DATED | : February 17, 2015 | |
| INVENTOR(S) | : Zhou-Feng Chen et al. | |

It is certified that error appears in the above-identified patent and that said Letters Patent is hereby corrected as shown below:

In the Specification

Column 1, Lines 14-15 delete:
"RO1 AR056318 awarded by The National Institute of Arthritis and Musculoskeletal and Skin Diseases"
And replace with:
-- AR056318 awarded by the National Institutes of Health --.

Signed and Sealed this
Fifth Day of May, 2020

Andrei Iancu
*Director of the United States Patent and Trademark Office*

SEQUENCE LISTING

<160> NUMBER OF SEQ ID NOS: 591

<210> SEQ ID NO 1
<211> LENGTH: 5
<212> TYPE: PRT
<213> ORGANISM: Mus musculus

<400> SEQUENCE: 1

Glu His Pro Ser Thr
1               5

<210> SEQ ID NO 2
<211> LENGTH: 5
<212> TYPE: PRT
<213> ORGANISM: Mus musculus

<400> SEQUENCE: 2

Ala Asn Thr Val Asp
1               5

<210> SEQ ID NO 3
<211> LENGTH: 5
<212> TYPE: PRT
<213> ORGANISM: Mus musculus

<400> SEQUENCE: 3

Arg Thr Asn His Gln
1               5

<210> SEQ ID NO 4
<211> LENGTH: 5
<212> TYPE: PRT
<213> ORGANISM: Mus musculus

<400> SEQUENCE: 4

Arg Asn Glu Glu Pro
1               5

<210> SEQ ID NO 5
<211> LENGTH: 5
<212> TYPE: PRT
<213> ORGANISM: Mus musculus

<400> SEQUENCE: 5

His Pro Ser Thr Ala
1               5

<210> SEQ ID NO 6
<211> LENGTH: 5
<212> TYPE: PRT
<213> ORGANISM: Mus musculus

<400> SEQUENCE: 6

Asn Thr Val Asp Arg
1               5

<210> SEQ ID NO 7
<211> LENGTH: 5
<212> TYPE: PRT
<213> ORGANISM: Mus musculus

<400> SEQUENCE: 7

Thr Asn His Gln Arg
1               5

```
<210> SEQ ID NO 8
<211> LENGTH: 5
<212> TYPE: PRT
<213> ORGANISM: Mus musculus

<400> SEQUENCE: 8

Asn Glu Glu Pro Ser
1               5

<210> SEQ ID NO 9
<211> LENGTH: 5
<212> TYPE: PRT
<213> ORGANISM: Mus musculus

<400> SEQUENCE: 9

Pro Ser Thr Ala Asn
1               5

<210> SEQ ID NO 10
<211> LENGTH: 5
<212> TYPE: PRT
<213> ORGANISM: Mus musculus

<400> SEQUENCE: 10

Thr Val Asp Arg Thr
1               5

<210> SEQ ID NO 11
<211> LENGTH: 5
<212> TYPE: PRT
<213> ORGANISM: Mus musculus

<400> SEQUENCE: 11

Asn His Gln Arg Asn
1               5

<210> SEQ ID NO 12
<211> LENGTH: 5
<212> TYPE: PRT
<213> ORGANISM: Mus musculus

<400> SEQUENCE: 12

Glu Glu Pro Ser Ser
1               5

<210> SEQ ID NO 13
<211> LENGTH: 5
<212> TYPE: PRT
<213> ORGANISM: Mus musculus

<400> SEQUENCE: 13

Ser Thr Ala Asn Thr
1               5

<210> SEQ ID NO 14
<211> LENGTH: 5
<212> TYPE: PRT
<213> ORGANISM: Mus musculus

<400> SEQUENCE: 14

Val Asp Arg Thr Asn
1               5

<210> SEQ ID NO 15
```

```
<211> LENGTH: 5
<212> TYPE: PRT
<213> ORGANISM: Mus musculus

<400> SEQUENCE: 15

His Gln Arg Asn Glu
1               5

<210> SEQ ID NO 16
<211> LENGTH: 5
<212> TYPE: PRT
<213> ORGANISM: Mus musculus

<400> SEQUENCE: 16

Gln Arg Asn Glu Glu
1               5

<210> SEQ ID NO 17
<211> LENGTH: 5
<212> TYPE: PRT
<213> ORGANISM: Mus musculus

<400> SEQUENCE: 17

Thr Ala Asn Thr Val
1               5

<210> SEQ ID NO 18
<211> LENGTH: 5
<212> TYPE: PRT
<213> ORGANISM: Mus musculus

<400> SEQUENCE: 18

Asp Arg Thr Asn His
1               5

<210> SEQ ID NO 19
<211> LENGTH: 5
<212> TYPE: PRT
<213> ORGANISM: Mus musculus

<400> SEQUENCE: 19

Gln Arg Asn Glu Glu
1               5

<210> SEQ ID NO 20
<211> LENGTH: 5
<212> TYPE: PRT
<213> ORGANISM: Mus musculus

<400> SEQUENCE: 20

Ala Asn Thr Val Asp
1               5

<210> SEQ ID NO 21
<211> LENGTH: 5
<212> TYPE: PRT
<213> ORGANISM: Mus musculus

<400> SEQUENCE: 21

Arg Thr Asn His Gln
1               5

<210> SEQ ID NO 22
<211> LENGTH: 5
<212> TYPE: PRT
```

```
<213> ORGANISM: Mus musculus

<400> SEQUENCE: 22

Arg Asn Glu Glu Pro
1               5

<210> SEQ ID NO 23
<211> LENGTH: 5
<212> TYPE: PRT
<213> ORGANISM: Mus musculus

<400> SEQUENCE: 23

Asn Thr Val Asp Arg
1               5

<210> SEQ ID NO 24
<211> LENGTH: 5
<212> TYPE: PRT
<213> ORGANISM: Mus musculus

<400> SEQUENCE: 24

Thr Asn His Gln Arg
1               5

<210> SEQ ID NO 25
<211> LENGTH: 5
<212> TYPE: PRT
<213> ORGANISM: Mus musculus

<400> SEQUENCE: 25

Asn Glu Glu Pro Ser
1               5

<210> SEQ ID NO 26
<211> LENGTH: 5
<212> TYPE: PRT
<213> ORGANISM: Mus musculus

<400> SEQUENCE: 26

Thr Val Asp Arg Thr
1               5

<210> SEQ ID NO 27
<211> LENGTH: 5
<212> TYPE: PRT
<213> ORGANISM: Mus musculus

<400> SEQUENCE: 27

Asn His Gln Arg Asn
1               5

<210> SEQ ID NO 28
<211> LENGTH: 5
<212> TYPE: PRT
<213> ORGANISM: Mus musculus

<400> SEQUENCE: 28

Glu Glu Pro Ser Ser
1               5

<210> SEQ ID NO 29
<211> LENGTH: 5
<212> TYPE: PRT
<213> ORGANISM: Mus musculus
```

```
<400> SEQUENCE: 29

Val Asp Arg Thr Asn
1               5

<210> SEQ ID NO 30
<211> LENGTH: 5
<212> TYPE: PRT
<213> ORGANISM: Mus musculus

<400> SEQUENCE: 30

His Gln Arg Asn Glu
1               5

<210> SEQ ID NO 31
<211> LENGTH: 5
<212> TYPE: PRT
<213> ORGANISM: Mus musculus

<400> SEQUENCE: 31

Asp Arg Thr Asn His
1               5

<210> SEQ ID NO 32
<211> LENGTH: 5
<212> TYPE: PRT
<213> ORGANISM: Mus musculus

<400> SEQUENCE: 32

Gln Arg Asn Glu Glu
1               5

<210> SEQ ID NO 33
<211> LENGTH: 5
<212> TYPE: PRT
<213> ORGANISM: Mus musculus

<400> SEQUENCE: 33

Arg Thr Asn His Gln
1               5

<210> SEQ ID NO 34
<211> LENGTH: 5
<212> TYPE: PRT
<213> ORGANISM: Mus musculus

<400> SEQUENCE: 34

Arg Asn Glu Glu Pro
1               5

<210> SEQ ID NO 35
<211> LENGTH: 5
<212> TYPE: PRT
<213> ORGANISM: Mus musculus

<400> SEQUENCE: 35

Thr Asn His Gln Arg
1               5

<210> SEQ ID NO 36
<211> LENGTH: 5
<212> TYPE: PRT
<213> ORGANISM: Mus musculus

<400> SEQUENCE: 36
```

Asn Glu Glu Pro Ser
1               5

<210> SEQ ID NO 37
<211> LENGTH: 5
<212> TYPE: PRT
<213> ORGANISM: Mus musculus

<400> SEQUENCE: 37

Asn His Gln Arg Asn
1               5

<210> SEQ ID NO 38
<211> LENGTH: 5
<212> TYPE: PRT
<213> ORGANISM: Mus musculus

<400> SEQUENCE: 38

Glu Glu Pro Ser Ser
1               5

<210> SEQ ID NO 39
<211> LENGTH: 5
<212> TYPE: PRT
<213> ORGANISM: Mus musculus

<400> SEQUENCE: 39

His Gln Arg Asn Glu
1               5

<210> SEQ ID NO 40
<211> LENGTH: 5
<212> TYPE: PRT
<213> ORGANISM: Mus musculus

<400> SEQUENCE: 40

Gln Arg Asn Glu Glu
1               5

<210> SEQ ID NO 41
<211> LENGTH: 5
<212> TYPE: PRT
<213> ORGANISM: Mus musculus

<400> SEQUENCE: 41

Arg Asn Glu Glu Pro
1               5

<210> SEQ ID NO 42
<211> LENGTH: 5
<212> TYPE: PRT
<213> ORGANISM: Mus musculus

<400> SEQUENCE: 42

Asn Glu Glu Pro Ser
1               5

<210> SEQ ID NO 43
<211> LENGTH: 5
<212> TYPE: PRT
<213> ORGANISM: Mus musculus

<400> SEQUENCE: 43

Glu Glu Pro Ser Ser
1               5

<210> SEQ ID NO 44
<211> LENGTH: 6
<212> TYPE: PRT
<213> ORGANISM: Mus musculus

<400> SEQUENCE: 44

Glu His Pro Ser Thr Ala
1               5

<210> SEQ ID NO 45
<211> LENGTH: 6
<212> TYPE: PRT
<213> ORGANISM: Mus musculus

<400> SEQUENCE: 45

Asn Thr Val Asp Arg Thr
1               5

<210> SEQ ID NO 46
<211> LENGTH: 6
<212> TYPE: PRT
<213> ORGANISM: Mus musculus

<400> SEQUENCE: 46

Asn His Gln Arg Asn Glu
1               5

<210> SEQ ID NO 47
<211> LENGTH: 6
<212> TYPE: PRT
<213> ORGANISM: Mus musculus

<400> SEQUENCE: 47

His Pro Ser Thr Ala Asn
1               5

<210> SEQ ID NO 48
<211> LENGTH: 6
<212> TYPE: PRT
<213> ORGANISM: Mus musculus

<400> SEQUENCE: 48

Thr Val Asp Arg Thr Asn
1               5

<210> SEQ ID NO 49
<211> LENGTH: 6
<212> TYPE: PRT
<213> ORGANISM: Mus musculus

<400> SEQUENCE: 49

His Gln Arg Asn Glu Glu
1               5

<210> SEQ ID NO 50
<211> LENGTH: 6
<212> TYPE: PRT
<213> ORGANISM: Mus musculus

<400> SEQUENCE: 50

Pro Ser Thr Ala Asn Thr
1               5

```
<210> SEQ ID NO 51
<211> LENGTH: 6
<212> TYPE: PRT
<213> ORGANISM: Mus musculus

<400> SEQUENCE: 51

Val Asp Arg Thr Asn His
1               5

<210> SEQ ID NO 52
<211> LENGTH: 6
<212> TYPE: PRT
<213> ORGANISM: Mus musculus

<400> SEQUENCE: 52

Gln Arg Asn Glu Glu Pro
1               5

<210> SEQ ID NO 53
<211> LENGTH: 6
<212> TYPE: PRT
<213> ORGANISM: Mus musculus

<400> SEQUENCE: 53

Ser Thr Ala Asn Thr Val
1               5

<210> SEQ ID NO 54
<211> LENGTH: 6
<212> TYPE: PRT
<213> ORGANISM: Mus musculus

<400> SEQUENCE: 54

Asp Arg Thr Asn His Gln
1               5

<210> SEQ ID NO 55
<211> LENGTH: 6
<212> TYPE: PRT
<213> ORGANISM: Mus musculus

<400> SEQUENCE: 55

Arg Asn Glu Glu Pro Ser
1               5

<210> SEQ ID NO 56
<211> LENGTH: 6
<212> TYPE: PRT
<213> ORGANISM: Mus musculus

<400> SEQUENCE: 56

Thr Ala Asn Thr Val Asp
1               5

<210> SEQ ID NO 57
<211> LENGTH: 6
<212> TYPE: PRT
<213> ORGANISM: Mus musculus

<400> SEQUENCE: 57

Arg Thr Asn His Gln Arg
1               5

<210> SEQ ID NO 58
<211> LENGTH: 6
```

```
<212> TYPE: PRT
<213> ORGANISM: Mus musculus

<400> SEQUENCE: 58

Asn Glu Glu Pro Ser Ser
1               5

<210> SEQ ID NO 59
<211> LENGTH: 6
<212> TYPE: PRT
<213> ORGANISM: Mus musculus

<400> SEQUENCE: 59

Ala Asn Thr Val Asp Arg
1               5

<210> SEQ ID NO 60
<211> LENGTH: 6
<212> TYPE: PRT
<213> ORGANISM: Mus musculus

<400> SEQUENCE: 60

Thr Asn His Gln Arg Asn
1               5

<210> SEQ ID NO 61
<211> LENGTH: 6
<212> TYPE: PRT
<213> ORGANISM: Mus musculus

<400> SEQUENCE: 61

Asn Thr Val Asp Arg Thr
1               5

<210> SEQ ID NO 62
<211> LENGTH: 6
<212> TYPE: PRT
<213> ORGANISM: Mus musculus

<400> SEQUENCE: 62

Asn His Gln Arg Asn Glu
1               5

<210> SEQ ID NO 63
<211> LENGTH: 6
<212> TYPE: PRT
<213> ORGANISM: Mus musculus

<400> SEQUENCE: 63

Thr Val Asp Arg Thr Asn
1               5

<210> SEQ ID NO 64
<211> LENGTH: 6
<212> TYPE: PRT
<213> ORGANISM: Mus musculus

<400> SEQUENCE: 64

His Gln Arg Asn Glu Glu
1               5

<210> SEQ ID NO 65
<211> LENGTH: 6
<212> TYPE: PRT
<213> ORGANISM: Mus musculus
```

```
<400> SEQUENCE: 65

Val Asp Arg Thr Asn His
1               5

<210> SEQ ID NO 66
<211> LENGTH: 6
<212> TYPE: PRT
<213> ORGANISM: Mus musculus

<400> SEQUENCE: 66

Gln Arg Asn Glu Glu Pro
1               5

<210> SEQ ID NO 67
<211> LENGTH: 6
<212> TYPE: PRT
<213> ORGANISM: Mus musculus

<400> SEQUENCE: 67

Asp Arg Thr Asn His Gln
1               5

<210> SEQ ID NO 68
<211> LENGTH: 6
<212> TYPE: PRT
<213> ORGANISM: Mus musculus

<400> SEQUENCE: 68

Arg Asn Glu Glu Pro Ser
1               5

<210> SEQ ID NO 69
<211> LENGTH: 6
<212> TYPE: PRT
<213> ORGANISM: Mus musculus

<400> SEQUENCE: 69

Arg Thr Asn His Gln Arg
1               5

<210> SEQ ID NO 70
<211> LENGTH: 6
<212> TYPE: PRT
<213> ORGANISM: Mus musculus

<400> SEQUENCE: 70

Asn Glu Glu Pro Ser Ser
1               5

<210> SEQ ID NO 71
<211> LENGTH: 6
<212> TYPE: PRT
<213> ORGANISM: Mus musculus

<400> SEQUENCE: 71

Thr Asn His Gln Arg Asn
1               5

<210> SEQ ID NO 72
<211> LENGTH: 6
<212> TYPE: PRT
<213> ORGANISM: Mus musculus

<400> SEQUENCE: 72
```

Asn His Gln Arg Asn Glu
1               5

<210> SEQ ID NO 73
<211> LENGTH: 6
<212> TYPE: PRT
<213> ORGANISM: Mus musculus

<400> SEQUENCE: 73

His Gln Arg Asn Glu Glu
1               5

<210> SEQ ID NO 74
<211> LENGTH: 6
<212> TYPE: PRT
<213> ORGANISM: Mus musculus

<400> SEQUENCE: 74

Gln Arg Asn Glu Glu Pro
1               5

<210> SEQ ID NO 75
<211> LENGTH: 6
<212> TYPE: PRT
<213> ORGANISM: Mus musculus

<400> SEQUENCE: 75

Arg Asn Glu Glu Pro Ser
1               5

<210> SEQ ID NO 76
<211> LENGTH: 6
<212> TYPE: PRT
<213> ORGANISM: Mus musculus

<400> SEQUENCE: 76

Asn Glu Glu Pro Ser Ser
1               5

<210> SEQ ID NO 77
<211> LENGTH: 7
<212> TYPE: PRT
<213> ORGANISM: Mus musculus

<400> SEQUENCE: 77

Glu His Pro Ser Thr Ala Asn
1               5

<210> SEQ ID NO 78
<211> LENGTH: 7
<212> TYPE: PRT
<213> ORGANISM: Mus musculus

<400> SEQUENCE: 78

Thr Val Asp Arg Thr Asn His
1               5

<210> SEQ ID NO 79
<211> LENGTH: 7
<212> TYPE: PRT
<213> ORGANISM: Mus musculus

<400> SEQUENCE: 79

Gln Arg Asn Glu Glu Pro Ser

```
<210> SEQ ID NO 80
<211> LENGTH: 7
<212> TYPE: PRT
<213> ORGANISM: Mus musculus

<400> SEQUENCE: 80

His Pro Ser Thr Ala Asn Thr
1               5

<210> SEQ ID NO 81
<211> LENGTH: 7
<212> TYPE: PRT
<213> ORGANISM: Mus musculus

<400> SEQUENCE: 81

Val Asp Arg Thr Asn His Gln
1               5

<210> SEQ ID NO 82
<211> LENGTH: 7
<212> TYPE: PRT
<213> ORGANISM: Mus musculus

<400> SEQUENCE: 82

Arg Asn Glu Glu Pro Ser Ser
1               5

<210> SEQ ID NO 83
<211> LENGTH: 7
<212> TYPE: PRT
<213> ORGANISM: Mus musculus

<400> SEQUENCE: 83

Pro Ser Thr Ala Asn Thr Val
1               5

<210> SEQ ID NO 84
<211> LENGTH: 7
<212> TYPE: PRT
<213> ORGANISM: Mus musculus

<400> SEQUENCE: 84

Asp Arg Thr Asn His Gln Arg
1               5

<210> SEQ ID NO 85
<211> LENGTH: 7
<212> TYPE: PRT
<213> ORGANISM: Mus musculus

<400> SEQUENCE: 85

Ser Thr Ala Asn Thr Val Asp
1               5

<210> SEQ ID NO 86
<211> LENGTH: 7
<212> TYPE: PRT
<213> ORGANISM: Mus musculus

<400> SEQUENCE: 86

Arg Thr Asn His Gln Arg Asn
1               5
```

```
<210> SEQ ID NO 87
<211> LENGTH: 7
<212> TYPE: PRT
<213> ORGANISM: Mus musculus

<400> SEQUENCE: 87

Thr Ala Asn Thr Val Asp Arg
1               5

<210> SEQ ID NO 88
<211> LENGTH: 7
<212> TYPE: PRT
<213> ORGANISM: Mus musculus

<400> SEQUENCE: 88

Thr Asn His Gln Arg Asn Glu
1               5

<210> SEQ ID NO 89
<211> LENGTH: 7
<212> TYPE: PRT
<213> ORGANISM: Mus musculus

<400> SEQUENCE: 89

Ala Asn Thr Val Asp Arg Thr
1               5

<210> SEQ ID NO 90
<211> LENGTH: 7
<212> TYPE: PRT
<213> ORGANISM: Mus musculus

<400> SEQUENCE: 90

Asn His Gln Arg Asn Glu Glu
1               5

<210> SEQ ID NO 91
<211> LENGTH: 7
<212> TYPE: PRT
<213> ORGANISM: Mus musculus

<400> SEQUENCE: 91

Asn Thr Val Asp Arg Thr Asn
1               5

<210> SEQ ID NO 92
<211> LENGTH: 7
<212> TYPE: PRT
<213> ORGANISM: Mus musculus

<400> SEQUENCE: 92

His Gln Arg Asn Glu Glu Pro
1               5

<210> SEQ ID NO 93
<211> LENGTH: 7
<212> TYPE: PRT
<213> ORGANISM: Mus musculus

<400> SEQUENCE: 93

Thr Val Asp Arg Thr Asn His
1               5

<210> SEQ ID NO 94
```

```
<211> LENGTH: 7
<212> TYPE: PRT
<213> ORGANISM: Mus musculus

<400> SEQUENCE: 94

Gln Arg Asn Glu Glu Pro Ser
1               5

<210> SEQ ID NO 95
<211> LENGTH: 7
<212> TYPE: PRT
<213> ORGANISM: Mus musculus

<400> SEQUENCE: 95

Val Asp Arg Thr Asn His Gln
1               5

<210> SEQ ID NO 96
<211> LENGTH: 7
<212> TYPE: PRT
<213> ORGANISM: Mus musculus

<400> SEQUENCE: 96

Arg Asn Glu Glu Pro Ser Ser
1               5

<210> SEQ ID NO 97
<211> LENGTH: 7
<212> TYPE: PRT
<213> ORGANISM: Mus musculus

<400> SEQUENCE: 97

Asp Arg Thr Asn His Gln Arg
1               5

<210> SEQ ID NO 98
<211> LENGTH: 7
<212> TYPE: PRT
<213> ORGANISM: Mus musculus

<400> SEQUENCE: 98

Arg Thr Asn His Gln Arg Asn
1               5

<210> SEQ ID NO 99
<211> LENGTH: 7
<212> TYPE: PRT
<213> ORGANISM: Mus musculus

<400> SEQUENCE: 99

Thr Asn His Gln Arg Asn Glu
1               5

<210> SEQ ID NO 100
<211> LENGTH: 7
<212> TYPE: PRT
<213> ORGANISM: Mus musculus

<400> SEQUENCE: 100

Asn His Gln Arg Asn Glu Glu
1               5

<210> SEQ ID NO 101
<211> LENGTH: 7
<212> TYPE: PRT
```

<213> ORGANISM: Mus musculus

<400> SEQUENCE: 101

His Gln Arg Asn Glu Glu Pro
1               5

<210> SEQ ID NO 102
<211> LENGTH: 7
<212> TYPE: PRT
<213> ORGANISM: Mus musculus

<400> SEQUENCE: 102

Gln Arg Asn Glu Glu Pro Ser
1               5

<210> SEQ ID NO 103
<211> LENGTH: 7
<212> TYPE: PRT
<213> ORGANISM: Mus musculus

<400> SEQUENCE: 103

Arg Asn Glu Glu Pro Ser Ser
1               5

<210> SEQ ID NO 104
<211> LENGTH: 8
<212> TYPE: PRT
<213> ORGANISM: Mus musculus

<400> SEQUENCE: 104

Glu His Pro Ser Thr Ala Asn Thr
1               5

<210> SEQ ID NO 105
<211> LENGTH: 8
<212> TYPE: PRT
<213> ORGANISM: Mus musculus

<400> SEQUENCE: 105

Val Asp Arg Thr Asn His Gln Arg
1               5

<210> SEQ ID NO 106
<211> LENGTH: 8
<212> TYPE: PRT
<213> ORGANISM: Mus musculus

<400> SEQUENCE: 106

His Pro Ser Thr Ala Asn Thr Val
1               5

<210> SEQ ID NO 107
<211> LENGTH: 8
<212> TYPE: PRT
<213> ORGANISM: Mus musculus

<400> SEQUENCE: 107

Asp Arg Thr Asn His Gln Arg Asn
1               5

<210> SEQ ID NO 108
<211> LENGTH: 8
<212> TYPE: PRT
<213> ORGANISM: Mus musculus

<400> SEQUENCE: 108

Pro Ser Thr Ala Asn Thr Val Asp
1               5

<210> SEQ ID NO 109
<211> LENGTH: 8
<212> TYPE: PRT
<213> ORGANISM: Mus musculus

<400> SEQUENCE: 109

Thr Asn His Gln Arg Asn Glu Glu
1               5

<210> SEQ ID NO 110
<211> LENGTH: 8
<212> TYPE: PRT
<213> ORGANISM: Mus musculus

<400> SEQUENCE: 110

Ser Thr Ala Asn Thr Val Asp Arg
1               5

<210> SEQ ID NO 111
<211> LENGTH: 8
<212> TYPE: PRT
<213> ORGANISM: Mus musculus

<400> SEQUENCE: 111

Thr Asn His Gln Arg Asn Glu Glu
1               5

<210> SEQ ID NO 112
<211> LENGTH: 8
<212> TYPE: PRT
<213> ORGANISM: Mus musculus

<400> SEQUENCE: 112

Thr Ala Asn Thr Val Asp Arg Thr
1               5

<210> SEQ ID NO 113
<211> LENGTH: 8
<212> TYPE: PRT
<213> ORGANISM: Mus musculus

<400> SEQUENCE: 113

Asn His Gln Arg Asn Glu Glu Pro
1               5

<210> SEQ ID NO 114
<211> LENGTH: 8
<212> TYPE: PRT
<213> ORGANISM: Mus musculus

<400> SEQUENCE: 114

Ala Asn Thr Val Asp Arg Thr Asn
1               5

<210> SEQ ID NO 115
<211> LENGTH: 8
<212> TYPE: PRT
<213> ORGANISM: Mus musculus

<400> SEQUENCE: 115

His Gln Arg Asn Glu Glu Pro Ser
1               5

<210> SEQ ID NO 116
<211> LENGTH: 8
<212> TYPE: PRT
<213> ORGANISM: Mus musculus

<400> SEQUENCE: 116

Asn Thr Val Asp Arg Thr Asn His
1               5

<210> SEQ ID NO 117
<211> LENGTH: 8
<212> TYPE: PRT
<213> ORGANISM: Mus musculus

<400> SEQUENCE: 117

Gln Arg Asn Glu Glu Pro Ser Ser
1               5

<210> SEQ ID NO 118
<211> LENGTH: 8
<212> TYPE: PRT
<213> ORGANISM: Mus musculus

<400> SEQUENCE: 118

Thr Val Asp Arg Thr Asn His Gln
1               5

<210> SEQ ID NO 119
<211> LENGTH: 8
<212> TYPE: PRT
<213> ORGANISM: Mus musculus

<400> SEQUENCE: 119

Val Asp Arg Thr Asn His Gln Arg
1               5

<210> SEQ ID NO 120
<211> LENGTH: 8
<212> TYPE: PRT
<213> ORGANISM: Mus musculus

<400> SEQUENCE: 120

Asp Arg Thr Asn His Gln Arg Asn
1               5

<210> SEQ ID NO 121
<211> LENGTH: 8
<212> TYPE: PRT
<213> ORGANISM: Mus musculus

<400> SEQUENCE: 121

Arg Thr Asn His Gln Arg Asn Glu
1               5

<210> SEQ ID NO 122
<211> LENGTH: 8
<212> TYPE: PRT
<213> ORGANISM: Mus musculus

<400> SEQUENCE: 122

Thr Asn His Gln Arg Asn Glu Glu
1               5

<210> SEQ ID NO 123
<211> LENGTH: 8
<212> TYPE: PRT
<213> ORGANISM: Mus musculus

<400> SEQUENCE: 123

Asn His Gln Arg Asn Glu Glu Pro
1               5

<210> SEQ ID NO 124
<211> LENGTH: 8
<212> TYPE: PRT
<213> ORGANISM: Mus musculus

<400> SEQUENCE: 124

His Gln Arg Asn Glu Glu Pro Ser
1               5

<210> SEQ ID NO 125
<211> LENGTH: 8
<212> TYPE: PRT
<213> ORGANISM: Mus musculus

<400> SEQUENCE: 125

Gln Arg Asn Glu Glu Pro Ser Ser
1               5

<210> SEQ ID NO 126
<211> LENGTH: 9
<212> TYPE: PRT
<213> ORGANISM: Mus musculus

<400> SEQUENCE: 126

Glu His Pro Ser Thr Ala Asn Thr Val
1               5

<210> SEQ ID NO 127
<211> LENGTH: 9
<212> TYPE: PRT
<213> ORGANISM: Mus musculus

<400> SEQUENCE: 127

Asp Arg Thr Asn His Gln Arg Asn Glu
1               5

<210> SEQ ID NO 128
<211> LENGTH: 9
<212> TYPE: PRT
<213> ORGANISM: Mus musculus

<400> SEQUENCE: 128

His Pro Ser Thr Ala Asn Thr Val Asp
1               5

<210> SEQ ID NO 129
<211> LENGTH: 9
<212> TYPE: PRT
<213> ORGANISM: Mus musculus

<400> SEQUENCE: 129

Arg Thr Asn His Gln Arg Asn Glu Glu
1               5

<210> SEQ ID NO 130
<211> LENGTH: 9
<212> TYPE: PRT
<213> ORGANISM: Mus musculus

<400> SEQUENCE: 130

Pro Ser Thr Ala Asn Thr Val Asp Arg
1               5

<210> SEQ ID NO 131
<211> LENGTH: 9
<212> TYPE: PRT
<213> ORGANISM: Mus musculus

<400> SEQUENCE: 131

Thr Asn His Gln Arg Asn Glu Glu Pro
1               5

<210> SEQ ID NO 132
<211> LENGTH: 9
<212> TYPE: PRT
<213> ORGANISM: Mus musculus

<400> SEQUENCE: 132

Ser Thr Ala Asn Thr Val Asp Arg Thr
1               5

<210> SEQ ID NO 133
<211> LENGTH: 9
<212> TYPE: PRT
<213> ORGANISM: Mus musculus

<400> SEQUENCE: 133

Asn His Gln Arg Asn Glu Glu Pro Ser
1               5

<210> SEQ ID NO 134
<211> LENGTH: 9
<212> TYPE: PRT
<213> ORGANISM: Mus musculus

<400> SEQUENCE: 134

Thr Ala Asn Thr Val Asp Arg Thr Asn
1               5

<210> SEQ ID NO 135
<211> LENGTH: 9
<212> TYPE: PRT
<213> ORGANISM: Mus musculus

<400> SEQUENCE: 135

His Gln Arg Asn Glu Glu Pro Ser Ser
1               5

<210> SEQ ID NO 136
<211> LENGTH: 9
<212> TYPE: PRT
<213> ORGANISM: Mus musculus

<400> SEQUENCE: 136

Ala Asn Thr Val Asp Arg Thr Asn His
1               5

<210> SEQ ID NO 137
<211> LENGTH: 9

```
<212> TYPE: PRT
<213> ORGANISM: Mus musculus

<400> SEQUENCE: 137

Asn Thr Val Asp Arg Thr Asn His Gln
1               5

<210> SEQ ID NO 138
<211> LENGTH: 9
<212> TYPE: PRT
<213> ORGANISM: Mus musculus

<400> SEQUENCE: 138

Thr Val Asp Arg Thr Asn His Gln Arg
1               5

<210> SEQ ID NO 139
<211> LENGTH: 9
<212> TYPE: PRT
<213> ORGANISM: Mus musculus

<400> SEQUENCE: 139

Val Asp Arg Thr Asn His Gln Arg Asn
1               5

<210> SEQ ID NO 140
<211> LENGTH: 9
<212> TYPE: PRT
<213> ORGANISM: Mus musculus

<400> SEQUENCE: 140

Asp Arg Thr Asn His Gln Arg Asn Glu
1               5

<210> SEQ ID NO 141
<211> LENGTH: 9
<212> TYPE: PRT
<213> ORGANISM: Mus musculus

<400> SEQUENCE: 141

Arg Thr Asn His Gln Arg Asn Glu Glu
1               5

<210> SEQ ID NO 142
<211> LENGTH: 9
<212> TYPE: PRT
<213> ORGANISM: Mus musculus

<400> SEQUENCE: 142

Thr Asn His Gln Arg Asn Glu Glu Pro
1               5

<210> SEQ ID NO 143
<211> LENGTH: 9
<212> TYPE: PRT
<213> ORGANISM: Mus musculus

<400> SEQUENCE: 143

Asn His Gln Arg Asn Glu Glu Pro Ser
1               5

<210> SEQ ID NO 144
<211> LENGTH: 9
<212> TYPE: PRT
<213> ORGANISM: Mus musculus
```

<400> SEQUENCE: 144

His Gln Arg Asn Glu Glu Pro Ser Ser
1               5

<210> SEQ ID NO 145
<211> LENGTH: 10
<212> TYPE: PRT
<213> ORGANISM: Mus musculus

<400> SEQUENCE: 145

Glu His Pro Ser Thr Ala Asn Thr Val Asp
1               5                   10

<210> SEQ ID NO 146
<211> LENGTH: 10
<212> TYPE: PRT
<213> ORGANISM: Mus musculus

<400> SEQUENCE: 146

Arg Thr Asn His Gln Arg Asn Glu Glu Pro
1               5                   10

<210> SEQ ID NO 147
<211> LENGTH: 10
<212> TYPE: PRT
<213> ORGANISM: Mus musculus

<400> SEQUENCE: 147

His Pro Ser Thr Ala Asn Thr Val Asp Arg
1               5                   10

<210> SEQ ID NO 148
<211> LENGTH: 10
<212> TYPE: PRT
<213> ORGANISM: Mus musculus

<400> SEQUENCE: 148

Thr Asn His Gln Arg Asn Glu Glu Pro Ser
1               5                   10

<210> SEQ ID NO 149
<211> LENGTH: 10
<212> TYPE: PRT
<213> ORGANISM: Mus musculus

<400> SEQUENCE: 149

Pro Ser Thr Ala Asn Thr Val Asp Arg Thr
1               5                   10

<210> SEQ ID NO 150
<211> LENGTH: 10
<212> TYPE: PRT
<213> ORGANISM: Mus musculus

<400> SEQUENCE: 150

Asn His Gln Arg Asn Glu Glu Pro Ser Ser
1               5                   10

<210> SEQ ID NO 151
<211> LENGTH: 10
<212> TYPE: PRT
<213> ORGANISM: Mus musculus

<400> SEQUENCE: 151

Ser Thr Ala Asn Thr Val Asp Arg Thr Asn
1               5                   10

<210> SEQ ID NO 152
<211> LENGTH: 10
<212> TYPE: PRT
<213> ORGANISM: Mus musculus

<400> SEQUENCE: 152

Thr Ala Asn Thr Val Asp Arg Thr Asn His
1               5                   10

<210> SEQ ID NO 153
<211> LENGTH: 10
<212> TYPE: PRT
<213> ORGANISM: Mus musculus

<400> SEQUENCE: 153

Ala Asn Thr Val Asp Arg Thr Asn His Gln
1               5                   10

<210> SEQ ID NO 154
<211> LENGTH: 10
<212> TYPE: PRT
<213> ORGANISM: Mus musculus

<400> SEQUENCE: 154

Asn Thr Val Asp Arg Thr Asn His Gln Arg
1               5                   10

<210> SEQ ID NO 155
<211> LENGTH: 10
<212> TYPE: PRT
<213> ORGANISM: Mus musculus

<400> SEQUENCE: 155

Thr Val Asp Arg Thr Asn His Gln Arg Asn
1               5                   10

<210> SEQ ID NO 156
<211> LENGTH: 10
<212> TYPE: PRT
<213> ORGANISM: Mus musculus

<400> SEQUENCE: 156

Val Asp Arg Thr Asn His Gln Arg Asn Glu
1               5                   10

<210> SEQ ID NO 157
<211> LENGTH: 10
<212> TYPE: PRT
<213> ORGANISM: Mus musculus

<400> SEQUENCE: 157

Asp Arg Thr Asn His Gln Arg Asn Glu Glu
1               5                   10

<210> SEQ ID NO 158
<211> LENGTH: 10
<212> TYPE: PRT
<213> ORGANISM: Mus musculus

<400> SEQUENCE: 158

Arg Thr Asn His Gln Arg Asn Glu Glu Pro

```
                         1               5                   10

<210> SEQ ID NO 159
<211> LENGTH: 10
<212> TYPE: PRT
<213> ORGANISM: Mus musculus

<400> SEQUENCE: 159

Thr Asn His Gln Arg Asn Glu Glu Pro Ser
1               5                   10

<210> SEQ ID NO 160
<211> LENGTH: 11
<212> TYPE: PRT
<213> ORGANISM: Mus musculus

<400> SEQUENCE: 160

Glu His Pro Ser Thr Ala Asn Thr Val Asp Arg
1               5                   10

<210> SEQ ID NO 161
<211> LENGTH: 11
<212> TYPE: PRT
<213> ORGANISM: Mus musculus

<400> SEQUENCE: 161

Thr Asn His Gln Arg Asn Glu Glu Pro Ser Ser
1               5                   10

<210> SEQ ID NO 162
<211> LENGTH: 11
<212> TYPE: PRT
<213> ORGANISM: Mus musculus

<400> SEQUENCE: 162

His Pro Ser Thr Ala Asn Thr Val Asp Arg Thr
1               5                   10

<210> SEQ ID NO 163
<211> LENGTH: 11
<212> TYPE: PRT
<213> ORGANISM: Mus musculus

<400> SEQUENCE: 163

Pro Ser Thr Ala Asn Thr Val Asp Arg Thr Asn
1               5                   10

<210> SEQ ID NO 164
<211> LENGTH: 11
<212> TYPE: PRT
<213> ORGANISM: Mus musculus

<400> SEQUENCE: 164

Ser Thr Ala Asn Thr Val Asp Arg Thr Asn His
1               5                   10

<210> SEQ ID NO 165
<211> LENGTH: 11
<212> TYPE: PRT
<213> ORGANISM: Mus musculus

<400> SEQUENCE: 165

Thr Ala Asn Thr Val Asp Arg Thr Asn His Gln
1               5                   10
```

<210> SEQ ID NO 166
<211> LENGTH: 11
<212> TYPE: PRT
<213> ORGANISM: Mus musculus

<400> SEQUENCE: 166

Ala Asn Thr Val Asp Arg Thr Asn His Gln Arg
1               5                   10

<210> SEQ ID NO 167
<211> LENGTH: 11
<212> TYPE: PRT
<213> ORGANISM: Mus musculus

<400> SEQUENCE: 167

Asn Thr Val Asp Arg Thr Asn His Gln Arg Asn
1               5                   10

<210> SEQ ID NO 168
<211> LENGTH: 11
<212> TYPE: PRT
<213> ORGANISM: Mus musculus

<400> SEQUENCE: 168

Thr Val Asp Arg Thr Asn His Gln Arg Asn Glu
1               5                   10

<210> SEQ ID NO 169
<211> LENGTH: 11
<212> TYPE: PRT
<213> ORGANISM: Mus musculus

<400> SEQUENCE: 169

Val Asp Arg Thr Asn His Gln Arg Asn Glu Glu
1               5                   10

<210> SEQ ID NO 170
<211> LENGTH: 11
<212> TYPE: PRT
<213> ORGANISM: Mus musculus

<400> SEQUENCE: 170

Asp Arg Thr Asn His Gln Arg Asn Glu Glu Pro
1               5                   10

<210> SEQ ID NO 171
<211> LENGTH: 11
<212> TYPE: PRT
<213> ORGANISM: Mus musculus

<400> SEQUENCE: 171

Arg Thr Asn His Gln Arg Asn Glu Glu Pro Ser
1               5                   10

<210> SEQ ID NO 172
<211> LENGTH: 11
<212> TYPE: PRT
<213> ORGANISM: Mus musculus

<400> SEQUENCE: 172

Thr Asn His Gln Arg Asn Glu Glu Pro Ser Ser
1               5                   10

<210> SEQ ID NO 173

```
<211> LENGTH: 12
<212> TYPE: PRT
<213> ORGANISM: Mus musculus

<400> SEQUENCE: 173

Glu His Pro Ser Thr Ala Asn Thr Val Asp Arg Thr
1               5                   10

<210> SEQ ID NO 174
<211> LENGTH: 12
<212> TYPE: PRT
<213> ORGANISM: Mus musculus

<400> SEQUENCE: 174

His Pro Ser Thr Ala Asn Thr Val Asp Arg Thr Asn
1               5                   10

<210> SEQ ID NO 175
<211> LENGTH: 12
<212> TYPE: PRT
<213> ORGANISM: Mus musculus

<400> SEQUENCE: 175

Pro Ser Thr Ala Asn Thr Val Asp Arg Thr Asn His
1               5                   10

<210> SEQ ID NO 176
<211> LENGTH: 12
<212> TYPE: PRT
<213> ORGANISM: Mus musculus

<400> SEQUENCE: 176

Ser Thr Ala Asn Thr Val Asp Arg Thr Asn His Gln
1               5                   10

<210> SEQ ID NO 177
<211> LENGTH: 12
<212> TYPE: PRT
<213> ORGANISM: Mus musculus

<400> SEQUENCE: 177

Thr Ala Asn Thr Val Asp Arg Thr Asn His Gln Arg
1               5                   10

<210> SEQ ID NO 178
<211> LENGTH: 12
<212> TYPE: PRT
<213> ORGANISM: Mus musculus

<400> SEQUENCE: 178

Ala Asn Thr Val Asp Arg Thr Asn His Gln Arg Asn
1               5                   10

<210> SEQ ID NO 179
<211> LENGTH: 12
<212> TYPE: PRT
<213> ORGANISM: Mus musculus

<400> SEQUENCE: 179

Asn Thr Val Asp Arg Thr Asn His Gln Arg Asn Glu
1               5                   10

<210> SEQ ID NO 180
<211> LENGTH: 12
<212> TYPE: PRT
```

<213> ORGANISM: Mus musculus

<400> SEQUENCE: 180

Thr Val Asp Arg Thr Asn His Gln Arg Asn Glu Glu
1               5                   10

<210> SEQ ID NO 181
<211> LENGTH: 12
<212> TYPE: PRT
<213> ORGANISM: Mus musculus

<400> SEQUENCE: 181

Val Asp Arg Thr Asn His Gln Arg Asn Glu Glu Pro
1               5                   10

<210> SEQ ID NO 182
<211> LENGTH: 12
<212> TYPE: PRT
<213> ORGANISM: Mus musculus

<400> SEQUENCE: 182

Asp Arg Thr Asn His Gln Arg Asn Glu Glu Pro Ser
1               5                   10

<210> SEQ ID NO 183
<211> LENGTH: 12
<212> TYPE: PRT
<213> ORGANISM: Mus musculus

<400> SEQUENCE: 183

Arg Thr Asn His Gln Arg Asn Glu Glu Pro Ser Ser
1               5                   10

<210> SEQ ID NO 184
<211> LENGTH: 13
<212> TYPE: PRT
<213> ORGANISM: Mus musculus

<400> SEQUENCE: 184

Glu His Pro Ser Thr Ala Asn Thr Val Asp Arg Thr Asn
1               5                   10

<210> SEQ ID NO 185
<211> LENGTH: 13
<212> TYPE: PRT
<213> ORGANISM: Mus musculus

<400> SEQUENCE: 185

His Pro Ser Thr Ala Asn Thr Val Asp Arg Thr Asn His
1               5                   10

<210> SEQ ID NO 186
<211> LENGTH: 13
<212> TYPE: PRT
<213> ORGANISM: Mus musculus

<400> SEQUENCE: 186

Pro Ser Thr Ala Asn Thr Val Asp Arg Thr Asn His Gln
1               5                   10

<210> SEQ ID NO 187
<211> LENGTH: 13
<212> TYPE: PRT
<213> ORGANISM: Mus musculus

```
<400> SEQUENCE: 187

Ser Thr Ala Asn Thr Val Asp Arg Thr Asn His Gln Arg
1               5                   10

<210> SEQ ID NO 188
<211> LENGTH: 13
<212> TYPE: PRT
<213> ORGANISM: Mus musculus

<400> SEQUENCE: 188

Thr Ala Asn Thr Val Asp Arg Thr Asn His Gln Arg Asn
1               5                   10

<210> SEQ ID NO 189
<211> LENGTH: 13
<212> TYPE: PRT
<213> ORGANISM: Mus musculus

<400> SEQUENCE: 189

Ala Asn Thr Val Asp Arg Thr Asn His Gln Arg Asn Glu
1               5                   10

<210> SEQ ID NO 190
<211> LENGTH: 13
<212> TYPE: PRT
<213> ORGANISM: Mus musculus

<400> SEQUENCE: 190

Asn Thr Val Asp Arg Thr Asn His Gln Arg Asn Glu Glu
1               5                   10

<210> SEQ ID NO 191
<211> LENGTH: 13
<212> TYPE: PRT
<213> ORGANISM: Mus musculus

<400> SEQUENCE: 191

Thr Val Asp Arg Thr Asn His Gln Arg Asn Glu Glu Pro
1               5                   10

<210> SEQ ID NO 192
<211> LENGTH: 13
<212> TYPE: PRT
<213> ORGANISM: Mus musculus

<400> SEQUENCE: 192

Val Asp Arg Thr Asn His Gln Arg Asn Glu Glu Pro Ser
1               5                   10

<210> SEQ ID NO 193
<211> LENGTH: 13
<212> TYPE: PRT
<213> ORGANISM: Mus musculus

<400> SEQUENCE: 193

Asp Arg Thr Asn His Gln Arg Asn Glu Glu Pro Ser Ser
1               5                   10

<210> SEQ ID NO 194
<211> LENGTH: 14
<212> TYPE: PRT
<213> ORGANISM: Mus musculus

<400> SEQUENCE: 194
```

Glu His Pro Ser Thr Ala Asn Thr Val Asp Arg Thr Asn His
1               5                   10

<210> SEQ ID NO 195
<211> LENGTH: 14
<212> TYPE: PRT
<213> ORGANISM: Mus musculus

<400> SEQUENCE: 195

His Pro Ser Thr Ala Asn Thr Val Asp Arg Thr Asn His Gln
1               5                   10

<210> SEQ ID NO 196
<211> LENGTH: 14
<212> TYPE: PRT
<213> ORGANISM: Mus musculus

<400> SEQUENCE: 196

Pro Ser Thr Ala Asn Thr Val Asp Arg Thr Asn His Gln Arg
1               5                   10

<210> SEQ ID NO 197
<211> LENGTH: 14
<212> TYPE: PRT
<213> ORGANISM: Mus musculus

<400> SEQUENCE: 197

Ser Thr Ala Asn Thr Val Asp Arg Thr Asn His Gln Arg Asn
1               5                   10

<210> SEQ ID NO 198
<211> LENGTH: 14
<212> TYPE: PRT
<213> ORGANISM: Mus musculus

<400> SEQUENCE: 198

Thr Ala Asn Thr Val Asp Arg Thr Asn His Gln Arg Asn Glu
1               5                   10

<210> SEQ ID NO 199
<211> LENGTH: 14
<212> TYPE: PRT
<213> ORGANISM: Mus musculus

<400> SEQUENCE: 199

Ala Asn Thr Val Asp Arg Thr Asn His Gln Arg Asn Glu Glu
1               5                   10

<210> SEQ ID NO 200
<211> LENGTH: 14
<212> TYPE: PRT
<213> ORGANISM: Mus musculus

<400> SEQUENCE: 200

Asn Thr Val Asp Arg Thr Asn His Gln Arg Asn Glu Glu Pro
1               5                   10

<210> SEQ ID NO 201
<211> LENGTH: 14
<212> TYPE: PRT
<213> ORGANISM: Mus musculus

<400> SEQUENCE: 201

Thr Val Asp Arg Thr Asn His Gln Arg Asn Glu Glu Pro Ser
1               5                   10

<210> SEQ ID NO 202
<211> LENGTH: 14
<212> TYPE: PRT
<213> ORGANISM: Mus musculus

<400> SEQUENCE: 202

Val Asp Arg Thr Asn His Gln Arg Asn Glu Glu Pro Ser Ser
1               5                   10

<210> SEQ ID NO 203
<211> LENGTH: 15
<212> TYPE: PRT
<213> ORGANISM: Mus musculus

<400> SEQUENCE: 203

Glu His Pro Ser Thr Ala Asn Thr Val Asp Arg Thr Asn His Gln
1               5                   10                  15

<210> SEQ ID NO 204
<211> LENGTH: 15
<212> TYPE: PRT
<213> ORGANISM: Mus musculus

<400> SEQUENCE: 204

His Pro Ser Thr Ala Asn Thr Val Asp Arg Thr Asn His Gln Arg
1               5                   10                  15

<210> SEQ ID NO 205
<211> LENGTH: 15
<212> TYPE: PRT
<213> ORGANISM: Mus musculus

<400> SEQUENCE: 205

Pro Ser Thr Ala Asn Thr Val Asp Arg Thr Asn His Gln Arg Asn
1               5                   10                  15

<210> SEQ ID NO 206
<211> LENGTH: 15
<212> TYPE: PRT
<213> ORGANISM: Mus musculus

<400> SEQUENCE: 206

Ser Thr Ala Asn Thr Val Asp Arg Thr Asn His Gln Arg Asn Glu
1               5                   10                  15

<210> SEQ ID NO 207
<211> LENGTH: 15
<212> TYPE: PRT
<213> ORGANISM: Mus musculus

<400> SEQUENCE: 207

Thr Ala Asn Thr Val Asp Arg Thr Asn His Gln Arg Asn Glu Glu
1               5                   10                  15

<210> SEQ ID NO 208
<211> LENGTH: 15
<212> TYPE: PRT
<213> ORGANISM: Mus musculus

<400> SEQUENCE: 208

Ala Asn Thr Val Asp Arg Thr Asn His Gln Arg Asn Glu Glu Pro
1               5                   10                  15

```
<210> SEQ ID NO 209
<211> LENGTH: 15
<212> TYPE: PRT
<213> ORGANISM: Mus musculus

<400> SEQUENCE: 209

Asn Thr Val Asp Arg Thr Asn His Gln Arg Asn Glu Glu Pro Ser
1               5                   10                  15

<210> SEQ ID NO 210
<211> LENGTH: 15
<212> TYPE: PRT
<213> ORGANISM: Mus musculus

<400> SEQUENCE: 210

Thr Val Asp Arg Thr Asn His Gln Arg Asn Glu Glu Pro Ser Ser
1               5                   10                  15

<210> SEQ ID NO 211
<211> LENGTH: 16
<212> TYPE: PRT
<213> ORGANISM: Mus musculus

<400> SEQUENCE: 211

Glu His Pro Ser Thr Ala Asn Thr Val Asp Arg Thr Asn His Gln Arg
1               5                   10                  15

<210> SEQ ID NO 212
<211> LENGTH: 16
<212> TYPE: PRT
<213> ORGANISM: Mus musculus

<400> SEQUENCE: 212

His Pro Ser Thr Ala Asn Thr Val Asp Arg Thr Asn His Gln Arg Asn
1               5                   10                  15

<210> SEQ ID NO 213
<211> LENGTH: 16
<212> TYPE: PRT
<213> ORGANISM: Mus musculus

<400> SEQUENCE: 213

Pro Ser Thr Ala Asn Thr Val Asp Arg Thr Asn His Gln Arg Asn Glu
1               5                   10                  15

<210> SEQ ID NO 214
<211> LENGTH: 16
<212> TYPE: PRT
<213> ORGANISM: Mus musculus

<400> SEQUENCE: 214

Ser Thr Ala Asn Thr Val Asp Arg Thr Asn His Gln Arg Asn Glu Glu
1               5                   10                  15

<210> SEQ ID NO 215
<211> LENGTH: 16
<212> TYPE: PRT
<213> ORGANISM: Mus musculus

<400> SEQUENCE: 215

Thr Ala Asn Thr Val Asp Arg Thr Asn His Gln Arg Asn Glu Glu Pro
1               5                   10                  15

<210> SEQ ID NO 216
<211> LENGTH: 16
```

```
<212> TYPE: PRT
<213> ORGANISM: Mus musculus

<400> SEQUENCE: 216

Ala Asn Thr Val Asp Arg Thr Asn His Gln Arg Asn Glu Glu Pro Ser
1               5                   10                  15

<210> SEQ ID NO 217
<211> LENGTH: 16
<212> TYPE: PRT
<213> ORGANISM: Mus musculus

<400> SEQUENCE: 217

Asn Thr Val Asp Arg Thr Asn His Gln Arg Asn Glu Glu Pro Ser Ser
1               5                   10                  15

<210> SEQ ID NO 218
<211> LENGTH: 16
<212> TYPE: PRT
<213> ORGANISM: Mus musculus

<400> SEQUENCE: 218

Glu His Pro Ser Thr Ala Asn Thr Val Asp Arg Thr Asn His Gln Arg
1               5                   10                  15

<210> SEQ ID NO 219
<211> LENGTH: 16
<212> TYPE: PRT
<213> ORGANISM: Mus musculus

<400> SEQUENCE: 219

His Pro Ser Thr Ala Asn Thr Val Asp Arg Thr Asn His Gln Arg Asn
1               5                   10                  15

<210> SEQ ID NO 220
<211> LENGTH: 16
<212> TYPE: PRT
<213> ORGANISM: Mus musculus

<400> SEQUENCE: 220

Pro Ser Thr Ala Asn Thr Val Asp Arg Thr Asn His Gln Arg Asn Glu
1               5                   10                  15

<210> SEQ ID NO 221
<211> LENGTH: 16
<212> TYPE: PRT
<213> ORGANISM: Mus musculus

<400> SEQUENCE: 221

Ser Thr Ala Asn Thr Val Asp Arg Thr Asn His Gln Arg Asn Glu Glu
1               5                   10                  15

<210> SEQ ID NO 222
<211> LENGTH: 16
<212> TYPE: PRT
<213> ORGANISM: Mus musculus

<400> SEQUENCE: 222

Thr Ala Asn Thr Val Asp Arg Thr Asn His Gln Arg Asn Glu Glu Pro
1               5                   10                  15

<210> SEQ ID NO 223
<211> LENGTH: 16
<212> TYPE: PRT
<213> ORGANISM: Mus musculus
```

-continued

<400> SEQUENCE: 223

Ala Asn Thr Val Asp Arg Thr Asn His Gln Arg Asn Glu Glu Pro Ser
1               5                   10                  15

<210> SEQ ID NO 224
<211> LENGTH: 16
<212> TYPE: PRT
<213> ORGANISM: Mus musculus

<400> SEQUENCE: 224

Asn Thr Val Asp Arg Thr Asn His Gln Arg Asn Glu Glu Pro Ser Ser
1               5                   10                  15

<210> SEQ ID NO 225
<211> LENGTH: 17
<212> TYPE: PRT
<213> ORGANISM: Mus musculus

<400> SEQUENCE: 225

Glu His Pro Ser Thr Ala Asn Thr Val Asp Arg Thr Asn His Gln Arg
1               5                   10                  15
Asn

<210> SEQ ID NO 226
<211> LENGTH: 17
<212> TYPE: PRT
<213> ORGANISM: Mus musculus

<400> SEQUENCE: 226

His Pro Ser Thr Ala Asn Thr Val Asp Arg Thr Asn His Gln Arg Asn
1               5                   10                  15
Glu

<210> SEQ ID NO 227
<211> LENGTH: 17
<212> TYPE: PRT
<213> ORGANISM: Mus musculus

<400> SEQUENCE: 227

Pro Ser Thr Ala Asn Thr Val Asp Arg Thr Asn His Gln Arg Asn Glu
1               5                   10                  15
Glu

<210> SEQ ID NO 228
<211> LENGTH: 17
<212> TYPE: PRT
<213> ORGANISM: Mus musculus

<400> SEQUENCE: 228

Ser Thr Ala Asn Thr Val Asp Arg Thr Asn His Gln Arg Asn Glu Glu
1               5                   10                  15
Pro

<210> SEQ ID NO 229
<211> LENGTH: 17
<212> TYPE: PRT
<213> ORGANISM: Mus musculus

<400> SEQUENCE: 229

Thr Ala Asn Thr Val Asp Arg Thr Asn His Gln Arg Asn Glu Glu Pro
1               5                   10                  15

Ser

<210> SEQ ID NO 230
<211> LENGTH: 17
<212> TYPE: PRT
<213> ORGANISM: Mus musculus

<400> SEQUENCE: 230

Ala Asn Thr Val Asp Arg Thr Asn His Gln Arg Asn Glu Glu Pro Ser
1               5                   10                  15

Ser

<210> SEQ ID NO 231
<211> LENGTH: 18
<212> TYPE: PRT
<213> ORGANISM: Mus musculus

<400> SEQUENCE: 231

Glu His Pro Ser Thr Ala Asn Thr Val Asp Arg Thr Asn His Gln Arg
1               5                   10                  15

Asn Glu

<210> SEQ ID NO 232
<211> LENGTH: 18
<212> TYPE: PRT
<213> ORGANISM: Mus musculus

<400> SEQUENCE: 232

His Pro Ser Thr Ala Asn Thr Val Asp Arg Thr Asn His Gln Arg Asn
1               5                   10                  15

Glu Glu

<210> SEQ ID NO 233
<211> LENGTH: 18
<212> TYPE: PRT
<213> ORGANISM: Mus musculus

<400> SEQUENCE: 233

Pro Ser Thr Ala Asn Thr Val Asp Arg Thr Asn His Gln Arg Asn Glu
1               5                   10                  15

Glu Pro

<210> SEQ ID NO 234
<211> LENGTH: 18
<212> TYPE: PRT
<213> ORGANISM: Mus musculus

<400> SEQUENCE: 234

Ser Thr Ala Asn Thr Val Asp Arg Thr Asn His Gln Arg Asn Glu Glu
1               5                   10                  15

Pro Ser

<210> SEQ ID NO 235
<211> LENGTH: 18
<212> TYPE: PRT
<213> ORGANISM: Mus musculus

<400> SEQUENCE: 235

Thr Ala Asn Thr Val Asp Arg Thr Asn His Gln Arg Asn Glu Glu Pro
1               5                   10                  15

Ser Ser

<210> SEQ ID NO 236
<211> LENGTH: 19
<212> TYPE: PRT
<213> ORGANISM: Mus musculus

<400> SEQUENCE: 236

Glu His Pro Ser Thr Ala Asn Thr Val Asp Arg Thr Asn His Gln Arg
1               5                   10                  15

Asn Glu Glu

<210> SEQ ID NO 237
<211> LENGTH: 19
<212> TYPE: PRT
<213> ORGANISM: Mus musculus

<400> SEQUENCE: 237

His Pro Ser Thr Ala Asn Thr Val Asp Arg Thr Asn His Gln Arg Asn
1               5                   10                  15

Glu Glu Pro

<210> SEQ ID NO 238
<211> LENGTH: 19
<212> TYPE: PRT
<213> ORGANISM: Mus musculus

<400> SEQUENCE: 238

Pro Ser Thr Ala Asn Thr Val Asp Arg Thr Asn His Gln Arg Asn Glu
1               5                   10                  15

Glu Pro Ser

<210> SEQ ID NO 239
<211> LENGTH: 19
<212> TYPE: PRT
<213> ORGANISM: Mus musculus

<400> SEQUENCE: 239

Ser Thr Ala Asn Thr Val Asp Arg Thr Asn His Gln Arg Asn Glu Glu
1               5                   10                  15

Pro Ser Ser

<210> SEQ ID NO 240
<211> LENGTH: 20
<212> TYPE: PRT
<213> ORGANISM: Mus musculus

<400> SEQUENCE: 240

Glu His Pro Ser Thr Ala Asn Thr Val Asp Arg Thr Asn His Gln Arg
1               5                   10                  15

Asn Glu Glu Pro
                20

<210> SEQ ID NO 241
<211> LENGTH: 20
<212> TYPE: PRT
<213> ORGANISM: Mus musculus

<400> SEQUENCE: 241

His Pro Ser Thr Ala Asn Thr Val Asp Arg Thr Asn His Gln Arg Asn
1               5                   10                  15

Glu Glu Pro Ser
        20

<210> SEQ ID NO 242
<211> LENGTH: 20
<212> TYPE: PRT
<213> ORGANISM: Mus musculus

<400> SEQUENCE: 242

Pro Ser Thr Ala Asn Thr Val Asp Arg Thr Asn His Gln Arg Asn Glu
1               5                   10                  15

Glu Pro Ser Ser
        20

<210> SEQ ID NO 243
<211> LENGTH: 21
<212> TYPE: PRT
<213> ORGANISM: Mus musculus

<400> SEQUENCE: 243

Glu His Pro Ser Thr Ala Asn Thr Val Asp Arg Thr Asn His Gln Arg
1               5                   10                  15

Asn Glu Glu Pro Ser
        20

<210> SEQ ID NO 244
<211> LENGTH: 21
<212> TYPE: PRT
<213> ORGANISM: Mus musculus

<400> SEQUENCE: 244

His Pro Ser Thr Ala Asn Thr Val Asp Arg Thr Asn His Gln Arg Asn
1               5                   10                  15

Glu Glu Pro Ser Ser
        20

<210> SEQ ID NO 245
<211> LENGTH: 22
<212> TYPE: PRT
<213> ORGANISM: Mus musculus

<400> SEQUENCE: 245

Glu His Pro Ser Thr Ala Asn Thr Val Asp Arg Thr Asn His Gln Arg
1               5                   10                  15

Asn Glu Glu Pro Ser Ser
        20

<210> SEQ ID NO 246
<211> LENGTH: 5
<212> TYPE: PRT
<213> ORGANISM: Homo sapiens

<400> SEQUENCE: 246

Asp His Pro Ser Thr
1               5

<210> SEQ ID NO 247
<211> LENGTH: 5
<212> TYPE: PRT
<213> ORGANISM: Homo sapiens

<400> SEQUENCE: 247

Ala Asn Thr Val Asp

```
1               5

<210> SEQ ID NO 248
<211> LENGTH: 5
<212> TYPE: PRT
<213> ORGANISM: Homo sapiens

<400> SEQUENCE: 248

Arg Thr Asn His Gln
1               5

<210> SEQ ID NO 249
<211> LENGTH: 5
<212> TYPE: PRT
<213> ORGANISM: Homo sapiens

<400> SEQUENCE: 249

Arg Glu Arg Arg Gln
1               5

<210> SEQ ID NO 250
<211> LENGTH: 5
<212> TYPE: PRT
<213> ORGANISM: Homo sapiens

<400> SEQUENCE: 250

His Pro Ser Thr Ala
1               5

<210> SEQ ID NO 251
<211> LENGTH: 5
<212> TYPE: PRT
<213> ORGANISM: Homo sapiens

<400> SEQUENCE: 251

Asn Thr Val Asp Arg
1               5

<210> SEQ ID NO 252
<211> LENGTH: 5
<212> TYPE: PRT
<213> ORGANISM: Homo sapiens

<400> SEQUENCE: 252

Thr Asn His Gln Arg
1               5

<210> SEQ ID NO 253
<211> LENGTH: 5
<212> TYPE: PRT
<213> ORGANISM: Homo sapiens

<400> SEQUENCE: 253

Glu Arg Arg Gln Lys
1               5

<210> SEQ ID NO 254
<211> LENGTH: 5
<212> TYPE: PRT
<213> ORGANISM: Homo sapiens

<400> SEQUENCE: 254

Pro Ser Thr Ala Asn
1               5
```

<210> SEQ ID NO 255
<211> LENGTH: 5
<212> TYPE: PRT
<213> ORGANISM: Homo sapiens

<400> SEQUENCE: 255

Thr Val Asp Arg Thr
1               5

<210> SEQ ID NO 256
<211> LENGTH: 5
<212> TYPE: PRT
<213> ORGANISM: Homo sapiens

<400> SEQUENCE: 256

Asn His Gln Arg Glu
1               5

<210> SEQ ID NO 257
<211> LENGTH: 5
<212> TYPE: PRT
<213> ORGANISM: Homo sapiens

<400> SEQUENCE: 257

Arg Arg Gln Lys Ser
1               5

<210> SEQ ID NO 258
<211> LENGTH: 5
<212> TYPE: PRT
<213> ORGANISM: Homo sapiens

<400> SEQUENCE: 258

Ser Thr Ala Asn Thr
1               5

<210> SEQ ID NO 259
<211> LENGTH: 5
<212> TYPE: PRT
<213> ORGANISM: Homo sapiens

<400> SEQUENCE: 259

Val Asp Arg Thr Asn
1               5

<210> SEQ ID NO 260
<211> LENGTH: 5
<212> TYPE: PRT
<213> ORGANISM: Homo sapiens

<400> SEQUENCE: 260

His Gln Arg Glu Arg
1               5

<210> SEQ ID NO 261
<211> LENGTH: 5
<212> TYPE: PRT
<213> ORGANISM: Homo sapiens

<400> SEQUENCE: 261

Arg Gln Lys Ser Asp
1               5

<210> SEQ ID NO 262

```
<211> LENGTH: 5
<212> TYPE: PRT
<213> ORGANISM: Homo sapiens

<400> SEQUENCE: 262

Thr Ala Asn Thr Val
1               5

<210> SEQ ID NO 263
<211> LENGTH: 5
<212> TYPE: PRT
<213> ORGANISM: Homo sapiens

<400> SEQUENCE: 263

Asp Arg Thr Asn His
1               5

<210> SEQ ID NO 264
<211> LENGTH: 5
<212> TYPE: PRT
<213> ORGANISM: Homo sapiens

<400> SEQUENCE: 264

Gln Arg Glu Arg Arg
1               5

<210> SEQ ID NO 265
<211> LENGTH: 5
<212> TYPE: PRT
<213> ORGANISM: Homo sapiens

<400> SEQUENCE: 265

Gln Lys Ser Asp Trp
1               5

<210> SEQ ID NO 266
<211> LENGTH: 5
<212> TYPE: PRT
<213> ORGANISM: Homo sapiens

<400> SEQUENCE: 266

Ala Asn Thr Val Asp
1               5

<210> SEQ ID NO 267
<211> LENGTH: 5
<212> TYPE: PRT
<213> ORGANISM: Homo sapiens

<400> SEQUENCE: 267

Arg Thr Asn His Gln
1               5

<210> SEQ ID NO 268
<211> LENGTH: 5
<212> TYPE: PRT
<213> ORGANISM: Homo sapiens

<400> SEQUENCE: 268

Arg Glu Arg Arg Gln
1               5

<210> SEQ ID NO 269
<211> LENGTH: 5
<212> TYPE: PRT
```

```
<213> ORGANISM: Homo sapiens

<400> SEQUENCE: 269

Asn Thr Val Asp Arg
1               5

<210> SEQ ID NO 270
<211> LENGTH: 5
<212> TYPE: PRT
<213> ORGANISM: Homo sapiens

<400> SEQUENCE: 270

Thr Asn His Gln Arg
1               5

<210> SEQ ID NO 271
<211> LENGTH: 5
<212> TYPE: PRT
<213> ORGANISM: Homo sapiens

<400> SEQUENCE: 271

Glu Arg Arg Gln Lys
1               5

<210> SEQ ID NO 272
<211> LENGTH: 5
<212> TYPE: PRT
<213> ORGANISM: Homo sapiens

<400> SEQUENCE: 272

Thr Val Asp Arg Thr
1               5

<210> SEQ ID NO 273
<211> LENGTH: 5
<212> TYPE: PRT
<213> ORGANISM: Homo sapiens

<400> SEQUENCE: 273

Asn His Gln Arg Glu
1               5

<210> SEQ ID NO 274
<211> LENGTH: 5
<212> TYPE: PRT
<213> ORGANISM: Homo sapiens

<400> SEQUENCE: 274

Arg Arg Gln Lys Ser
1               5

<210> SEQ ID NO 275
<211> LENGTH: 5
<212> TYPE: PRT
<213> ORGANISM: Homo sapiens

<400> SEQUENCE: 275

Val Asp Arg Thr Asn
1               5

<210> SEQ ID NO 276
<211> LENGTH: 5
<212> TYPE: PRT
<213> ORGANISM: Homo sapiens
```

```
<400> SEQUENCE: 276

His Gln Arg Glu Arg
1               5

<210> SEQ ID NO 277
<211> LENGTH: 5
<212> TYPE: PRT
<213> ORGANISM: Homo sapiens

<400> SEQUENCE: 277

Arg Gln Lys Ser Asp
1               5

<210> SEQ ID NO 278
<211> LENGTH: 5
<212> TYPE: PRT
<213> ORGANISM: Homo sapiens

<400> SEQUENCE: 278

Gln Lys Ser Asp Trp
1               5

<210> SEQ ID NO 279
<211> LENGTH: 5
<212> TYPE: PRT
<213> ORGANISM: Homo sapiens

<400> SEQUENCE: 279

Asp Arg Thr Asn His
1               5

<210> SEQ ID NO 280
<211> LENGTH: 5
<212> TYPE: PRT
<213> ORGANISM: Homo sapiens

<400> SEQUENCE: 280

Gln Arg Glu Arg Arg
1               5

<210> SEQ ID NO 281
<211> LENGTH: 5
<212> TYPE: PRT
<213> ORGANISM: Homo sapiens

<400> SEQUENCE: 281

Gln Lys Ser Asp Trp
1               5

<210> SEQ ID NO 282
<211> LENGTH: 5
<212> TYPE: PRT
<213> ORGANISM: Homo sapiens

<400> SEQUENCE: 282

Arg Thr Asn His Gln
1               5

<210> SEQ ID NO 283
<211> LENGTH: 5
<212> TYPE: PRT
<213> ORGANISM: Homo sapiens

<400> SEQUENCE: 283
```

Arg Glu Arg Arg Gln
1               5

<210> SEQ ID NO 284
<211> LENGTH: 5
<212> TYPE: PRT
<213> ORGANISM: Homo sapiens

<400> SEQUENCE: 284

Thr Asn His Gln Arg
1               5

<210> SEQ ID NO 285
<211> LENGTH: 5
<212> TYPE: PRT
<213> ORGANISM: Homo sapiens

<400> SEQUENCE: 285

Glu Arg Arg Gln Lys
1               5

<210> SEQ ID NO 286
<211> LENGTH: 5
<212> TYPE: PRT
<213> ORGANISM: Homo sapiens

<400> SEQUENCE: 286

Asn His Gln Arg Glu
1               5

<210> SEQ ID NO 287
<211> LENGTH: 5
<212> TYPE: PRT
<213> ORGANISM: Homo sapiens

<400> SEQUENCE: 287

Arg Arg Gln Lys Ser
1               5

<210> SEQ ID NO 288
<211> LENGTH: 5
<212> TYPE: PRT
<213> ORGANISM: Homo sapiens

<400> SEQUENCE: 288

His Gln Arg Glu Arg
1               5

<210> SEQ ID NO 289
<211> LENGTH: 5
<212> TYPE: PRT
<213> ORGANISM: Homo sapiens

<400> SEQUENCE: 289

Arg Gln Lys Ser Asp
1               5

<210> SEQ ID NO 290
<211> LENGTH: 5
<212> TYPE: PRT
<213> ORGANISM: Homo sapiens

<400> SEQUENCE: 290

Gln Arg Glu Arg Arg
1               5

```
<210> SEQ ID NO 291
<211> LENGTH: 5
<212> TYPE: PRT
<213> ORGANISM: Homo sapiens

<400> SEQUENCE: 291

Gln Lys Ser Asp Trp
1               5

<210> SEQ ID NO 292
<211> LENGTH: 5
<212> TYPE: PRT
<213> ORGANISM: Homo sapiens

<400> SEQUENCE: 292

Arg Glu Arg Arg Gln
1               5

<210> SEQ ID NO 293
<211> LENGTH: 5
<212> TYPE: PRT
<213> ORGANISM: Homo sapiens

<400> SEQUENCE: 293

Glu Arg Arg Gln Lys
1               5

<210> SEQ ID NO 294
<211> LENGTH: 5
<212> TYPE: PRT
<213> ORGANISM: Homo sapiens

<400> SEQUENCE: 294

Arg Arg Gln Lys Ser
1               5

<210> SEQ ID NO 295
<211> LENGTH: 5
<212> TYPE: PRT
<213> ORGANISM: Homo sapiens

<400> SEQUENCE: 295

Arg Gln Lys Ser Asp
1               5

<210> SEQ ID NO 296
<211> LENGTH: 5
<212> TYPE: PRT
<213> ORGANISM: Homo sapiens

<400> SEQUENCE: 296

Gln Lys Ser Asp Trp
1               5

<210> SEQ ID NO 297
<211> LENGTH: 6
<212> TYPE: PRT
<213> ORGANISM: Homo sapiens

<400> SEQUENCE: 297

Asp His Pro Ser Thr Ala
1               5
```

```
<210> SEQ ID NO 298
<211> LENGTH: 6
<212> TYPE: PRT
<213> ORGANISM: Homo sapiens

<400> SEQUENCE: 298

Asn Thr Val Asp Arg Thr
1               5

<210> SEQ ID NO 299
<211> LENGTH: 6
<212> TYPE: PRT
<213> ORGANISM: Homo sapiens

<400> SEQUENCE: 299

Asn His Gln Arg Glu Arg
1               5

<210> SEQ ID NO 300
<211> LENGTH: 6
<212> TYPE: PRT
<213> ORGANISM: Homo sapiens

<400> SEQUENCE: 300

Arg Gln Lys Ser Asp Trp
1               5

<210> SEQ ID NO 301
<211> LENGTH: 6
<212> TYPE: PRT
<213> ORGANISM: Homo sapiens

<400> SEQUENCE: 301

His Pro Ser Thr Ala Asn
1               5

<210> SEQ ID NO 302
<211> LENGTH: 6
<212> TYPE: PRT
<213> ORGANISM: Homo sapiens

<400> SEQUENCE: 302

Thr Val Asp Arg Thr Asn
1               5

<210> SEQ ID NO 303
<211> LENGTH: 6
<212> TYPE: PRT
<213> ORGANISM: Homo sapiens

<400> SEQUENCE: 303

His Gln Arg Glu Arg Arg
1               5

<210> SEQ ID NO 304
<211> LENGTH: 6
<212> TYPE: PRT
<213> ORGANISM: Homo sapiens

<400> SEQUENCE: 304

Pro Ser Thr Ala Asn Thr
1               5

<210> SEQ ID NO 305
<211> LENGTH: 6
```

```
<212> TYPE: PRT
<213> ORGANISM: Homo sapiens

<400> SEQUENCE: 305

Val Asp Arg Thr Asn His
1               5

<210> SEQ ID NO 306
<211> LENGTH: 6
<212> TYPE: PRT
<213> ORGANISM: Homo sapiens

<400> SEQUENCE: 306

Gln Arg Glu Arg Arg Gln
1               5

<210> SEQ ID NO 307
<211> LENGTH: 6
<212> TYPE: PRT
<213> ORGANISM: Homo sapiens

<400> SEQUENCE: 307

Ser Thr Ala Asn Thr Val
1               5

<210> SEQ ID NO 308
<211> LENGTH: 6
<212> TYPE: PRT
<213> ORGANISM: Homo sapiens

<400> SEQUENCE: 308

Asp Arg Thr Asn His Gln
1               5

<210> SEQ ID NO 309
<211> LENGTH: 6
<212> TYPE: PRT
<213> ORGANISM: Homo sapiens

<400> SEQUENCE: 309

Arg Glu Arg Arg Gln Lys
1               5

<210> SEQ ID NO 310
<211> LENGTH: 6
<212> TYPE: PRT
<213> ORGANISM: Homo sapiens

<400> SEQUENCE: 310

Thr Ala Asn Thr Val Asp
1               5

<210> SEQ ID NO 311
<211> LENGTH: 6
<212> TYPE: PRT
<213> ORGANISM: Homo sapiens

<400> SEQUENCE: 311

Arg Thr Asn His Gln Arg
1               5

<210> SEQ ID NO 312
<211> LENGTH: 6
<212> TYPE: PRT
<213> ORGANISM: Homo sapiens
```

```
<400> SEQUENCE: 312

Glu Arg Arg Gln Lys Ser
1               5

<210> SEQ ID NO 313
<211> LENGTH: 6
<212> TYPE: PRT
<213> ORGANISM: Homo sapiens

<400> SEQUENCE: 313

Ala Asn Thr Val Asp Arg
1               5

<210> SEQ ID NO 314
<211> LENGTH: 6
<212> TYPE: PRT
<213> ORGANISM: Homo sapiens

<400> SEQUENCE: 314

Thr Asn His Gln Arg Glu
1               5

<210> SEQ ID NO 315
<211> LENGTH: 6
<212> TYPE: PRT
<213> ORGANISM: Homo sapiens

<400> SEQUENCE: 315

Arg Arg Gln Lys Ser Asp
1               5

<210> SEQ ID NO 316
<211> LENGTH: 6
<212> TYPE: PRT
<213> ORGANISM: Homo sapiens

<400> SEQUENCE: 316

Asn Thr Val Asp Arg Thr
1               5

<210> SEQ ID NO 317
<211> LENGTH: 6
<212> TYPE: PRT
<213> ORGANISM: Homo sapiens

<400> SEQUENCE: 317

Asn His Gln Arg Glu Arg
1               5

<210> SEQ ID NO 318
<211> LENGTH: 6
<212> TYPE: PRT
<213> ORGANISM: Homo sapiens

<400> SEQUENCE: 318

Arg Gln Lys Ser Asp Trp
1               5

<210> SEQ ID NO 319
<211> LENGTH: 6
<212> TYPE: PRT
<213> ORGANISM: Homo sapiens

<400> SEQUENCE: 319
```

Thr Val Asp Arg Thr Asn
1               5

<210> SEQ ID NO 320
<211> LENGTH: 6
<212> TYPE: PRT
<213> ORGANISM: Homo sapiens

<400> SEQUENCE: 320

His Gln Arg Glu Arg Arg
1               5

<210> SEQ ID NO 321
<211> LENGTH: 6
<212> TYPE: PRT
<213> ORGANISM: Homo sapiens

<400> SEQUENCE: 321

Val Asp Arg Thr Asn His
1               5

<210> SEQ ID NO 322
<211> LENGTH: 6
<212> TYPE: PRT
<213> ORGANISM: Homo sapiens

<400> SEQUENCE: 322

Gln Arg Glu Arg Arg Gln
1               5

<210> SEQ ID NO 323
<211> LENGTH: 6
<212> TYPE: PRT
<213> ORGANISM: Homo sapiens

<400> SEQUENCE: 323

Asp Arg Thr Asn His Gln
1               5

<210> SEQ ID NO 324
<211> LENGTH: 6
<212> TYPE: PRT
<213> ORGANISM: Homo sapiens

<400> SEQUENCE: 324

Arg Glu Arg Arg Gln Lys
1               5

<210> SEQ ID NO 325
<211> LENGTH: 6
<212> TYPE: PRT
<213> ORGANISM: Homo sapiens

<400> SEQUENCE: 325

Arg Thr Asn His Gln Arg
1               5

<210> SEQ ID NO 326
<211> LENGTH: 6
<212> TYPE: PRT
<213> ORGANISM: Homo sapiens

<400> SEQUENCE: 326

Glu Arg Arg Gln Lys Ser

<210> SEQ ID NO 327
<211> LENGTH: 6
<212> TYPE: PRT
<213> ORGANISM: Homo sapiens

<400> SEQUENCE: 327

Thr Asn His Gln Arg Glu
1               5

<210> SEQ ID NO 328
<211> LENGTH: 6
<212> TYPE: PRT
<213> ORGANISM: Homo sapiens

<400> SEQUENCE: 328

Arg Arg Gln Lys Ser Asp
1               5

<210> SEQ ID NO 329
<211> LENGTH: 6
<212> TYPE: PRT
<213> ORGANISM: Homo sapiens

<400> SEQUENCE: 329

Asn His Gln Arg Glu Arg
1               5

<210> SEQ ID NO 330
<211> LENGTH: 6
<212> TYPE: PRT
<213> ORGANISM: Homo sapiens

<400> SEQUENCE: 330

Arg Gln Lys Ser Asp Trp
1               5

<210> SEQ ID NO 331
<211> LENGTH: 6
<212> TYPE: PRT
<213> ORGANISM: Homo sapiens

<400> SEQUENCE: 331

His Gln Arg Glu Arg Arg
1               5

<210> SEQ ID NO 332
<211> LENGTH: 6
<212> TYPE: PRT
<213> ORGANISM: Homo sapiens

<400> SEQUENCE: 332

Gln Arg Glu Arg Arg Gln
1               5

<210> SEQ ID NO 333
<211> LENGTH: 6
<212> TYPE: PRT
<213> ORGANISM: Homo sapiens

<400> SEQUENCE: 333

Arg Glu Arg Arg Gln Lys
1               5

<210> SEQ ID NO 334
<211> LENGTH: 6
<212> TYPE: PRT
<213> ORGANISM: Homo sapiens

<400> SEQUENCE: 334

Glu Arg Arg Gln Lys Ser
1               5

<210> SEQ ID NO 335
<211> LENGTH: 6
<212> TYPE: PRT
<213> ORGANISM: Homo sapiens

<400> SEQUENCE: 335

Arg Arg Gln Lys Ser Asp
1               5

<210> SEQ ID NO 336
<211> LENGTH: 6
<212> TYPE: PRT
<213> ORGANISM: Homo sapiens

<400> SEQUENCE: 336

Arg Gln Lys Ser Asp Trp
1               5

<210> SEQ ID NO 337
<211> LENGTH: 7
<212> TYPE: PRT
<213> ORGANISM: Homo sapiens

<400> SEQUENCE: 337

Asp His Pro Ser Thr Ala Asn
1               5

<210> SEQ ID NO 338
<211> LENGTH: 7
<212> TYPE: PRT
<213> ORGANISM: Homo sapiens

<400> SEQUENCE: 338

Thr Val Asp Arg Thr Asn His
1               5

<210> SEQ ID NO 339
<211> LENGTH: 6
<212> TYPE: PRT
<213> ORGANISM: Homo sapiens

<400> SEQUENCE: 339

Gln Arg Glu Arg Arg Gln
1               5

<210> SEQ ID NO 340
<211> LENGTH: 7
<212> TYPE: PRT
<213> ORGANISM: Homo sapiens

<400> SEQUENCE: 340

His Pro Ser Thr Ala Asn Thr
1               5

<210> SEQ ID NO 341

```
<211> LENGTH: 7
<212> TYPE: PRT
<213> ORGANISM: Homo sapiens

<400> SEQUENCE: 341

Val Asp Arg Thr Asn His Gln
1               5

<210> SEQ ID NO 342
<211> LENGTH: 7
<212> TYPE: PRT
<213> ORGANISM: Homo sapiens

<400> SEQUENCE: 342

Arg Glu Arg Arg Gln Lys Ser
1               5

<210> SEQ ID NO 343
<211> LENGTH: 7
<212> TYPE: PRT
<213> ORGANISM: Homo sapiens

<400> SEQUENCE: 343

Pro Ser Thr Ala Asn Thr Val
1               5

<210> SEQ ID NO 344
<211> LENGTH: 7
<212> TYPE: PRT
<213> ORGANISM: Homo sapiens

<400> SEQUENCE: 344

Asp Arg Thr Asn His Gln Arg
1               5

<210> SEQ ID NO 345
<211> LENGTH: 7
<212> TYPE: PRT
<213> ORGANISM: Homo sapiens

<400> SEQUENCE: 345

Glu Arg Arg Gln Lys Ser Asp
1               5

<210> SEQ ID NO 346
<211> LENGTH: 7
<212> TYPE: PRT
<213> ORGANISM: Homo sapiens

<400> SEQUENCE: 346

Arg Arg Gln Lys Ser Asp Trp
1               5

<210> SEQ ID NO 347
<211> LENGTH: 7
<212> TYPE: PRT
<213> ORGANISM: Homo sapiens

<400> SEQUENCE: 347

Ser Thr Ala Asn Thr Val Asp
1               5

<210> SEQ ID NO 348
<211> LENGTH: 7
<212> TYPE: PRT
```

<213> ORGANISM: Homo sapiens

<400> SEQUENCE: 348

Arg Thr Asn His Gln Arg Glu
1               5

<210> SEQ ID NO 349
<211> LENGTH: 7
<212> TYPE: PRT
<213> ORGANISM: Homo sapiens

<400> SEQUENCE: 349

Thr Ala Asn Thr Val Asp Arg
1               5

<210> SEQ ID NO 350
<211> LENGTH: 7
<212> TYPE: PRT
<213> ORGANISM: Homo sapiens

<400> SEQUENCE: 350

Thr Asn His Gln Arg Glu Arg
1               5

<210> SEQ ID NO 351
<211> LENGTH: 7
<212> TYPE: PRT
<213> ORGANISM: Homo sapiens

<400> SEQUENCE: 351

Ala Asn Thr Val Asp Arg Thr
1               5

<210> SEQ ID NO 352
<211> LENGTH: 7
<212> TYPE: PRT
<213> ORGANISM: Homo sapiens

<400> SEQUENCE: 352

Asn His Gln Arg Glu Arg Arg
1               5

<210> SEQ ID NO 353
<211> LENGTH: 7
<212> TYPE: PRT
<213> ORGANISM: Homo sapiens

<400> SEQUENCE: 353

Asn Thr Val Asp Arg Thr Asn
1               5

<210> SEQ ID NO 354
<211> LENGTH: 7
<212> TYPE: PRT
<213> ORGANISM: Homo sapiens

<400> SEQUENCE: 354

His Gln Arg Glu Arg Arg Gln
1               5

<210> SEQ ID NO 355
<211> LENGTH: 7
<212> TYPE: PRT
<213> ORGANISM: Homo sapiens

<400> SEQUENCE: 355

Thr Val Asp Arg Thr Asn His
1               5

<210> SEQ ID NO 356
<211> LENGTH: 7
<212> TYPE: PRT
<213> ORGANISM: Homo sapiens

<400> SEQUENCE: 356

Gln Arg Glu Arg Arg Gln Lys
1               5

<210> SEQ ID NO 357
<211> LENGTH: 7
<212> TYPE: PRT
<213> ORGANISM: Homo sapiens

<400> SEQUENCE: 357

Val Asp Arg Thr Asn His Gln
1               5

<210> SEQ ID NO 358
<211> LENGTH: 7
<212> TYPE: PRT
<213> ORGANISM: Homo sapiens

<400> SEQUENCE: 358

Arg Glu Arg Arg Gln Lys Ser
1               5

<210> SEQ ID NO 359
<211> LENGTH: 7
<212> TYPE: PRT
<213> ORGANISM: Homo sapiens

<400> SEQUENCE: 359

Asp Arg Thr Asn His Gln Arg
1               5

<210> SEQ ID NO 360
<211> LENGTH: 7
<212> TYPE: PRT
<213> ORGANISM: Homo sapiens

<400> SEQUENCE: 360

Glu Arg Arg Gln Lys Ser Asp
1               5

<210> SEQ ID NO 361
<211> LENGTH: 7
<212> TYPE: PRT
<213> ORGANISM: Homo sapiens

<400> SEQUENCE: 361

Arg Thr Asn His Gln Arg Glu
1               5

<210> SEQ ID NO 362
<211> LENGTH: 7
<212> TYPE: PRT
<213> ORGANISM: Homo sapiens

<400> SEQUENCE: 362

Arg Thr Asn His Gln Arg Glu
1               5

<210> SEQ ID NO 363
<211> LENGTH: 7
<212> TYPE: PRT
<213> ORGANISM: Homo sapiens

<400> SEQUENCE: 363

Thr Asn His Gln Arg Glu Arg
1               5

<210> SEQ ID NO 364
<211> LENGTH: 7
<212> TYPE: PRT
<213> ORGANISM: Homo sapiens

<400> SEQUENCE: 364

Asn His Gln Arg Glu Arg Arg
1               5

<210> SEQ ID NO 365
<211> LENGTH: 7
<212> TYPE: PRT
<213> ORGANISM: Homo sapiens

<400> SEQUENCE: 365

His Gln Arg Glu Arg Arg Gln
1               5

<210> SEQ ID NO 366
<211> LENGTH: 7
<212> TYPE: PRT
<213> ORGANISM: Homo sapiens

<400> SEQUENCE: 366

Gln Arg Glu Arg Arg Gln Lys
1               5

<210> SEQ ID NO 367
<211> LENGTH: 7
<212> TYPE: PRT
<213> ORGANISM: Homo sapiens

<400> SEQUENCE: 367

Arg Glu Arg Arg Gln Lys Ser
1               5

<210> SEQ ID NO 368
<211> LENGTH: 7
<212> TYPE: PRT
<213> ORGANISM: Homo sapiens

<400> SEQUENCE: 368

Glu Arg Arg Gln Lys Ser Asp
1               5

<210> SEQ ID NO 369
<211> LENGTH: 7
<212> TYPE: PRT
<213> ORGANISM: Homo sapiens

<400> SEQUENCE: 369

Arg Arg Gln Lys Ser Asp Trp
1               5

<210> SEQ ID NO 370
<211> LENGTH: 8
<212> TYPE: PRT
<213> ORGANISM: Homo sapiens

<400> SEQUENCE: 370

Asp His Pro Ser Thr Ala Asn Thr
1               5

<210> SEQ ID NO 371
<211> LENGTH: 8
<212> TYPE: PRT
<213> ORGANISM: Homo sapiens

<400> SEQUENCE: 371

Val Asp Arg Thr Asn His Gln Arg
1               5

<210> SEQ ID NO 372
<211> LENGTH: 8
<212> TYPE: PRT
<213> ORGANISM: Homo sapiens

<400> SEQUENCE: 372

Glu Arg Arg Gln Lys Ser Asp Trp
1               5

<210> SEQ ID NO 373
<211> LENGTH: 8
<212> TYPE: PRT
<213> ORGANISM: Homo sapiens

<400> SEQUENCE: 373

His Pro Ser Thr Ala Asn Thr Val
1               5

<210> SEQ ID NO 374
<211> LENGTH: 8
<212> TYPE: PRT
<213> ORGANISM: Homo sapiens

<400> SEQUENCE: 374

Asp Arg Thr Asn His Gln Arg Glu
1               5

<210> SEQ ID NO 375
<211> LENGTH: 8
<212> TYPE: PRT
<213> ORGANISM: Homo sapiens

<400> SEQUENCE: 375

Pro Ser Thr Ala Asn Thr Val Asp
1               5

<210> SEQ ID NO 376
<211> LENGTH: 8
<212> TYPE: PRT
<213> ORGANISM: Homo sapiens

<400> SEQUENCE: 376

Arg Thr Asn His Gln Arg Glu Arg
1               5

<210> SEQ ID NO 377
<211> LENGTH: 8
<212> TYPE: PRT
<213> ORGANISM: Homo sapiens

<400> SEQUENCE: 377

Ser Thr Ala Asn Thr Val Asp Arg
1               5

<210> SEQ ID NO 378
<211> LENGTH: 8
<212> TYPE: PRT
<213> ORGANISM: Homo sapiens

<400> SEQUENCE: 378

Thr Asn His Gln Arg Glu Arg Arg
1               5

<210> SEQ ID NO 379
<211> LENGTH: 8
<212> TYPE: PRT
<213> ORGANISM: Homo sapiens

<400> SEQUENCE: 379

Thr Ala Asn Thr Val Asp Arg Thr
1               5

<210> SEQ ID NO 380
<211> LENGTH: 8
<212> TYPE: PRT
<213> ORGANISM: Homo sapiens

<400> SEQUENCE: 380

Asn His Gln Arg Glu Arg Arg Gln
1               5

<210> SEQ ID NO 381
<211> LENGTH: 8
<212> TYPE: PRT
<213> ORGANISM: Homo sapiens

<400> SEQUENCE: 381

Ala Asn Thr Val Asp Arg Thr Asn
1               5

<210> SEQ ID NO 382
<211> LENGTH: 8
<212> TYPE: PRT
<213> ORGANISM: Homo sapiens

<400> SEQUENCE: 382

His Gln Arg Glu Arg Arg Gln Lys
1               5

<210> SEQ ID NO 383
<211> LENGTH: 8
<212> TYPE: PRT
<213> ORGANISM: Homo sapiens

<400> SEQUENCE: 383

Asn Thr Val Asp Arg Thr Asn His
1               5

<210> SEQ ID NO 384
<211> LENGTH: 8

```
<212> TYPE: PRT
<213> ORGANISM: Homo sapiens

<400> SEQUENCE: 384

Gln Arg Glu Arg Arg Gln Lys Ser
1               5

<210> SEQ ID NO 385
<211> LENGTH: 8
<212> TYPE: PRT
<213> ORGANISM: Homo sapiens

<400> SEQUENCE: 385

Thr Val Asp Arg Thr Asn His Gln
1               5

<210> SEQ ID NO 386
<211> LENGTH: 8
<212> TYPE: PRT
<213> ORGANISM: Homo sapiens

<400> SEQUENCE: 386

Arg Glu Arg Arg Gln Lys Ser Asp
1               5

<210> SEQ ID NO 387
<211> LENGTH: 8
<212> TYPE: PRT
<213> ORGANISM: Homo sapiens

<400> SEQUENCE: 387

Val Asp Arg Thr Asn His Gln Arg
1               5

<210> SEQ ID NO 388
<211> LENGTH: 8
<212> TYPE: PRT
<213> ORGANISM: Homo sapiens

<400> SEQUENCE: 388

Glu Arg Arg Gln Lys Ser Asp Trp
1               5

<210> SEQ ID NO 389
<211> LENGTH: 8
<212> TYPE: PRT
<213> ORGANISM: Homo sapiens

<400> SEQUENCE: 389

Asp Arg Thr Asn His Gln Arg Glu
1               5

<210> SEQ ID NO 390
<211> LENGTH: 8
<212> TYPE: PRT
<213> ORGANISM: Homo sapiens

<400> SEQUENCE: 390

Arg Thr Asn His Gln Arg Glu Arg
1               5

<210> SEQ ID NO 391
<211> LENGTH: 8
<212> TYPE: PRT
<213> ORGANISM: Homo sapiens
```

```
<400> SEQUENCE: 391

Thr Asn His Gln Arg Glu Arg Arg
1               5

<210> SEQ ID NO 392
<211> LENGTH: 8
<212> TYPE: PRT
<213> ORGANISM: Homo sapiens

<400> SEQUENCE: 392

Asn His Gln Arg Glu Arg Arg Gln
1               5

<210> SEQ ID NO 393
<211> LENGTH: 8
<212> TYPE: PRT
<213> ORGANISM: Homo sapiens

<400> SEQUENCE: 393

His Gln Arg Glu Arg Arg Gln Lys
1               5

<210> SEQ ID NO 394
<211> LENGTH: 8
<212> TYPE: PRT
<213> ORGANISM: Homo sapiens

<400> SEQUENCE: 394

Gln Arg Glu Arg Arg Gln Lys Ser
1               5

<210> SEQ ID NO 395
<211> LENGTH: 8
<212> TYPE: PRT
<213> ORGANISM: Homo sapiens

<400> SEQUENCE: 395

Arg Glu Arg Arg Gln Lys Ser Asp
1               5

<210> SEQ ID NO 396
<211> LENGTH: 8
<212> TYPE: PRT
<213> ORGANISM: Homo sapiens

<400> SEQUENCE: 396

Glu Arg Arg Gln Lys Ser Asp Trp
1               5

<210> SEQ ID NO 397
<211> LENGTH: 9
<212> TYPE: PRT
<213> ORGANISM: Homo sapiens

<400> SEQUENCE: 397

Asp His Pro Ser Thr Ala Asn Thr Val
1               5

<210> SEQ ID NO 398
<211> LENGTH: 9
<212> TYPE: PRT
<213> ORGANISM: Homo sapiens

<400> SEQUENCE: 398
```

Asp Arg Thr Asn His Gln Arg Glu Arg
1               5

<210> SEQ ID NO 399
<211> LENGTH: 9
<212> TYPE: PRT
<213> ORGANISM: Homo sapiens

<400> SEQUENCE: 399

His Pro Ser Thr Ala Asn Thr Val Asp
1               5

<210> SEQ ID NO 400
<211> LENGTH: 9
<212> TYPE: PRT
<213> ORGANISM: Homo sapiens

<400> SEQUENCE: 400

Arg Thr Asn His Gln Arg Glu Arg Arg
1               5

<210> SEQ ID NO 401
<211> LENGTH: 9
<212> TYPE: PRT
<213> ORGANISM: Homo sapiens

<400> SEQUENCE: 401

Pro Ser Thr Ala Asn Thr Val Asp Arg
1               5

<210> SEQ ID NO 402
<211> LENGTH: 9
<212> TYPE: PRT
<213> ORGANISM: Homo sapiens

<400> SEQUENCE: 402

Thr Asn His Gln Arg Glu Arg Arg Gln
1               5

<210> SEQ ID NO 403
<211> LENGTH: 9
<212> TYPE: PRT
<213> ORGANISM: Homo sapiens

<400> SEQUENCE: 403

Ser Thr Ala Asn Thr Val Asp Arg Thr
1               5

<210> SEQ ID NO 404
<211> LENGTH: 9
<212> TYPE: PRT
<213> ORGANISM: Homo sapiens

<400> SEQUENCE: 404

Asn His Gln Arg Glu Arg Arg Gln Lys
1               5

<210> SEQ ID NO 405
<211> LENGTH: 9
<212> TYPE: PRT
<213> ORGANISM: Homo sapiens

<400> SEQUENCE: 405

Thr Ala Asn Thr Val Asp Arg Thr Asn

```
<210> SEQ ID NO 406
<211> LENGTH: 9
<212> TYPE: PRT
<213> ORGANISM: Homo sapiens

<400> SEQUENCE: 406

His Gln Arg Glu Arg Arg Gln Lys Ser
1               5

<210> SEQ ID NO 407
<211> LENGTH: 9
<212> TYPE: PRT
<213> ORGANISM: Homo sapiens

<400> SEQUENCE: 407

Ala Asn Thr Val Asp Arg Thr Asn His
1               5

<210> SEQ ID NO 408
<211> LENGTH: 9
<212> TYPE: PRT
<213> ORGANISM: Homo sapiens

<400> SEQUENCE: 408

Gln Arg Glu Arg Arg Gln Lys Ser Asp
1               5

<210> SEQ ID NO 409
<211> LENGTH: 9
<212> TYPE: PRT
<213> ORGANISM: Homo sapiens

<400> SEQUENCE: 409

Asn Thr Val Asp Arg Thr Asn His Gln
1               5

<210> SEQ ID NO 410
<211> LENGTH: 9
<212> TYPE: PRT
<213> ORGANISM: Homo sapiens

<400> SEQUENCE: 410

Arg Glu Arg Arg Gln Lys Ser Asp Trp
1               5

<210> SEQ ID NO 411
<211> LENGTH: 9
<212> TYPE: PRT
<213> ORGANISM: Homo sapiens

<400> SEQUENCE: 411

Thr Val Asp Arg Thr Asn His Gln Arg
1               5

<210> SEQ ID NO 412
<211> LENGTH: 9
<212> TYPE: PRT
<213> ORGANISM: Homo sapiens

<400> SEQUENCE: 412

Val Asp Arg Thr Asn His Gln Arg Glu
1               5
```

<210> SEQ ID NO 413
<211> LENGTH: 9
<212> TYPE: PRT
<213> ORGANISM: Homo sapiens

<400> SEQUENCE: 413

Asp Arg Thr Asn His Gln Arg Glu Arg
1               5

<210> SEQ ID NO 414
<211> LENGTH: 9
<212> TYPE: PRT
<213> ORGANISM: Homo sapiens

<400> SEQUENCE: 414

Arg Thr Asn His Gln Arg Glu Arg Arg
1               5

<210> SEQ ID NO 415
<211> LENGTH: 9
<212> TYPE: PRT
<213> ORGANISM: Homo sapiens

<400> SEQUENCE: 415

Thr Asn His Gln Arg Glu Arg Arg Gln
1               5

<210> SEQ ID NO 416
<211> LENGTH: 9
<212> TYPE: PRT
<213> ORGANISM: Homo sapiens

<400> SEQUENCE: 416

Asn His Gln Arg Glu Arg Arg Gln Lys
1               5

<210> SEQ ID NO 417
<211> LENGTH: 9
<212> TYPE: PRT
<213> ORGANISM: Homo sapiens

<400> SEQUENCE: 417

His Gln Arg Glu Arg Arg Gln Lys Ser
1               5

<210> SEQ ID NO 418
<211> LENGTH: 9
<212> TYPE: PRT
<213> ORGANISM: Homo sapiens

<400> SEQUENCE: 418

Gln Arg Glu Arg Arg Gln Lys Ser Asp
1               5

<210> SEQ ID NO 419
<211> LENGTH: 9
<212> TYPE: PRT
<213> ORGANISM: Homo sapiens

<400> SEQUENCE: 419

Arg Glu Arg Arg Gln Lys Ser Asp Trp
1               5

<210> SEQ ID NO 420

```
<211> LENGTH: 10
<212> TYPE: PRT
<213> ORGANISM: Homo sapiens

<400> SEQUENCE: 420

Asp His Pro Ser Thr Ala Asn Thr Val Asp
1               5                   10

<210> SEQ ID NO 421
<211> LENGTH: 10
<212> TYPE: PRT
<213> ORGANISM: Homo sapiens

<400> SEQUENCE: 421

Arg Thr Asn His Gln Arg Glu Arg Arg Gln
1               5                   10

<210> SEQ ID NO 422
<211> LENGTH: 10
<212> TYPE: PRT
<213> ORGANISM: Homo sapiens

<400> SEQUENCE: 422

His Pro Ser Thr Ala Asn Thr Val Asp Arg
1               5                   10

<210> SEQ ID NO 423
<211> LENGTH: 10
<212> TYPE: PRT
<213> ORGANISM: Homo sapiens

<400> SEQUENCE: 423

Thr Asn His Gln Arg Glu Arg Arg Gln Lys
1               5                   10

<210> SEQ ID NO 424
<211> LENGTH: 10
<212> TYPE: PRT
<213> ORGANISM: Homo sapiens

<400> SEQUENCE: 424

Pro Ser Thr Ala Asn Thr Val Asp Arg Thr
1               5                   10

<210> SEQ ID NO 425
<211> LENGTH: 10
<212> TYPE: PRT
<213> ORGANISM: Homo sapiens

<400> SEQUENCE: 425

Asn His Gln Arg Glu Arg Arg Gln Lys Ser
1               5                   10

<210> SEQ ID NO 426
<211> LENGTH: 10
<212> TYPE: PRT
<213> ORGANISM: Homo sapiens

<400> SEQUENCE: 426

Ser Thr Ala Asn Thr Val Asp Arg Thr Asn
1               5                   10

<210> SEQ ID NO 427
<211> LENGTH: 10
<212> TYPE: PRT
```

<213> ORGANISM: Homo sapiens

<400> SEQUENCE: 427

His Gln Arg Glu Arg Arg Gln Lys Ser Asp
1               5                   10

<210> SEQ ID NO 428
<211> LENGTH: 10
<212> TYPE: PRT
<213> ORGANISM: Homo sapiens

<400> SEQUENCE: 428

Thr Ala Asn Thr Val Asp Arg Thr Asn His
1               5                   10

<210> SEQ ID NO 429
<211> LENGTH: 10
<212> TYPE: PRT
<213> ORGANISM: Homo sapiens

<400> SEQUENCE: 429

Gln Arg Glu Arg Arg Gln Lys Ser Asp Trp
1               5                   10

<210> SEQ ID NO 430
<211> LENGTH: 10
<212> TYPE: PRT
<213> ORGANISM: Homo sapiens

<400> SEQUENCE: 430

Ala Asn Thr Val Asp Arg Thr Asn His Gln
1               5                   10

<210> SEQ ID NO 431
<211> LENGTH: 10
<212> TYPE: PRT
<213> ORGANISM: Homo sapiens

<400> SEQUENCE: 431

Asn Thr Val Asp Arg Thr Asn His Gln Arg
1               5                   10

<210> SEQ ID NO 432
<211> LENGTH: 10
<212> TYPE: PRT
<213> ORGANISM: Homo sapiens

<400> SEQUENCE: 432

Thr Val Asp Arg Thr Asn His Gln Arg Glu
1               5                   10

<210> SEQ ID NO 433
<211> LENGTH: 10
<212> TYPE: PRT
<213> ORGANISM: Homo sapiens

<400> SEQUENCE: 433

Val Asp Arg Thr Asn His Gln Arg Glu Arg
1               5                   10

<210> SEQ ID NO 434
<211> LENGTH: 10
<212> TYPE: PRT
<213> ORGANISM: Homo sapiens

<400> SEQUENCE: 434

Asp Arg Thr Asn His Gln Arg Glu Arg Arg
1               5                   10

<210> SEQ ID NO 435
<211> LENGTH: 10
<212> TYPE: PRT
<213> ORGANISM: Homo sapiens

<400> SEQUENCE: 435

Arg Thr Asn His Gln Arg Glu Arg Arg Gln
1               5                   10

<210> SEQ ID NO 436
<211> LENGTH: 10
<212> TYPE: PRT
<213> ORGANISM: Homo sapiens

<400> SEQUENCE: 436

Thr Asn His Gln Arg Glu Arg Arg Gln Lys
1               5                   10

<210> SEQ ID NO 437
<211> LENGTH: 10
<212> TYPE: PRT
<213> ORGANISM: Homo sapiens

<400> SEQUENCE: 437

Asn His Gln Arg Glu Arg Arg Gln Lys Ser
1               5                   10

<210> SEQ ID NO 438
<211> LENGTH: 10
<212> TYPE: PRT
<213> ORGANISM: Homo sapiens

<400> SEQUENCE: 438

His Gln Arg Glu Arg Arg Gln Lys Ser Asp
1               5                   10

<210> SEQ ID NO 439
<211> LENGTH: 10
<212> TYPE: PRT
<213> ORGANISM: Homo sapiens

<400> SEQUENCE: 439

Gln Arg Glu Arg Arg Gln Lys Ser Asp Trp
1               5                   10

<210> SEQ ID NO 440
<211> LENGTH: 11
<212> TYPE: PRT
<213> ORGANISM: Homo sapiens

<400> SEQUENCE: 440

Asp His Pro Ser Thr Ala Asn Thr Val Asp Arg
1               5                   10

<210> SEQ ID NO 441
<211> LENGTH: 11
<212> TYPE: PRT
<213> ORGANISM: Homo sapiens

<400> SEQUENCE: 441

Thr Asn His Gln Arg Glu Arg Arg Gln Lys Ser
1               5                   10

<210> SEQ ID NO 442
<211> LENGTH: 11
<212> TYPE: PRT
<213> ORGANISM: Homo sapiens

<400> SEQUENCE: 442

His Pro Ser Thr Ala Asn Thr Val Asp Arg Thr
1               5                   10

<210> SEQ ID NO 443
<211> LENGTH: 11
<212> TYPE: PRT
<213> ORGANISM: Homo sapiens

<400> SEQUENCE: 443

Asn His Gln Arg Glu Arg Arg Gln Lys Ser Asp
1               5                   10

<210> SEQ ID NO 444
<211> LENGTH: 11
<212> TYPE: PRT
<213> ORGANISM: Homo sapiens

<400> SEQUENCE: 444

Pro Ser Thr Ala Asn Thr Val Asp Arg Thr Asn
1               5                   10

<210> SEQ ID NO 445
<211> LENGTH: 11
<212> TYPE: PRT
<213> ORGANISM: Homo sapiens

<400> SEQUENCE: 445

His Gln Arg Glu Arg Arg Gln Lys Ser Asp Trp
1               5                   10

<210> SEQ ID NO 446
<211> LENGTH: 11
<212> TYPE: PRT
<213> ORGANISM: Homo sapiens

<400> SEQUENCE: 446

Ser Thr Ala Asn Thr Val Asp Arg Thr Asn His
1               5                   10

<210> SEQ ID NO 447
<211> LENGTH: 11
<212> TYPE: PRT
<213> ORGANISM: Homo sapiens

<400> SEQUENCE: 447

Thr Ala Asn Thr Val Asp Arg Thr Asn His Gln
1               5                   10

<210> SEQ ID NO 448
<211> LENGTH: 11
<212> TYPE: PRT
<213> ORGANISM: Homo sapiens

<400> SEQUENCE: 448

Ala Asn Thr Val Asp Arg Thr Asn His Gln Arg
1               5                   10

<210> SEQ ID NO 449
<211> LENGTH: 11
<212> TYPE: PRT
<213> ORGANISM: Homo sapiens

<400> SEQUENCE: 449

Asn Thr Val Asp Arg Thr Asn His Gln Arg Glu
1               5                   10

<210> SEQ ID NO 450
<211> LENGTH: 11
<212> TYPE: PRT
<213> ORGANISM: Homo sapiens

<400> SEQUENCE: 450

Thr Val Asp Arg Thr Asn His Gln Arg Glu Arg
1               5                   10

<210> SEQ ID NO 451
<211> LENGTH: 11
<212> TYPE: PRT
<213> ORGANISM: Homo sapiens

<400> SEQUENCE: 451

Val Asp Arg Thr Asn His Gln Arg Glu Arg Arg
1               5                   10

<210> SEQ ID NO 452
<211> LENGTH: 11
<212> TYPE: PRT
<213> ORGANISM: Homo sapiens

<400> SEQUENCE: 452

Asp Arg Thr Asn His Gln Arg Glu Arg Arg Gln
1               5                   10

<210> SEQ ID NO 453
<211> LENGTH: 11
<212> TYPE: PRT
<213> ORGANISM: Homo sapiens

<400> SEQUENCE: 453

Arg Thr Asn His Gln Arg Glu Arg Arg Gln Lys
1               5                   10

<210> SEQ ID NO 454
<211> LENGTH: 11
<212> TYPE: PRT
<213> ORGANISM: Homo sapiens

<400> SEQUENCE: 454

Thr Asn His Gln Arg Glu Arg Arg Gln Lys Ser
1               5                   10

<210> SEQ ID NO 455
<211> LENGTH: 11
<212> TYPE: PRT
<213> ORGANISM: Homo sapiens

<400> SEQUENCE: 455

Asn His Gln Arg Glu Arg Arg Gln Lys Ser Asp
1               5                   10

<210> SEQ ID NO 456
<211> LENGTH: 11
<212> TYPE: PRT
<213> ORGANISM: Homo sapiens

<400> SEQUENCE: 456

His Gln Arg Glu Arg Arg Gln Lys Ser Asp Trp
1               5                   10

<210> SEQ ID NO 457
<211> LENGTH: 12
<212> TYPE: PRT
<213> ORGANISM: Homo sapiens

<400> SEQUENCE: 457

Asp His Pro Ser Thr Ala Asn Thr Val Asp Arg Thr
1               5                   10

<210> SEQ ID NO 458
<211> LENGTH: 12
<212> TYPE: PRT
<213> ORGANISM: Homo sapiens

<400> SEQUENCE: 458

Asn His Gln Arg Glu Arg Arg Gln Lys Ser Asp Trp
1               5                   10

<210> SEQ ID NO 459
<211> LENGTH: 12
<212> TYPE: PRT
<213> ORGANISM: Homo sapiens

<400> SEQUENCE: 459

His Pro Ser Thr Ala Asn Thr Val Asp Arg Thr Asn
1               5                   10

<210> SEQ ID NO 460
<211> LENGTH: 12
<212> TYPE: PRT
<213> ORGANISM: Homo sapiens

<400> SEQUENCE: 460

Pro Ser Thr Ala Asn Thr Val Asp Arg Thr Asn His
1               5                   10

<210> SEQ ID NO 461
<211> LENGTH: 12
<212> TYPE: PRT
<213> ORGANISM: Homo sapiens

<400> SEQUENCE: 461

Ser Thr Ala Asn Thr Val Asp Arg Thr Asn His Gln
1               5                   10

<210> SEQ ID NO 462
<211> LENGTH: 12
<212> TYPE: PRT
<213> ORGANISM: Homo sapiens

<400> SEQUENCE: 462

Thr Ala Asn Thr Val Asp Arg Thr Asn His Gln Arg
1               5                   10

<210> SEQ ID NO 463
<211> LENGTH: 12

```
<212> TYPE: PRT
<213> ORGANISM: Homo sapiens

<400> SEQUENCE: 463

Ala Asn Thr Val Asp Arg Thr Asn His Gln Arg Glu
1               5                   10

<210> SEQ ID NO 464
<211> LENGTH: 12
<212> TYPE: PRT
<213> ORGANISM: Homo sapiens

<400> SEQUENCE: 464

Asn Thr Val Asp Arg Thr Asn His Gln Arg Glu Arg
1               5                   10

<210> SEQ ID NO 465
<211> LENGTH: 12
<212> TYPE: PRT
<213> ORGANISM: Homo sapiens

<400> SEQUENCE: 465

Thr Val Asp Arg Thr Asn His Gln Arg Glu Arg Arg
1               5                   10

<210> SEQ ID NO 466
<211> LENGTH: 12
<212> TYPE: PRT
<213> ORGANISM: Homo sapiens

<400> SEQUENCE: 466

Val Asp Arg Thr Asn His Gln Arg Glu Arg Arg Gln
1               5                   10

<210> SEQ ID NO 467
<211> LENGTH: 12
<212> TYPE: PRT
<213> ORGANISM: Homo sapiens

<400> SEQUENCE: 467

Asp Arg Thr Asn His Gln Arg Glu Arg Arg Gln Lys
1               5                   10

<210> SEQ ID NO 468
<211> LENGTH: 12
<212> TYPE: PRT
<213> ORGANISM: Homo sapiens

<400> SEQUENCE: 468

Arg Thr Asn His Gln Arg Glu Arg Arg Gln Lys Ser
1               5                   10

<210> SEQ ID NO 469
<211> LENGTH: 12
<212> TYPE: PRT
<213> ORGANISM: Homo sapiens

<400> SEQUENCE: 469

Thr Asn His Gln Arg Glu Arg Arg Gln Lys Ser Asp
1               5                   10

<210> SEQ ID NO 470
<211> LENGTH: 12
<212> TYPE: PRT
<213> ORGANISM: Homo sapiens
```

<400> SEQUENCE: 470

Asn His Gln Arg Glu Arg Arg Gln Lys Ser Asp Trp
1               5                   10

<210> SEQ ID NO 471
<211> LENGTH: 13
<212> TYPE: PRT
<213> ORGANISM: Homo sapiens

<400> SEQUENCE: 471

Asp His Pro Ser Thr Ala Asn Thr Val Asp Arg Thr Asn
1               5                   10

<210> SEQ ID NO 472
<211> LENGTH: 13
<212> TYPE: PRT
<213> ORGANISM: Homo sapiens

<400> SEQUENCE: 472

His Pro Ser Thr Ala Asn Thr Val Asp Arg Thr Asn His
1               5                   10

<210> SEQ ID NO 473
<211> LENGTH: 13
<212> TYPE: PRT
<213> ORGANISM: Homo sapiens

<400> SEQUENCE: 473

Pro Ser Thr Ala Asn Thr Val Asp Arg Thr Asn His Gln
1               5                   10

<210> SEQ ID NO 474
<211> LENGTH: 13
<212> TYPE: PRT
<213> ORGANISM: Homo sapiens

<400> SEQUENCE: 474

Ser Thr Ala Asn Thr Val Asp Arg Thr Asn His Gln Arg
1               5                   10

<210> SEQ ID NO 475
<211> LENGTH: 13
<212> TYPE: PRT
<213> ORGANISM: Homo sapiens

<400> SEQUENCE: 475

Thr Ala Asn Thr Val Asp Arg Thr Asn His Gln Arg Glu
1               5                   10

<210> SEQ ID NO 476
<211> LENGTH: 13
<212> TYPE: PRT
<213> ORGANISM: Homo sapiens

<400> SEQUENCE: 476

Ala Asn Thr Val Asp Arg Thr Asn His Gln Arg Glu Arg
1               5                   10

<210> SEQ ID NO 477
<211> LENGTH: 13
<212> TYPE: PRT
<213> ORGANISM: Homo sapiens

<400> SEQUENCE: 477

Asn Thr Val Asp Arg Thr Asn His Gln Arg Glu Arg Arg
1               5                   10

<210> SEQ ID NO 478
<211> LENGTH: 13
<212> TYPE: PRT
<213> ORGANISM: Homo sapiens

<400> SEQUENCE: 478

Thr Val Asp Arg Thr Asn His Gln Arg Glu Arg Arg Gln
1               5                   10

<210> SEQ ID NO 479
<211> LENGTH: 13
<212> TYPE: PRT
<213> ORGANISM: Homo sapiens

<400> SEQUENCE: 479

Val Asp Arg Thr Asn His Gln Arg Glu Arg Arg Gln Lys
1               5                   10

<210> SEQ ID NO 480
<211> LENGTH: 13
<212> TYPE: PRT
<213> ORGANISM: Homo sapiens

<400> SEQUENCE: 480

Asp Arg Thr Asn His Gln Arg Glu Arg Arg Gln Lys Ser
1               5                   10

<210> SEQ ID NO 481
<211> LENGTH: 13
<212> TYPE: PRT
<213> ORGANISM: Homo sapiens

<400> SEQUENCE: 481

Arg Thr Asn His Gln Arg Glu Arg Arg Gln Lys Ser Asp
1               5                   10

<210> SEQ ID NO 482
<211> LENGTH: 13
<212> TYPE: PRT
<213> ORGANISM: Homo sapiens

<400> SEQUENCE: 482

Thr Asn His Gln Arg Glu Arg Arg Gln Lys Ser Asp Trp
1               5                   10

<210> SEQ ID NO 483
<211> LENGTH: 14
<212> TYPE: PRT
<213> ORGANISM: Homo sapiens

<400> SEQUENCE: 483

Asp His Pro Ser Thr Ala Asn Thr Val Asp Arg Thr Asn His
1               5                   10

<210> SEQ ID NO 484
<211> LENGTH: 14
<212> TYPE: PRT
<213> ORGANISM: Homo sapiens

<400> SEQUENCE: 484

His Pro Ser Thr Ala Asn Thr Val Asp Arg Thr Asn His Gln

```
1               5               10
```

<210> SEQ ID NO 485
<211> LENGTH: 14
<212> TYPE: PRT
<213> ORGANISM: Homo sapiens

<400> SEQUENCE: 485

```
Pro Ser Thr Ala Asn Thr Val Asp Arg Thr Asn His Gln Arg
1               5                   10
```

<210> SEQ ID NO 486
<211> LENGTH: 14
<212> TYPE: PRT
<213> ORGANISM: Homo sapiens

<400> SEQUENCE: 486

```
Ser Thr Ala Asn Thr Val Asp Arg Thr Asn His Gln Arg Glu
1               5                   10
```

<210> SEQ ID NO 487
<211> LENGTH: 14
<212> TYPE: PRT
<213> ORGANISM: Homo sapiens

<400> SEQUENCE: 487

```
Thr Ala Asn Thr Val Asp Arg Thr Asn His Gln Arg Glu Arg
1               5                   10
```

<210> SEQ ID NO 488
<211> LENGTH: 14
<212> TYPE: PRT
<213> ORGANISM: Homo sapiens

<400> SEQUENCE: 488

```
Ala Asn Thr Val Asp Arg Thr Asn His Gln Arg Glu Arg Arg
1               5                   10
```

<210> SEQ ID NO 489
<211> LENGTH: 14
<212> TYPE: PRT
<213> ORGANISM: Homo sapiens

<400> SEQUENCE: 489

```
Asn Thr Val Asp Arg Thr Asn His Gln Arg Glu Arg Arg Gln
1               5                   10
```

<210> SEQ ID NO 490
<211> LENGTH: 14
<212> TYPE: PRT
<213> ORGANISM: Homo sapiens

<400> SEQUENCE: 490

```
Thr Val Asp Arg Thr Asn His Gln Arg Glu Arg Arg Gln Lys
1               5                   10
```

<210> SEQ ID NO 491
<211> LENGTH: 14
<212> TYPE: PRT
<213> ORGANISM: Homo sapiens

<400> SEQUENCE: 491

```
Val Asp Arg Thr Asn His Gln Arg Glu Arg Arg Gln Lys Ser
1               5                   10
```

<210> SEQ ID NO 492
<211> LENGTH: 14
<212> TYPE: PRT
<213> ORGANISM: Homo sapiens

<400> SEQUENCE: 492

Asp Arg Thr Asn His Gln Arg Glu Arg Arg Gln Lys Ser Asp
1               5                   10

<210> SEQ ID NO 493
<211> LENGTH: 14
<212> TYPE: PRT
<213> ORGANISM: Homo sapiens

<400> SEQUENCE: 493

Arg Thr Asn His Gln Arg Glu Arg Arg Gln Lys Ser Asp Trp
1               5                   10

<210> SEQ ID NO 494
<211> LENGTH: 15
<212> TYPE: PRT
<213> ORGANISM: Homo sapiens

<400> SEQUENCE: 494

Asp His Pro Ser Thr Ala Asn Thr Val Asp Arg Thr Asn His Gln
1               5                   10                  15

<210> SEQ ID NO 495
<211> LENGTH: 15
<212> TYPE: PRT
<213> ORGANISM: Homo sapiens

<400> SEQUENCE: 495

His Pro Ser Thr Ala Asn Thr Val Asp Arg Thr Asn His Gln Arg
1               5                   10                  15

<210> SEQ ID NO 496
<211> LENGTH: 15
<212> TYPE: PRT
<213> ORGANISM: Homo sapiens

<400> SEQUENCE: 496

Pro Ser Thr Ala Asn Thr Val Asp Arg Thr Asn His Gln Arg Glu
1               5                   10                  15

<210> SEQ ID NO 497
<211> LENGTH: 15
<212> TYPE: PRT
<213> ORGANISM: Homo sapiens

<400> SEQUENCE: 497

Ser Thr Ala Asn Thr Val Asp Arg Thr Asn His Gln Arg Glu Arg
1               5                   10                  15

<210> SEQ ID NO 498
<211> LENGTH: 15
<212> TYPE: PRT
<213> ORGANISM: Homo sapiens

<400> SEQUENCE: 498

Thr Ala Asn Thr Val Asp Arg Thr Asn His Gln Arg Glu Arg Arg
1               5                   10                  15

<210> SEQ ID NO 499

```
<211> LENGTH: 15
<212> TYPE: PRT
<213> ORGANISM: Homo sapiens

<400> SEQUENCE: 499

Ala Asn Thr Val Asp Arg Thr Asn His Gln Arg Glu Arg Arg Gln
1               5                   10                  15

<210> SEQ ID NO 500
<211> LENGTH: 15
<212> TYPE: PRT
<213> ORGANISM: Homo sapiens

<400> SEQUENCE: 500

Asn Thr Val Asp Arg Thr Asn His Gln Arg Glu Arg Arg Gln Lys
1               5                   10                  15

<210> SEQ ID NO 501
<211> LENGTH: 15
<212> TYPE: PRT
<213> ORGANISM: Homo sapiens

<400> SEQUENCE: 501

Thr Val Asp Arg Thr Asn His Gln Arg Glu Arg Arg Gln Lys Ser
1               5                   10                  15

<210> SEQ ID NO 502
<211> LENGTH: 15
<212> TYPE: PRT
<213> ORGANISM: Homo sapiens

<400> SEQUENCE: 502

Val Asp Arg Thr Asn His Gln Arg Glu Arg Arg Gln Lys Ser Asp
1               5                   10                  15

<210> SEQ ID NO 503
<211> LENGTH: 15
<212> TYPE: PRT
<213> ORGANISM: Homo sapiens

<400> SEQUENCE: 503

Asp Arg Thr Asn His Gln Arg Glu Arg Arg Gln Lys Ser Asp Trp
1               5                   10                  15

<210> SEQ ID NO 504
<211> LENGTH: 16
<212> TYPE: PRT
<213> ORGANISM: Homo sapiens

<400> SEQUENCE: 504

Asp His Pro Ser Thr Ala Asn Thr Val Asp Arg Thr Asn His Gln Arg
1               5                   10                  15

<210> SEQ ID NO 505
<211> LENGTH: 16
<212> TYPE: PRT
<213> ORGANISM: Homo sapiens

<400> SEQUENCE: 505

His Pro Ser Thr Ala Asn Thr Val Asp Arg Thr Asn His Gln Arg Glu
1               5                   10                  15

<210> SEQ ID NO 506
<211> LENGTH: 16
<212> TYPE: PRT
```

<213> ORGANISM: Homo sapiens

<400> SEQUENCE: 506

Pro Ser Thr Ala Asn Thr Val Asp Arg Thr Asn His Gln Arg Glu Arg
1               5                   10                  15

<210> SEQ ID NO 507
<211> LENGTH: 16
<212> TYPE: PRT
<213> ORGANISM: Homo sapiens

<400> SEQUENCE: 507

Ser Thr Ala Asn Thr Val Asp Arg Thr Asn His Gln Arg Glu Arg Arg
1               5                   10                  15

<210> SEQ ID NO 508
<211> LENGTH: 16
<212> TYPE: PRT
<213> ORGANISM: Homo sapiens

<400> SEQUENCE: 508

Thr Ala Asn Thr Val Asp Arg Thr Asn His Gln Arg Glu Arg Arg Gln
1               5                   10                  15

<210> SEQ ID NO 509
<211> LENGTH: 16
<212> TYPE: PRT
<213> ORGANISM: Homo sapiens

<400> SEQUENCE: 509

Ala Asn Thr Val Asp Arg Thr Asn His Gln Arg Glu Arg Arg Gln Lys
1               5                   10                  15

<210> SEQ ID NO 510
<211> LENGTH: 16
<212> TYPE: PRT
<213> ORGANISM: Homo sapiens

<400> SEQUENCE: 510

Asn Thr Val Asp Arg Thr Asn His Gln Arg Glu Arg Arg Gln Lys Ser
1               5                   10                  15

<210> SEQ ID NO 511
<211> LENGTH: 16
<212> TYPE: PRT
<213> ORGANISM: Homo sapiens

<400> SEQUENCE: 511

Thr Val Asp Arg Thr Asn His Gln Arg Glu Arg Arg Gln Lys Ser Asp
1               5                   10                  15

<210> SEQ ID NO 512
<211> LENGTH: 16
<212> TYPE: PRT
<213> ORGANISM: Homo sapiens

<400> SEQUENCE: 512

Val Asp Arg Thr Asn His Gln Arg Glu Arg Arg Gln Lys Ser Asp Trp
1               5                   10                  15

<210> SEQ ID NO 513
<211> LENGTH: 17
<212> TYPE: PRT
<213> ORGANISM: Homo sapiens

```
<400> SEQUENCE: 513

Asp His Pro Ser Thr Ala Asn Thr Val Asp Arg Thr Asn His Gln Arg
1               5                   10                  15
Glu

<210> SEQ ID NO 514
<211> LENGTH: 17
<212> TYPE: PRT
<213> ORGANISM: Homo sapiens

<400> SEQUENCE: 514

His Pro Ser Thr Ala Asn Thr Val Asp Arg Thr Asn His Gln Arg Glu
1               5                   10                  15
Arg

<210> SEQ ID NO 515
<211> LENGTH: 17
<212> TYPE: PRT
<213> ORGANISM: Homo sapiens

<400> SEQUENCE: 515

Pro Ser Thr Ala Asn Thr Val Asp Arg Thr Asn His Gln Arg Glu Arg
1               5                   10                  15
Arg

<210> SEQ ID NO 516
<211> LENGTH: 17
<212> TYPE: PRT
<213> ORGANISM: Homo sapiens

<400> SEQUENCE: 516

Ser Thr Ala Asn Thr Val Asp Arg Thr Asn His Gln Arg Glu Arg Arg
1               5                   10                  15
Gln

<210> SEQ ID NO 517
<211> LENGTH: 17
<212> TYPE: PRT
<213> ORGANISM: Homo sapiens

<400> SEQUENCE: 517

Thr Ala Asn Thr Val Asp Arg Thr Asn His Gln Arg Glu Arg Arg Gln
1               5                   10                  15
Lys

<210> SEQ ID NO 518
<211> LENGTH: 17
<212> TYPE: PRT
<213> ORGANISM: Homo sapiens

<400> SEQUENCE: 518

Ala Asn Thr Val Asp Arg Thr Asn His Gln Arg Glu Arg Arg Gln Lys
1               5                   10                  15
Ser

<210> SEQ ID NO 519
<211> LENGTH: 17
<212> TYPE: PRT
<213> ORGANISM: Homo sapiens

<400> SEQUENCE: 519
```

```
Asn Thr Val Asp Arg Thr Asn His Gln Arg Glu Arg Gln Lys Ser
1               5                   10                  15
Asp

<210> SEQ ID NO 520
<211> LENGTH: 17
<212> TYPE: PRT
<213> ORGANISM: Homo sapiens

<400> SEQUENCE: 520

Thr Val Asp Arg Thr Asn His Gln Arg Glu Arg Arg Gln Lys Ser Asp
1               5                   10                  15
Trp

<210> SEQ ID NO 521
<211> LENGTH: 18
<212> TYPE: PRT
<213> ORGANISM: Homo sapiens

<400> SEQUENCE: 521

Asp His Pro Ser Thr Ala Asn Thr Val Asp Arg Thr Asn His Gln Arg
1               5                   10                  15
Glu Arg

<210> SEQ ID NO 522
<211> LENGTH: 18
<212> TYPE: PRT
<213> ORGANISM: Homo sapiens

<400> SEQUENCE: 522

His Pro Ser Thr Ala Asn Thr Val Asp Arg Thr Asn His Gln Arg Glu
1               5                   10                  15
Arg Arg

<210> SEQ ID NO 523
<211> LENGTH: 18
<212> TYPE: PRT
<213> ORGANISM: Homo sapiens

<400> SEQUENCE: 523

Pro Ser Thr Ala Asn Thr Val Asp Arg Thr Asn His Gln Arg Glu Arg
1               5                   10                  15
Arg Gln

<210> SEQ ID NO 524
<211> LENGTH: 18
<212> TYPE: PRT
<213> ORGANISM: Homo sapiens

<400> SEQUENCE: 524

Ser Thr Ala Asn Thr Val Asp Arg Thr Asn His Gln Arg Glu Arg Arg
1               5                   10                  15
Gln Lys

<210> SEQ ID NO 525
<211> LENGTH: 18
<212> TYPE: PRT
<213> ORGANISM: Homo sapiens

<400> SEQUENCE: 525
```

Thr Ala Asn Thr Val Asp Arg Thr Asn His Gln Arg Glu Arg Gln
1               5                   10                  15

Lys Ser

<210> SEQ ID NO 526
<211> LENGTH: 18
<212> TYPE: PRT
<213> ORGANISM: Homo sapiens

<400> SEQUENCE: 526

Ala Asn Thr Val Asp Arg Thr Asn His Gln Arg Glu Arg Gln Lys
1               5                   10                  15

Ser Asp

<210> SEQ ID NO 527
<211> LENGTH: 18
<212> TYPE: PRT
<213> ORGANISM: Homo sapiens

<400> SEQUENCE: 527

Asn Thr Val Asp Arg Thr Asn His Gln Arg Glu Arg Gln Lys Ser
1               5                   10                  15

Asp Trp

<210> SEQ ID NO 528
<211> LENGTH: 19
<212> TYPE: PRT
<213> ORGANISM: Homo sapiens

<400> SEQUENCE: 528

Asp His Pro Ser Thr Ala Asn Thr Val Asp Arg Thr Asn His Gln Arg
1               5                   10                  15

Glu Arg Arg

<210> SEQ ID NO 529
<211> LENGTH: 19
<212> TYPE: PRT
<213> ORGANISM: Homo sapiens

<400> SEQUENCE: 529

His Pro Ser Thr Ala Asn Thr Val Asp Arg Thr Asn His Gln Arg Glu
1               5                   10                  15

Arg Arg Gln

<210> SEQ ID NO 530
<211> LENGTH: 19
<212> TYPE: PRT
<213> ORGANISM: Homo sapiens

<400> SEQUENCE: 530

Pro Ser Thr Ala Asn Thr Val Asp Arg Thr Asn His Gln Arg Glu Arg
1               5                   10                  15

Arg Gln Lys

<210> SEQ ID NO 531
<211> LENGTH: 19
<212> TYPE: PRT
<213> ORGANISM: Homo sapiens

<400> SEQUENCE: 531

Ser Thr Ala Asn Thr Val Asp Arg Thr Asn His Gln Arg Glu Arg Arg

```
1               5                   10                  15

Gln Lys Ser

<210> SEQ ID NO 532
<211> LENGTH: 19
<212> TYPE: PRT
<213> ORGANISM: Homo sapiens

<400> SEQUENCE: 532

Thr Ala Asn Thr Val Asp Arg Thr Asn His Gln Arg Glu Arg Arg Gln
1               5                   10                  15

Lys Ser Asp

<210> SEQ ID NO 533
<211> LENGTH: 19
<212> TYPE: PRT
<213> ORGANISM: Homo sapiens

<400> SEQUENCE: 533

Ala Asn Thr Val Asp Arg Thr Asn His Gln Arg Glu Arg Arg Gln Lys
1               5                   10                  15

Ser Asp Trp

<210> SEQ ID NO 534
<211> LENGTH: 20
<212> TYPE: PRT
<213> ORGANISM: Homo sapiens

<400> SEQUENCE: 534

Asp His Pro Ser Thr Ala Asn Thr Val Asp Arg Thr Asn His Gln Arg
1               5                   10                  15

Glu Arg Arg Gln
            20

<210> SEQ ID NO 535
<211> LENGTH: 20
<212> TYPE: PRT
<213> ORGANISM: Homo sapiens

<400> SEQUENCE: 535

His Pro Ser Thr Ala Asn Thr Val Asp Arg Thr Asn His Gln Arg Glu
1               5                   10                  15

Arg Arg Gln Lys
            20

<210> SEQ ID NO 536
<211> LENGTH: 20
<212> TYPE: PRT
<213> ORGANISM: Homo sapiens

<400> SEQUENCE: 536

Pro Ser Thr Ala Asn Thr Val Asp Arg Thr Asn His Gln Arg Glu Arg
1               5                   10                  15

Arg Gln Lys Ser
            20

<210> SEQ ID NO 537
<211> LENGTH: 20
<212> TYPE: PRT
<213> ORGANISM: Homo sapiens

<400> SEQUENCE: 537
```

Ser Thr Ala Asn Thr Val Asp Arg Thr Asn His Gln Arg Glu Arg Arg
1               5                   10                  15

Gln Lys Ser Asp
            20

<210> SEQ ID NO 538
<211> LENGTH: 20
<212> TYPE: PRT
<213> ORGANISM: Homo sapiens

<400> SEQUENCE: 538

Thr Ala Asn Thr Val Asp Arg Thr Asn His Gln Arg Glu Arg Arg Gln
1               5                   10                  15

Lys Ser Asp Trp
            20

<210> SEQ ID NO 539
<211> LENGTH: 21
<212> TYPE: PRT
<213> ORGANISM: Homo sapiens

<400> SEQUENCE: 539

Asp His Pro Ser Thr Ala Asn Thr Val Asp Arg Thr Asn His Gln Arg
1               5                   10                  15

Glu Arg Arg Gln Lys
            20

<210> SEQ ID NO 540
<211> LENGTH: 21
<212> TYPE: PRT
<213> ORGANISM: Homo sapiens

<400> SEQUENCE: 540

His Pro Ser Thr Ala Asn Thr Val Asp Arg Thr Asn His Gln Arg Glu
1               5                   10                  15

Arg Arg Gln Lys Ser
            20

<210> SEQ ID NO 541
<211> LENGTH: 21
<212> TYPE: PRT
<213> ORGANISM: Homo sapiens

<400> SEQUENCE: 541

Pro Ser Thr Ala Asn Thr Val Asp Arg Thr Asn His Gln Arg Glu Arg
1               5                   10                  15

Arg Gln Lys Ser Asp
            20

<210> SEQ ID NO 542
<211> LENGTH: 21
<212> TYPE: PRT
<213> ORGANISM: Homo sapiens

<400> SEQUENCE: 542

Ser Thr Ala Asn Thr Val Asp Arg Thr Asn His Gln Arg Glu Arg Arg
1               5                   10                  15

Gln Lys Ser Asp Trp
            20

<210> SEQ ID NO 543

```
<211> LENGTH: 22
<212> TYPE: PRT
<213> ORGANISM: Homo sapiens

<400> SEQUENCE: 543

Asp His Pro Ser Thr Ala Asn Thr Val Asp Arg Thr Asn His Gln Arg
1               5                   10                  15

Glu Arg Arg Gln Lys Ser
            20

<210> SEQ ID NO 544
<211> LENGTH: 22
<212> TYPE: PRT
<213> ORGANISM: Homo sapiens

<400> SEQUENCE: 544

His Pro Ser Thr Ala Asn Thr Val Asp Arg Thr Asn His Gln Arg Glu
1               5                   10                  15

Arg Arg Gln Lys Ser Asp
            20

<210> SEQ ID NO 545
<211> LENGTH: 22
<212> TYPE: PRT
<213> ORGANISM: Homo sapiens

<400> SEQUENCE: 545

Pro Ser Thr Ala Asn Thr Val Asp Arg Thr Asn His Gln Arg Glu Arg
1               5                   10                  15

Arg Gln Lys Ser Asp Trp
            20

<210> SEQ ID NO 546
<211> LENGTH: 23
<212> TYPE: PRT
<213> ORGANISM: Homo sapiens

<400> SEQUENCE: 546

Asp His Pro Ser Thr Ala Asn Thr Val Asp Arg Thr Asn His Gln Arg
1               5                   10                  15

Glu Arg Arg Gln Lys Ser Asp
            20

<210> SEQ ID NO 547
<211> LENGTH: 23
<212> TYPE: PRT
<213> ORGANISM: Homo sapiens

<400> SEQUENCE: 547

His Pro Ser Thr Ala Asn Thr Val Asp Arg Thr Asn His Gln Arg Glu
1               5                   10                  15

Arg Arg Gln Lys Ser Asp Trp
            20

<210> SEQ ID NO 548
<211> LENGTH: 24
<212> TYPE: PRT
<213> ORGANISM: Homo sapiens

<400> SEQUENCE: 548

Asp His Pro Ser Thr Ala Asn Thr Val Asp Arg Thr Asn His Gln Arg
1               5                   10                  15
```

Glu Arg Arg Gln Lys Ser Asp Trp
            20

<210> SEQ ID NO 549
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 549

Arg Gln Ile Lys Trp Phe Gln Asn Arg Arg Met Lys Trp Lys Lys
1               5                   10                  15

<210> SEQ ID NO 550
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 550

Tyr Gly Arg Lys Lys Arg Arg Gln Arg Arg Arg
1               5                   10

<210> SEQ ID NO 551
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 551

Arg Gly Gly Arg Leu Ser Tyr Ser Arg Arg Phe Ser Thr Ser Thr
1               5                   10                  15

Gly Arg

<210> SEQ ID NO 552
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 552

Arg Arg Leu Ser Tyr Ser Arg Arg Arg Phe
1               5                   10

<210> SEQ ID NO 553
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 553

Pro Ile Arg Arg Arg Lys Lys Leu Arg Arg Leu Lys
1               5                   10

<210> SEQ ID NO 554
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 554

```
Arg Arg Gln Arg Arg Thr Ser Lys Leu Met Lys Arg
1               5                   10
```

<210> SEQ ID NO 555
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 555

```
Arg Arg Arg Arg Asn Arg Thr Arg Arg Asn Arg Arg Arg Val Arg
1               5                   10                  15
```

<210> SEQ ID NO 556
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 556

```
Lys Met Thr Arg Ala Gln Arg Arg Ala Ala Ala Arg Arg Asn Arg Trp
1               5                   10                  15

Thr Ala Arg
```

<210> SEQ ID NO 557
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 557

```
Thr Arg Arg Gln Arg Thr Arg Arg Ala Arg Arg Asn Arg
1               5                   10
```

<210> SEQ ID NO 558
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 558

```
Gly Arg Lys Lys Arg Arg Gln Arg Arg Arg Pro Pro Gln
1               5                   10
```

<210> SEQ ID NO 559
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 559

```
Gly Arg Arg Arg Arg Arg Arg Arg Arg Arg Pro Pro Gln
1               5                   10
```

<210> SEQ ID NO 560
<211> LENGTH: 27
<212> TYPE: PRT
<213> ORGANISM: Artificial Sequence
<220> FEATURE:
<223> OTHER INFORMATION: SYNTHESIZED

```
<400> SEQUENCE: 560

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 561
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 561

Lys Leu Ala Leu Lys Leu Ala Leu Lys Leu Ala Leu Ala Leu Lys Leu
1               5                   10                  15

Ala

<210> SEQ ID NO 562
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 562

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 563
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 563

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 564
<211> LENGTH: 32
<212> TYPE: PRT
<213> ORGANISM: Artificial Sequence
<220> FEATURE:
<223> OTHER INFORMATION: SYNTHESIZED

<400> SEQUENCE: 564

Ala Cys Gly Ala Leu Phe Leu Gly Phe Leu Gly Ala Ala Gly Ser Thr
1               5                   10                  15

Met Gly Ala Trp Ser Gln Pro Lys Lys Lys Arg Lys Val Cys Tyr Ala
            20                  25                  30

<210> SEQ ID NO 565
<211> LENGTH: 32
<212> TYPE: PRT
<213> ORGANISM: Artificial Sequence
<220> FEATURE:
<223> OTHER INFORMATION: SYNTHESIZED
```

```
<400> SEQUENCE: 565

Ala Cys Gly Ala Leu Phe Leu Gly Phe Leu Gly Ala Ala Gly Ser Thr
1               5                   10                  15

Met Gly Ala Trp Ser Gln Pro Lys Ser Lys Arg Lys Val Cys Tyr Ala
            20                  25                  30

<210> SEQ ID NO 566
<211> LENGTH: 26
<212> TYPE: PRT
<213> ORGANISM: Artificial Sequence
<220> FEATURE:
<223> OTHER INFORMATION: SYNTHESIZED

<400> SEQUENCE: 566

Ala Cys Lys Glu Thr Trp Trp Glu Thr Trp Trp Thr Glu Trp Ser Gln
1               5                   10                  15

Pro Lys Lys Lys Arg Lys Val Cys Tyr Ala
            20                  25

<210> SEQ ID NO 567
<211> LENGTH: 26
<212> TYPE: PRT
<213> ORGANISM: Artificial Sequence
<220> FEATURE:
<223> OTHER INFORMATION: SYNTHESIZED

<400> SEQUENCE: 567

Ala Cys Lys Glu Thr Trp Phe Glu Thr Trp Phe Thr Glu Trp Ser Gln
1               5                   10                  15

Pro Lys Lys Lys Arg Lys Val Cys Tyr Ala
            20                  25

<210> SEQ ID NO 568
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 568

Tyr Gly Arg Lys Lys Arg Arg Gln Arg Arg Arg Asn Glu Glu Pro
1               5                   10                  15

Ser Ser

<210> SEQ ID NO 569
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 569

Tyr Gly Arg Lys Lys Arg Arg Gln Arg Arg Ser Glu Pro Asn Ser
1               5                   10                  15

Glu Arg

<210> SEQ ID NO 570
<211> LENGTH: 21
<212> TYPE: RNA
<213> ORGANISM: Artificial Sequence
<220> FEATURE:
<223> OTHER INFORMATION: SYNTHESIZED

<400> SEQUENCE: 570
```
ucuggaagca gaaacugcuu u    21

<210> SEQ ID NO 571
<211> LENGTH: 21
<212> TYPE: RNA
<213> ORGANISM: Artificial Sequence
<220> FEATURE:
<223> OTHER INFORMATION: SYNTHESIZED

<400> SEQUENCE: 571
aaacccugca agaguugcau u    21

<210> SEQ ID NO 572
<211> LENGTH: 21
<212> TYPE: RNA
<213> ORGANISM: Artificial Sequence
<220> FEATURE:
<223> OTHER INFORMATION: SYNTHESIZED

<400> SEQUENCE: 572
ugaggaaccu ucuuccugau u    21

<210> SEQ ID NO 573
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 573
gaggaaggca tttacaacca ag    22

<210> SEQ ID NO 574
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 574
actgctcttg ccgaagatta ag    22

<210> SEQ ID NO 575
<211> LENGTH: 18
<212> TYPE: DNA
<213> ORGANISM: Artificial Sequence
<220> FEATURE:
<223> OTHER INFORMATION: SYNTHESIZED

<400> SEQUENCE: 575
ctgatgggcc gtatcctg    18

<210> SEQ ID NO 576
<211> LENGTH: 18
<212> TYPE: DNA
<213> ORGANISM: Artificial Sequence
<220> FEATURE:
<223> OTHER INFORMATION: SYNTHESIZED

<400> SEQUENCE: 576
aggaactgcc ccgaaatc    18

<210> SEQ ID NO 577
<211> LENGTH: 19
<212> TYPE: DNA

```
<213> ORGANISM: Artificial Sequence
<220> FEATURE:
<223> OTHER INFORMATION: SYNTHESIZED

<400> SEQUENCE: 577
gggcgcagaa caacgagat                                          19

<210> SEQ ID NO 578
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 578
gaagttttgc aggtcacggt t                                       21

<210> SEQ ID NO 579
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 579
gttcaccagc atcttcacg                                          19

<210> SEQ ID NO 580
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 580
tgcataccac tgctccatc                                          19

<210> SEQ ID NO 581
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 581

Ala Cys Cys Cys Ala Gly Thr Thr Cys Thr Thr Thr Ala Thr Gly Cys
 1               5                  10                  15

Gly Thr Thr Cys
            20

<210> SEQ ID NO 582
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 582
tcaggaagaa ggttcctcat tc                                      22

<210> SEQ ID NO 583
<211> LENGTH: 21
<212> TYPE: DNA
<213> ORGANISM: Artificial Sequence
<220> FEATURE:
<223> OTHER INFORMATION: SYNTHESIZED
```

```
<400> SEQUENCE: 583
agcaagagct tcaggaagca g                                    21

<210> SEQ ID NO 584
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 584
ctagacatac ccctcatgac ag                                   22

<210> SEQ ID NO 585
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 585
aaacggctac cacatccaag                                      20

<210> SEQ ID NO 586
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 586
cctccaatgg atcctcgtta                                      20

<210> SEQ ID NO 587
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 587

Glu Gln Lys Leu Ile Ser Glu Glu Asp Leu
1               5                   10

<210> SEQ ID NO 588
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 588

Tyr Pro Tyr Asp Val Pro Asp Tyr Ala
1               5

<210> SEQ ID NO 589
<211> LENGTH: 397
<212> TYPE: PRT
<213> ORGANISM: Artificial Sequence
<220> FEATURE:
<223> OTHER INFORMATION: SYNTHESIZED

<400> SEQUENCE: 589

Met Asp Ser Ser Ala Ala Pro Thr Asn Ala Ser Asn Cys Thr Asp Ala
1               5                   10                  15
```

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45

Arg Thr Asp Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

Arg Gln Asn Thr Arg Asp His Pro Ser Thr Ala Asn Thr Val Asp Arg
    370                 375                 380

Thr Asn His Gln Arg Glu Arg Gln Lys Ser Asp Trp
385                 390                 395

<210> SEQ ID NO 590
<211> LENGTH: 65
<212> TYPE: PRT
<213> ORGANISM: Mus musculus

```
<400> SEQUENCE: 590

Ser Cys Leu Asn Pro Val Leu Tyr Ala Phe Leu Asp Glu Asn Phe Lys
1               5                   10                  15

Arg Cys Phe Arg Glu Phe Cys Ile Pro Thr Ser Ser Thr Ile Glu Gln
                20                  25                  30

Gln Asn Ser Ala Arg Ile Arg Gln Asn Thr Arg Glu His Pro Ser Thr
            35                  40                  45

Ala Asn Thr Val Asp Arg Thr Asn His Gln Arg Asn Glu Glu Pro Ser
        50                  55                  60

Ser
65

<210> SEQ ID NO 591
<211> LENGTH: 70
<212> TYPE: PRT
<213> ORGANISM: Mus musculus

<400> SEQUENCE: 591

Ser Cys Leu Asn Pro Val Leu Tyr Ala Phe Leu Asp Glu Asn Phe Lys
1               5                   10                  15

Arg Cys Phe Arg Glu Phe Cys Ile Pro Thr Ser Ser Thr Ile Glu Gln
                20                  25                  30

Gln Asn Ser Ala Arg Ile Arg Gln Asn Thr Arg Glu His Pro Ser Thr
            35                  40                  45

Ala Asn Thr Val Asp Arg Thr Asn His Gln Leu Glu Asn Leu Glu Ala
        50                  55                  60

Glu Thr Ala Pro Leu Pro
65                  70
```